United States Patent
Rioux et al.

(10) Patent No.: US 10,661,015 B2
(45) Date of Patent: May 26, 2020

(54) WEARABLE DRUG DELIVERY DEVICE

(71) Applicant: Summit Street Medical LLC, Wallingford, CT (US)

(72) Inventors: Robert F. Rioux, Ashland, MA (US); Matthew Laplaca, Franklin, MA (US); Brian Grasso, Wallingford, CT (US); Matt Bomes, Wellesley, MA (US)

(73) Assignee: Summit Street Medical LLC, Wallingford, CT (US)

( * ) Notice: Subject to any disclaimer, the term of this patent is extended or adjusted under 35 U.S.C. 154(b) by 103 days.

(21) Appl. No.: 15/790,263

(22) Filed: Oct. 23, 2017

(65) Prior Publication Data

US 2018/0117251 A1 May 3, 2018

Related U.S. Application Data

(60) Provisional application No. 62/455,241, filed on Feb. 6, 2017, provisional application No. 62/414,871, filed on Oct. 31, 2016.

(51) Int. Cl.
*A61M 5/20* (2006.01)
*A61M 5/24* (2006.01)
(Continued)

(52) U.S. Cl.
CPC ........ *A61M 5/2033* (2013.01); *A61M 5/1782* (2013.01); *A61M 5/204* (2013.01);
(Continued)

(58) Field of Classification Search
CPC ........ A61M 5/24; A61M 5/2466; A61M 5/20; A61M 2005/2026; A61M 2005/206;
(Continued)

(56) References Cited

U.S. PATENT DOCUMENTS

| 5,669,877 A | 9/1997 | Blomquist |
| 6,223,744 B1 * | 5/2001 | Garon .............. A61M 15/00 |
| | | 128/200.14 |

(Continued)

FOREIGN PATENT DOCUMENTS

| WO | WO 08/014791 | 2/2008 |
| WO | 2013078200 A1 | 5/2013 |

(Continued)

OTHER PUBLICATIONS

International Search Report and written Opinion in the International Application No. PCT/US2017/057803 dated Feb. 21, 2018.

(Continued)

*Primary Examiner* — Jason E Flick
(74) *Attorney, Agent, or Firm* — Knobbe Martens Olson & Bear LLP

(57) ABSTRACT

A wearable drug delivery device has a needle assembly and a drug vial arranged side-by-side. This arrangement makes the device compact so that it can be easily worn around a user's wrist, for example. When the user triggers the device to inject a dose of medication like epinephrine, in an orchestrated sequence, a first spring drives the needle assembly downward and inserts a needle into the user while connecting the needle assembly to the drug vial. A second spring then delivers the dose from the drug vial through the needle and into the user. Advantageously, the small form factor encourages the user to wear the device and have lifesaving medication at the ready.

57 Claims, 51 Drawing Sheets

(51) Int. Cl.
*A61M 5/178* (2006.01)
*A61M 5/31* (2006.01)
*A61M 5/30* (2006.01)

(52) U.S. Cl.
CPC ............ *A61M 5/24* (2013.01); *A61M 5/2466* (2013.01); *A61M 5/3135* (2013.01); *A61M 2005/206* (2013.01); *A61M 2005/2013* (2013.01); *A61M 2005/247* (2013.01); *A61M 2005/3022* (2013.01)

(58) Field of Classification Search
CPC .... A61M 2005/2073; A61M 2005/208; A61M 2005/3022; A61M 5/1782; A61M 5/2033; A61M 5/204; A61M 2005/2013; A61M 5/3135; A61M 2005/247
USPC ........................................................ 604/218
See application file for complete search history.

(56) References Cited

U.S. PATENT DOCUMENTS

| | | | |
|---|---|---|---|
| 6,572,542 | B1 | 6/2003 | Houben et al. |
| 7,967,784 | B2 | 6/2011 | Pongpairochana et al. |
| 8,045,455 | B1 | 10/2011 | Agronow et al. |
| 9,043,217 | B2 | 5/2015 | Cashman et al. |
| 9,687,949 | B2 | 6/2017 | Wasielewski et al. |
| 2004/0092874 | A1 | 5/2004 | Mazidji et al. |
| 2005/0020980 | A1 | 1/2005 | Inoue et al. |
| 2005/0151640 | A1 | 7/2005 | Hastings |
| 2007/0233001 | A1* | 10/2007 | Burroughs ............. A61M 5/20 604/131 |
| 2008/0015512 | A1 | 1/2008 | D'Antonio et al. |
| 2008/0065050 | A1 | 3/2008 | Sparks et al. |
| 2009/0069787 | A1 | 3/2009 | Estes et al. |
| 2010/0152660 | A1* | 6/2010 | Mack ..................... A61M 5/20 604/136 |
| 2011/0054390 | A1 | 3/2011 | Searle et al. |
| 2011/0098656 | A1 | 4/2011 | Burnell et al. |
| 2013/0178791 | A1 | 7/2013 | Javitt |
| 2014/0188505 | A1 | 7/2014 | Cohan et al. |
| 2016/0063838 | A1 | 3/2016 | Lee |
| 2016/0287788 | A1* | 10/2016 | Tremblay ............ A61M 5/2033 |
| 2017/0143900 | A1 | 5/2017 | Rioux et al. |
| 2018/0099093 | A1* | 4/2018 | Ebert ................. A61M 5/2033 |
| 2018/0110925 | A1 | 4/2018 | Rioux et al. |

FOREIGN PATENT DOCUMENTS

| | | |
|---|---|---|
| WO | 2015/070340 A1 | 5/2015 |
| WO | 2016/160341 A1 | 10/2016 |
| WO | 2017091584 A1 | 6/2017 |

OTHER PUBLICATIONS

International Search Report and Written Opinion dated Feb. 21, 2018 in application No. PCT/US2017/056871.
International Search Report and Written Opinion dated May 6, 2019 in application No. PCT/US19/17824.
International Search Report and Written Opinion dated Aug. 6, 2019 in application No. PCT/US19/26955.

\* cited by examiner

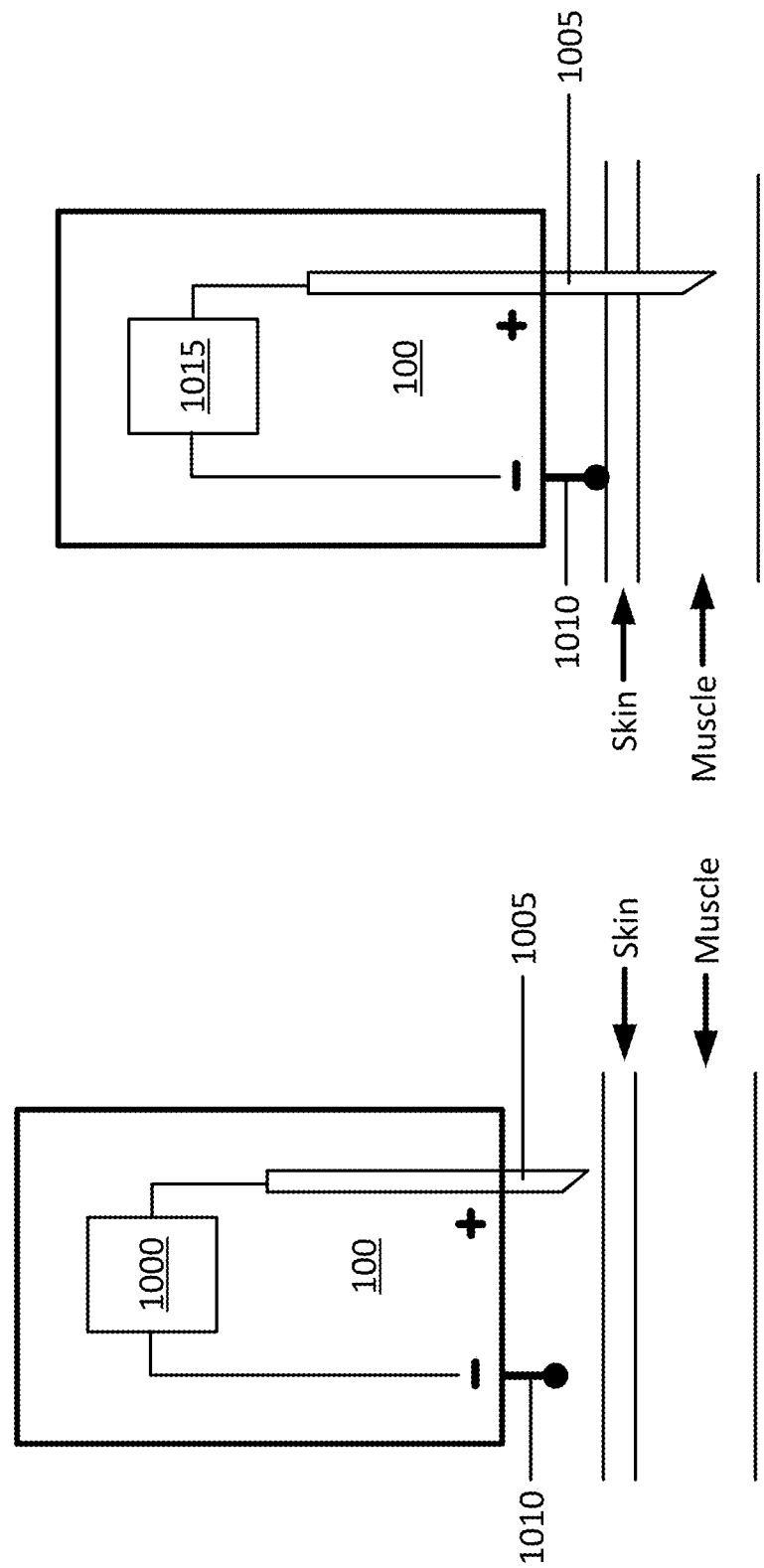

WEARABLE DRUG DELIVERY DEVICE

CROSS REFERENCE TO RELATED APPLICATIONS

This application claims the benefit under 35 U.S.C. § 119(e) of U.S. Provisional Application Ser. No. 62/414,871 filed on Oct. 31, 2016 and U.S. Provisional Application Ser. No. 62/455,241 filed on Feb. 6, 2017, the entire disclosures of which are incorporated herein by reference.

TECHNICAL FIELD

The present invention relates to autoinjectors and in particular to a wearable autoinjector having a needle assembly and a drug vial arranged side by side.

BACKGROUND

Ingesting, inhaling, and/or injecting certain allergens, toxins, and/or other substances can cause profound reactions for at least some and/or all people and/or animals. For example, certain people are highly allergic to certain substances, such as peanuts, shellfish, particular drugs, certain proteins, bee venom, insect bites, etc. The allergic response can lead to anaphylactic shock, which can cause a sharp drop in blood pressure, hives, and/or substantial breathing difficulties caused by severe airway constriction. As another example, inhalation of certain nerve agents can cause severe physiological trauma. Responding rapidly to such exposures can prevent injury and/or death. For example, in response to an exposure leading to anaphylactic shock, an injection of epinephrine (i.e., adrenaline) can provide substantial and/or complete relief from the reaction. As another example, injection of an antidote to a nerve agent can greatly reduce and/or eliminate the potential harm of the exposure. As yet another example, rapid injection of certain drugs, such as a beta blocker, blood thinner, nitroglycerine, antihistamines, insulin, and opioids, etc., can provide substantial relief from various dangerous medical conditions.

An autoinjector is a medical device designed to deliver one or more doses of a particular drug in a manner that facilitates self-administration of the drug via a syringe. By design, autoinjectors are easy to use and are intended to be used by patients or by untrained personnel. They typically are self-contained and designed to require only a few basic steps to operate.

SUMMARY

It is a challenge to package components into a form factor that allows a user to wear a medical device. The medical device can include a syringe, a drug dose, and a source of stored energy needed to auto-inject the dose into the user. A solution to the challenge is a wearable drug delivery device with a needle assembly and a drug vial containing a drug dose arranged side-by-side.

An exemplary wearable drug delivery device includes a handheld portion, including a proximal end, a distal end, and a longitudinal axis extending between the proximal and distal ends. The wearable drug delivery device further includes a trigger portion in slidable engagement with the distal end of the handheld portion and a needle assembly disposed within the handheld portion and aligned with the longitudinal axis. The needle assembly being movable towards the distal end of the handheld portion to an extended position by a penetration spring when the penetration spring is activated by the trigger portion sliding towards the proximal end of the handheld portion. The wearable drug delivery device further includes a drug vial disposed within the handheld portion alongside the needle assembly. The drug vial is moveable towards the distal end of the handheld portion to a seated position by a vial spring when the vial spring is activated by the trigger portion sliding towards the proximal end of the handheld portion. The wearable drug delivery device further includes an integral drug delivery port formed at the distal end of the handheld portion and transverse to the longitudinal axis of the handheld portion. The needle assembly in the extended position and the drug vial in the seated position are in fluid communication with each other by way of the integral drug delivery port.

The handheld portion of the wearable drug delivery device can include a concave surface, the concavity of which is defined by a point offset from the longitudinal axis. The concave surface can be configured to conform to the human wrist.

The handheld portion of the wearable drug delivery device can include a slot. The wearable drug delivery device can further include a band that is received in the slot for wearing the wearable drug delivery device around a part of a user's body.

The handheld and trigger portions of the wearable drug delivery device can be made from a metal, a plastic or a combination of metal and plastic.

The trigger portion of the wearable drug delivery device can slide over the distal end of the handheld portion.

The trigger portion of the wearable drug delivery device can include a trigger arm extending from the trigger portion and through the distal end of the handheld portion. The trigger arm is configured to release energy stored in the penetration spring when the trigger portion slides toward the proximal end of the handheld portion. The trigger portion of the wearable drug delivery device can include two trigger arms.

The wearable drug delivery device can further include a rotator coupled to the drug vial. The rotator and the drug vial are urged towards the distal end of the handheld portion by the vial spring. The wearable drug delivery device can further include a yoke extending from the distal end of the handheld portion towards the proximal end. The rotator rests on the yoke thereby resisting movement toward the distal end of the handheld portion and moving the drug vial to the seated position. The trigger portion can include a trigger blade extending from the trigger portion and through the distal end of the handheld portion. The trigger blade is in slidable engagement with the rotator and is configured to lift the rotator off the yolk and allow the rotator to move towards the distal end of the handheld portion and move the drug vial to the seated position when the trigger portion slides toward the proximal end of the handheld portion.

The trigger blade of the wearable drug delivery can include an angled surface to lift and turn the rotator off the yoke. The trigger portion of the wearable drug delivery device can include three trigger blades.

The needle assembly of the wearable drug delivery device can include a J-shaped needle.

The integral drug delivery port of the wearable drug delivery device can include a vial needle, an exit, and a channel connecting the vial needle to the exit. The vial needle punctures a vial membrane of the drug vial when the drug vial is in the seated position thereby allowing a drug dose to flow through the channel and out the exit. The exit can be a septum seal that is pierced by the needle assembly when the needle assembly is in the extended position.

The wearable drug delivery device can further include a return spring interposed between an exterior surface at the distal end of the handheld portion and an opposing surface on the trigger portion. The return spring provides a force separating the handheld portion from the trigger portion. The wearable drug delivery device can further include a latch extending from the opposing surface of the trigger portion and releasable engaged with the handheld portion. The latch when engaged resists the force separating the handheld portion from the trigger portion. The latch can be a leaf spring. The return spring can be a torsion spring.

The wearable drug delivery device can further include a safety guard that covers the trigger portion and is releaseably attached to the handheld portion by any one of an interference fit and a frangible weld joint.

The wearable drug delivery device can further include a safety guard covering the trigger portion and releaseably attached to the handheld portion. The wearable drug delivery device can further include a strip disposed circumferential between the handheld portion and the safety guard. The strip is configured to be torn away from the handheld portion and the safety guard thereby allowing the safety guard to be removed from the handheld portion and expose the trigger portion.

The handheld portion of the wearable drug delivery device has an exterior surface parallel to the longitudinal axis. The wearable drug delivery device can further include a one-way barb projecting from the exterior surface of the handheld portion and a snap feature joined to the trigger portion by a virtual hinge. When the trigger portion slides toward the proximal end of the handheld portion, the snap feature slides over the exterior surface of the handheld portion and flexes about the virtual hinge, away from the exterior surface, when the snap feature slides over the one-way barb.

BRIEF DESCRIPTION OF THE DRAWINGS

The foregoing and other objects, features and advantages will be apparent from the following more particular description of the examples, as illustrated in the accompanying drawings in which like reference characters refer to the same parts throughout the different views. The drawings are not necessarily to scale, emphasis instead being placed upon illustrating the principles of the examples.

FIGS. 15A-15C are views of an examples dose confirmation module of the wearable drug delivery device of FIG. 1.

FIGS. 21C-F is a series of views of a needle trigger mechanism sequence of the wearable drug delivery device of FIG. 16.

DETAILED DESCRIPTION

Figure 1:
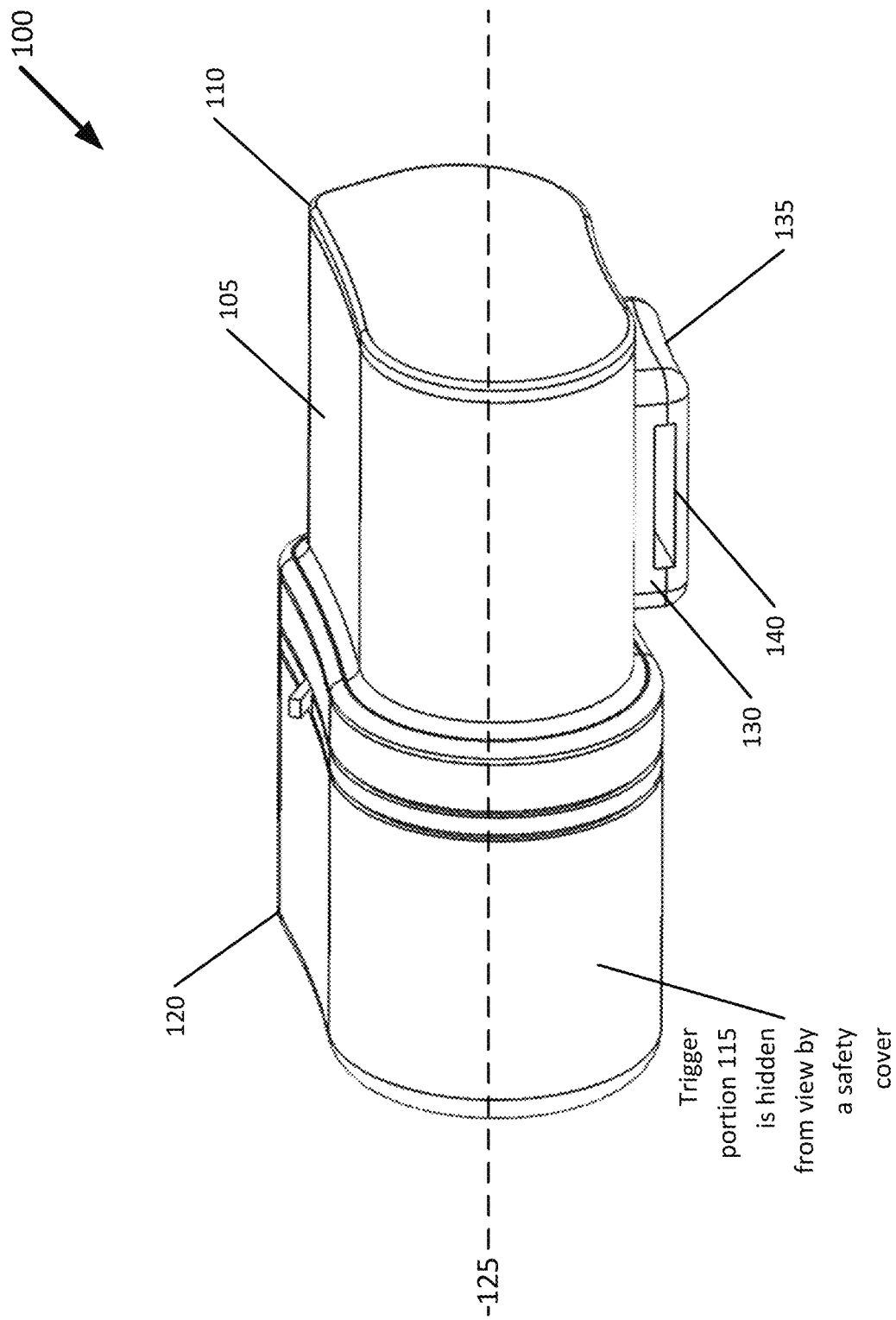
FIG. 1 is perspective view of an example wearable drug delivery device.

The wearable drug delivery device provides a compact drug delivery mechanism that can be worn and can efficiently and/or rapidly deliver a prescribed drug dose. FIG. 1 shows an example of the wearable drug delivery device 100 including a handheld portion 105 at a proximal end 110 and a trigger portion 115 at a distal end 120. (Note: In the figure, the trigger portion 115 is hidden from view by a safety cover. An example of the trigger portion 115 is best seen in FIG. 9B with the safety cover removed from view.) A longitudinal axis 125 extends between the proximal end 110 and the distal end 120. The handheld portion 105 can be constructed from a durable material, such as stainless steel, aluminum, polycarbonate, etc., to protect the internal components of the wearable drug delivery device 100 and/or the user of wearable drug delivery device 100.

In the example shown in FIG. 1, the wearable drug delivery device 100 further includes an adapter 130 for wearing the device on the user. The adapter 130 extends from handheld portion 105 and terminates at a surface 135. The surface 135 is shaped to conform to the user's wrist, arm or other body part. For example, the surface 135 is concaved to engage to the rounded surface the user's wrist. The point of concavity of the surface 135 is defined by a point along an axis offset and parallel to longitudinal axis 125.

The adapter 130 can include a slot 140 for receiving a band (not shown), such as an arm or wrist band, for wearing the wearable drug delivery device 100. The wrist/arm band can be elastic or include a fastener, such as hook and loop, button or snap allowing the user to readily remove the wearable drug delivery device 100 from their body when it's time to use the device.

Figure 2:
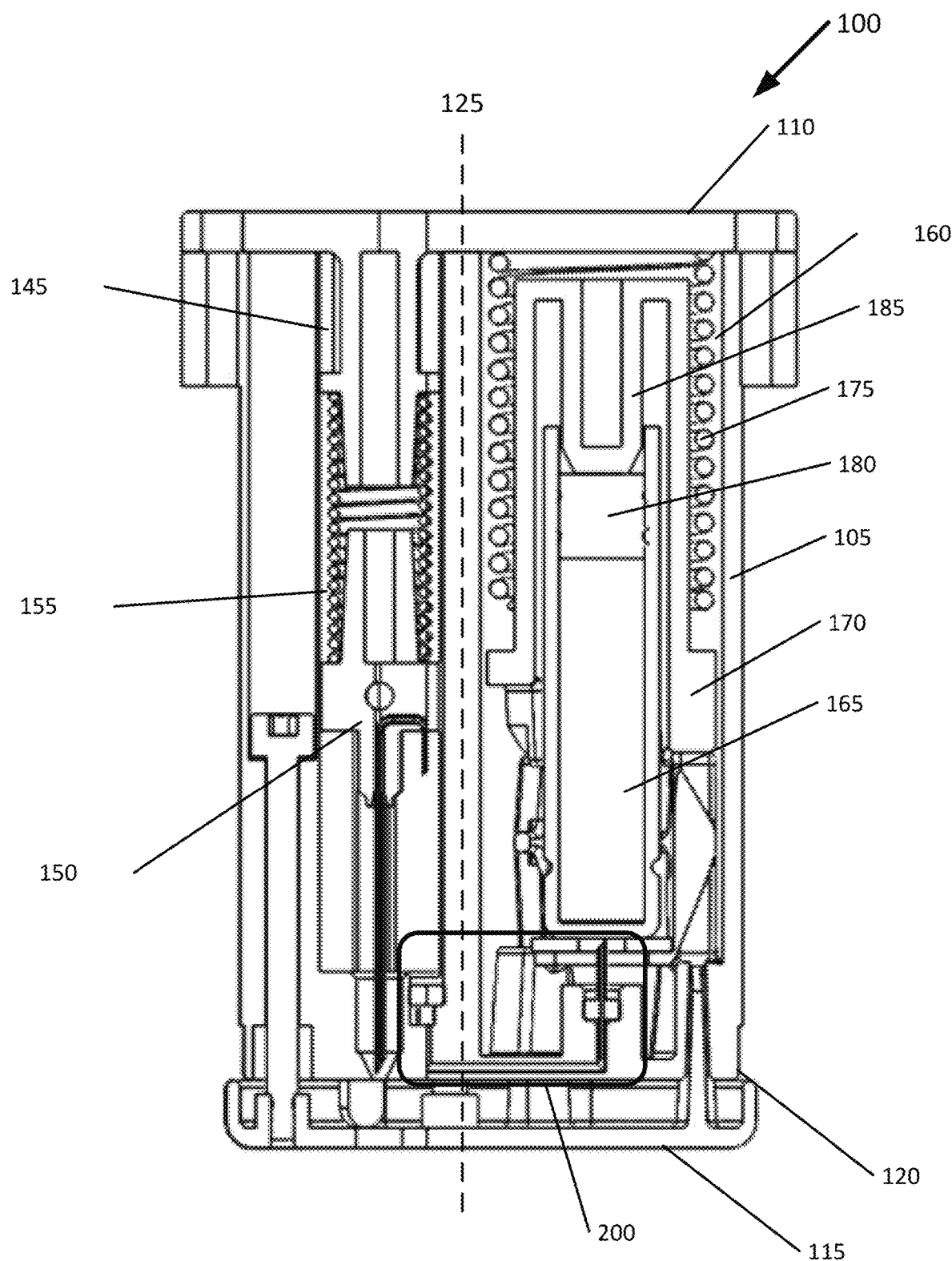
FIG. 2 is a cut-away view of the wearable drug delivery device of FIG. 1.

FIG. 2 shows the insides of the wearable drug delivery device 100. The handheld portion 105 is divided into two compartments that are arranged side-by-side and aligned with the longitudinal axis 125. The first compartment 145 contains a needle assembly 150 and a penetrating spring 155. As will be described in greater below, to pierce the user' skin the penetrating spring 155 moves the needle assembly 150 within the first compartment 145 in the direction of the longitudinal axis 125 from a position at the proximal end 110 to a position at the distal end 120. For ease of reference, the former position is called the "withdrawn position" and the latter portion is called the "extended position". Additionally, the proximal-to distal direction is referred to as the "downward direction," and the opposite direction is the "upward direction".

The second compartment 160 contains a drug vial 165 surrounded in part by a rotator 170 and a piston 185. The piston 185, in turn, is surrounded by a vial spring 175. The concentric arrangement of these parts is advantageous because it allows the wearable drug delivery device 100 to be short and wearable. As will be described in greater detail below, to inject the drug dose into the user, the vial spring 175 moves the drug vial 165, the rotator 170, and the piston 185 downward within the second compartment 160, and further moves a plunger 180 downward within the drug vial 165. By way of non-limiting example, the drug vial 165 can be filled with a dose of epinephrine or insulin.

Figure 3:
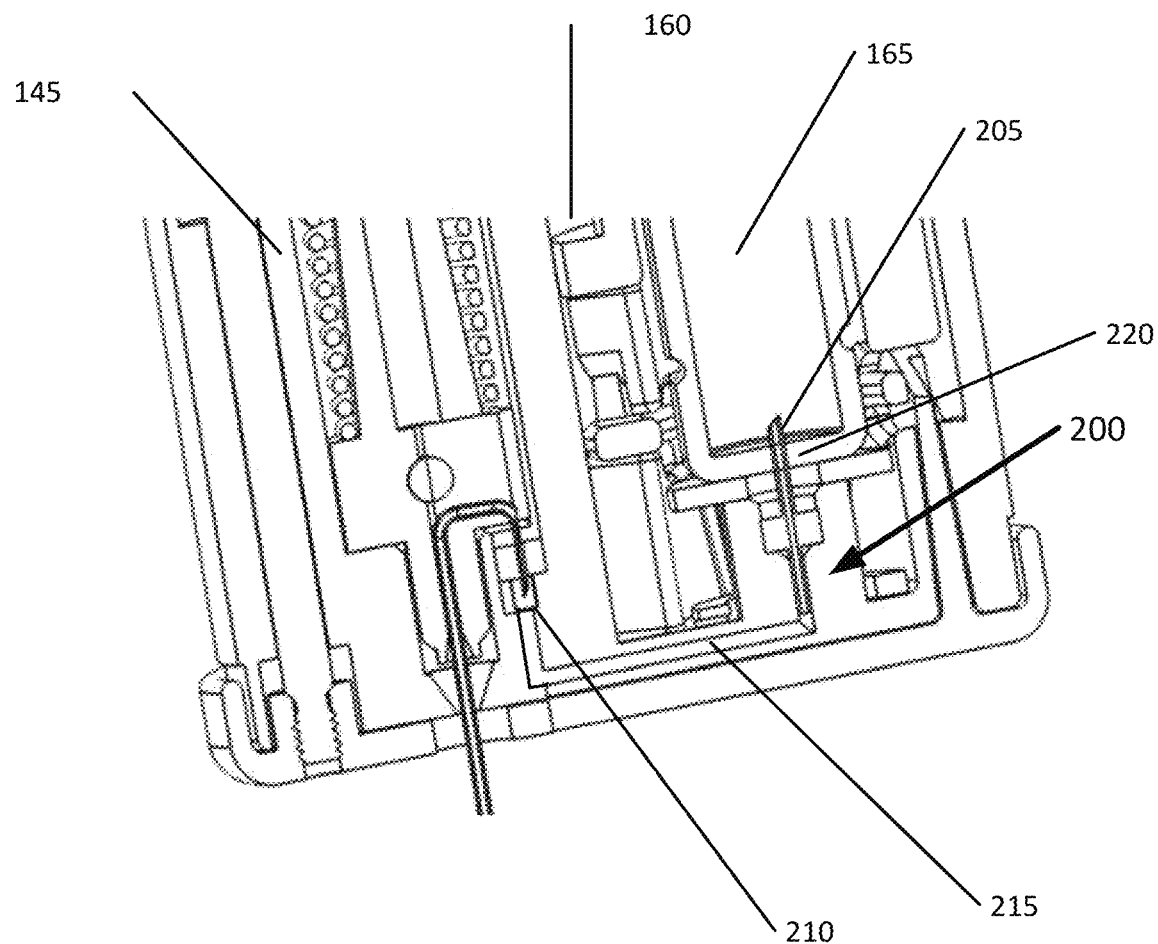
FIG. 3 is a close up view of an example integral drug delivery port of the wearable drug delivery device of FIG. 1.

The wearable drug delivery device 100 further includes at the distal end 120, an integral drug delivery port 200 for providing a path for the drug dose to flow from the drug vial 165 to the needle assembly 150. In the close up view of FIG. 3, the integral drug delivery port 200 extends transversely between the first compartment 145 and the second compartment 160. The integral drug delivery port 200 includes a vial needle 205 (entrance), an exit 210, and a channel 215 extending between them.

When the drug vial 165 is moved in the downward direction, the vial needle 205 encounters a vial membrane 220, which seals the drug vial 165. As the drug vial 165 continues to move downward, the vial needle 205 punctures the vial membrane 220. At this point, the drug vial 165 is in fluid communication with the integral drug delivery port 200. The drug dose flows out of the drug vial 165 through the vial needle 205 and the channel 215, and then out the exit 210.

Figure 4A:
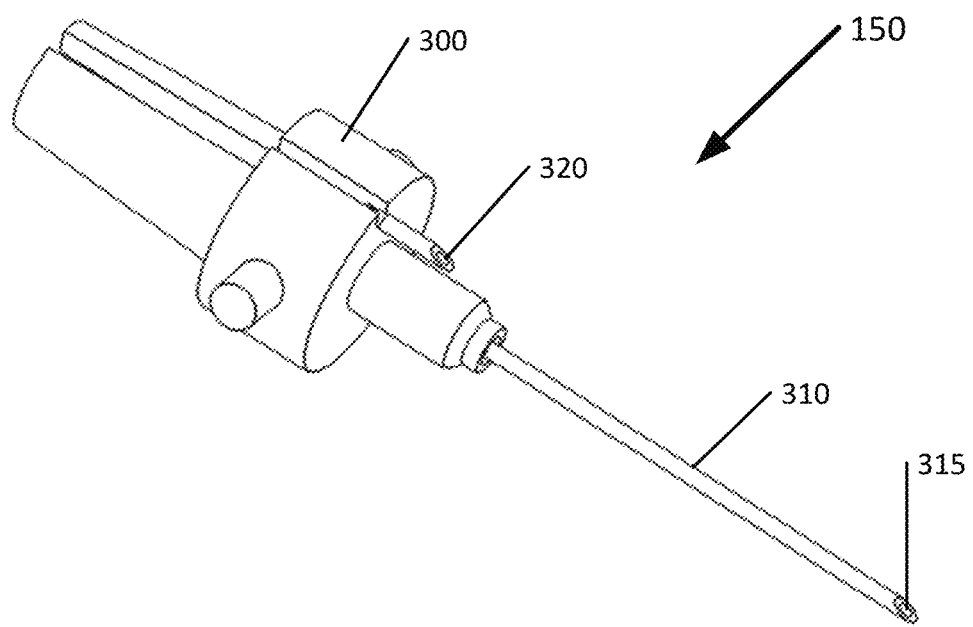
FIGS. 4A and 4B are perspective views of an example needle assembly of the wearable drug delivery device of FIG. 1.
Figure 4B:
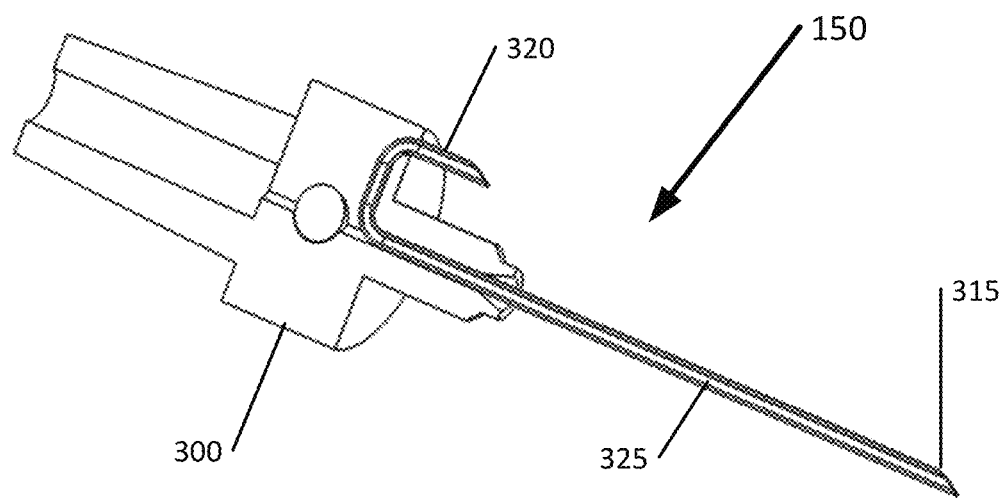

FIG. 4A shows an example of the needle assembly 150, including a needle body 300, a needle 310, and a tip 315. The needle body 300 is the base the needle assembly 150 and includes a needle port 320. The needle 310 extends from the needle body 300 and terminates at the tip 315. As best seen in FIG. 4B, the needle 310 has the approximate shape of the letter "J" with a central lumen 325 extending from the tip 315 at one end to the needle port 320 at the other. Fluid entering the needle port 320 flows through the central lumen 325 and out of the tip 315.

Figure 4C:
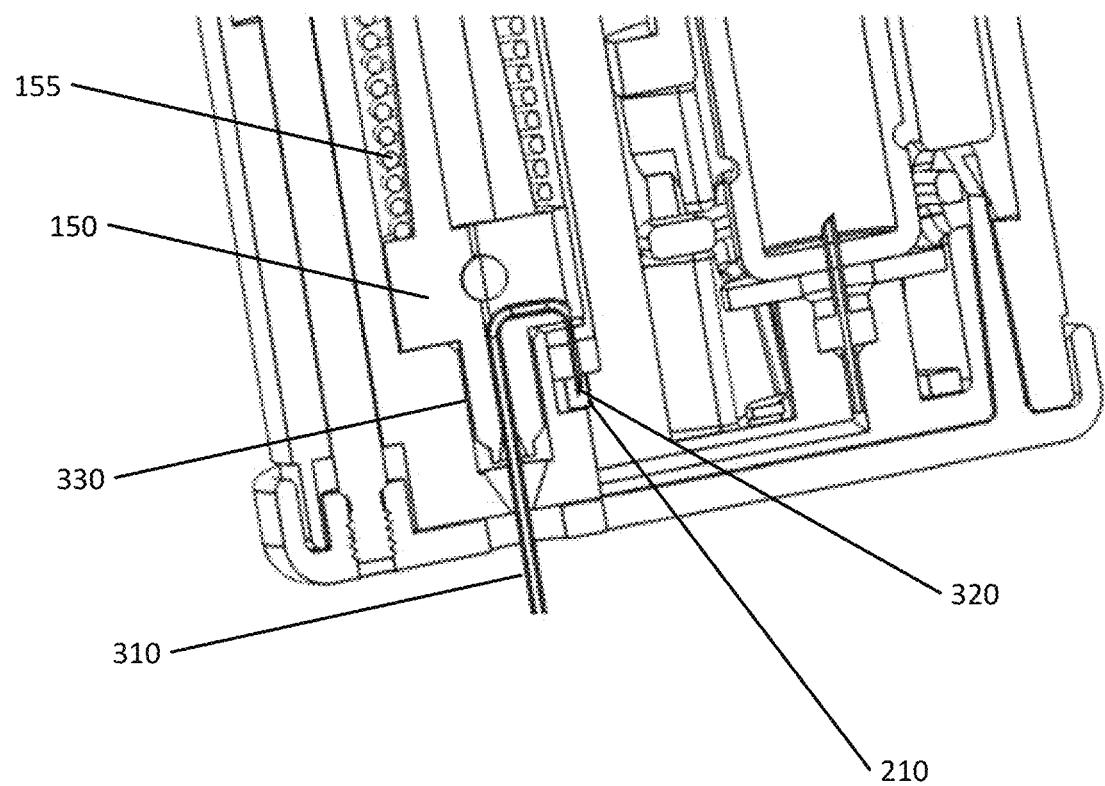
FIG. 4C is a cut-away view of the wearable drug delivery device of FIG. 1 with the needle assembly in the extended position.

FIG. 4C shows the needle assembly 150 in the extended position within a receiving portion 330 of the handheld portion 105. As shown, the receiving portion 330 has a shape complementary to the shape of the needle body 300. The receiving portion 330 includes an upper part, a lower part, and a shoulder connecting them. The upper part corresponds with the needle assembly needle body 300 and includes the exit 210 of the integral drug delivery port 200.

With the needle assembly 150 in the extended position, the exit 210 of the integral drug delivery port 200 and needle port 320 are in fluid communication with each other. In some examples, the exit 210 is a septum seal that is pierced by the needle port 320 when the needle assembly 150 is in the extended position. This is beneficial because the channel 215 is sealed until the needle assembly 150 is positioned correctly. Fluid flows from the drug vial 165 through the integral drug delivery port 200 and the needle port 320, and out of the needle 310. This arrangement is advantageous because it does not require a direct connection between the needle assembly 150 and the drug vial 165. In some examples, the receiving portion 330 may be made leak resistant by a downward force applied from the penetration spring 155.

Figure 5A:
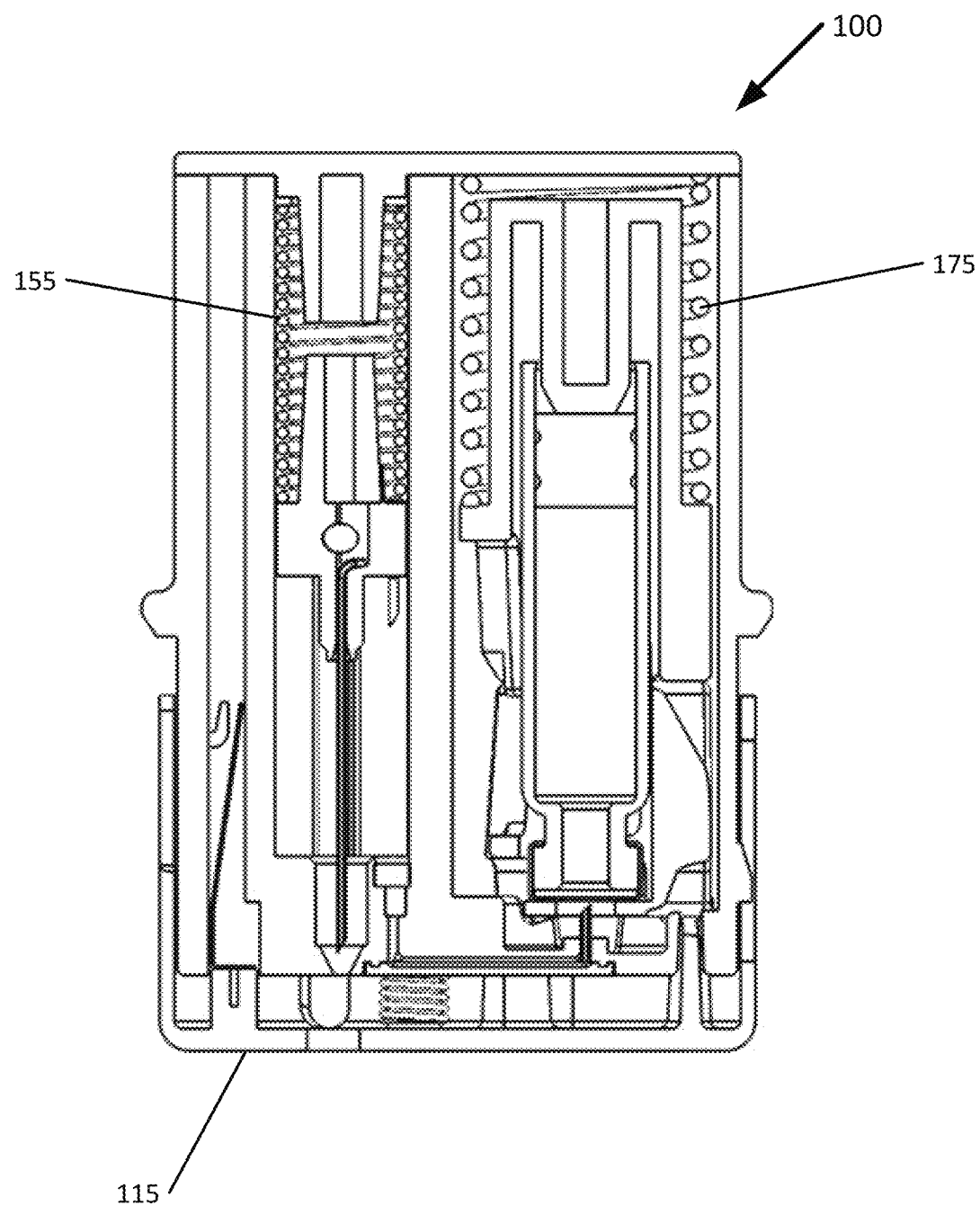
FIGS. 5A-C is a series of views of a drug delivery sequence of the wearable drug delivery device of FIG. 1.
Figure 5B:
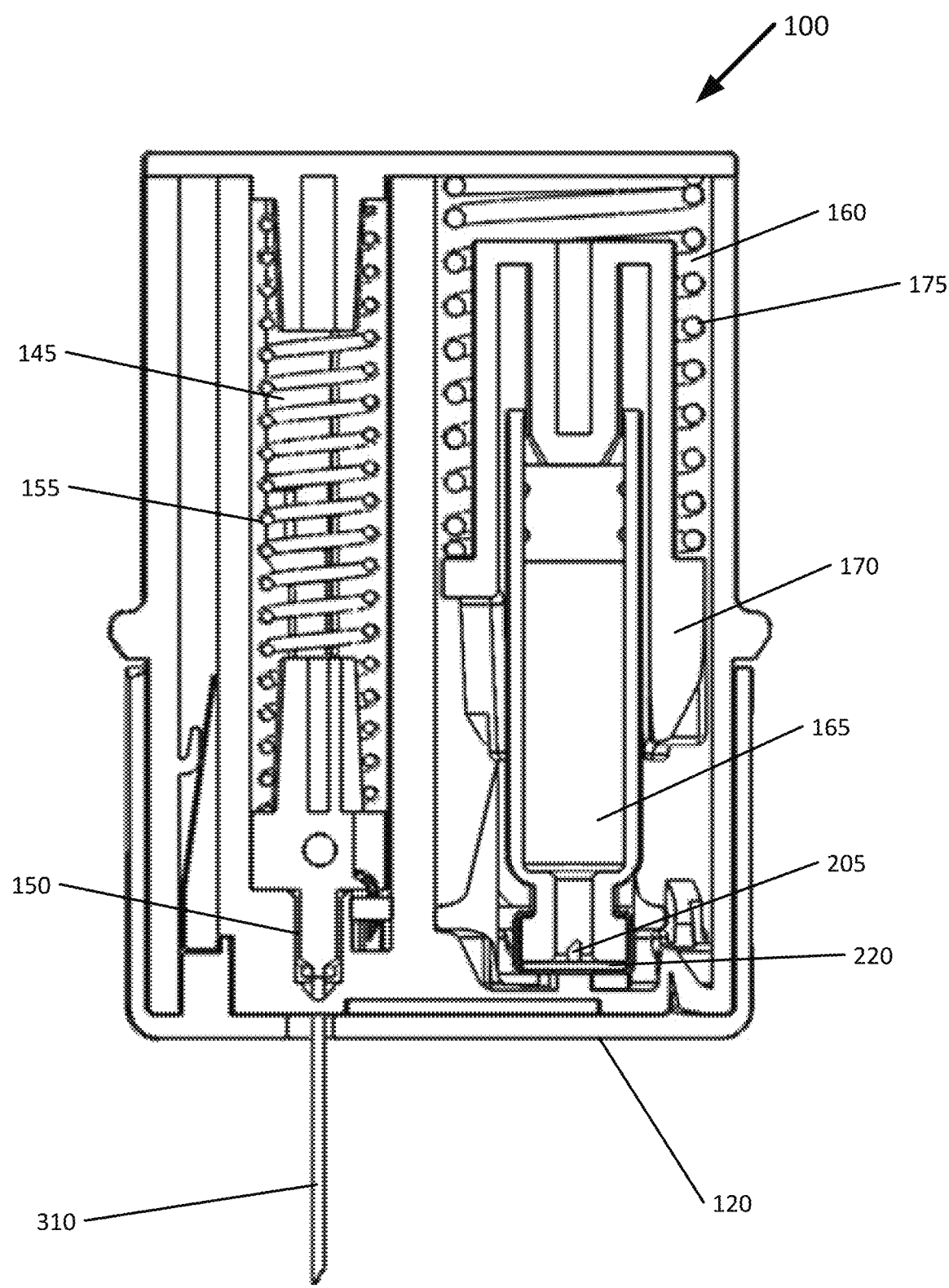

FIGS. 5A-B shows an example sequence of orchestrated events starting with a user triggering the wearable drug delivery device 100 and ending with a drug dose delivered to the user. Starting in FIG. 5A, the user triggers the wearable drug delivery device 100 by depressing the trigger portion 115 against their thigh, for example. This simultaneously actuates a needle trigger mechanism and a delivery trigger mechanism (both of which are described in greater detail below). The concurrent activation, in turn, releases energy stored in the penetration spring 155 and the vial spring 175.

In FIG. 5B, the penetration spring 155 drives the needle assembly 150 downwards within the first compartment 145 from the withdrawn position to the extended position. In the extended position, the needle 310 projects beyond the distal end 120 of the wearable drug delivery device 100 and into the user's thigh. Contemporaneous with the needle deployment, the vial spring 175 drives the drug vial 165, the rotator 170, and the piston 185 downward toward the vial needle 205.

Figure 5C:
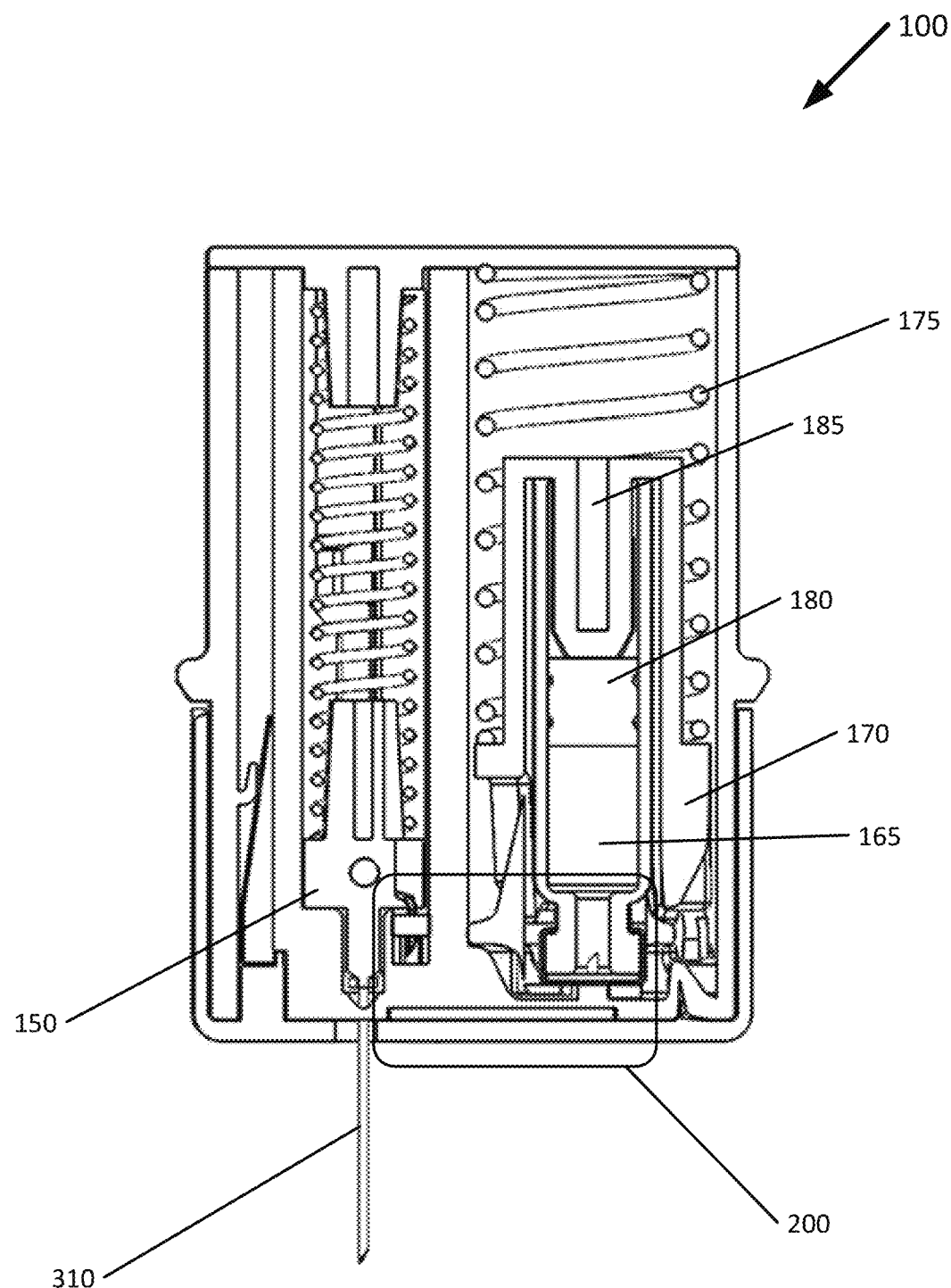

In FIG. 5C, the drug vial 165, the rotator 170, and the piston 185 continue moving downward until the vial needle 205 punctures the vial membrane 220. The drug vial 165 continues to move downward until a stop 225 extending up from the distal end 120 prevents the drug vial 165 from moving further downward. At this point, the drug vial 165 is fully seated in its final position (i.e., the seated position). The vial spring 175, however, is not yet fully extended and still has more travel left.

Continuing in FIG. 5C, as the vial spring 175 continues to push the piston 185 downward, the piston 185 drives the plunger 180 downward within the seated drug vial 165 expelling the drug dose from the drug vial 165. The expelled drug dose flows through the integral drug delivery port 200 and needle assembly 150, out the needle 310, and into the user's thigh.

Figure 6B:
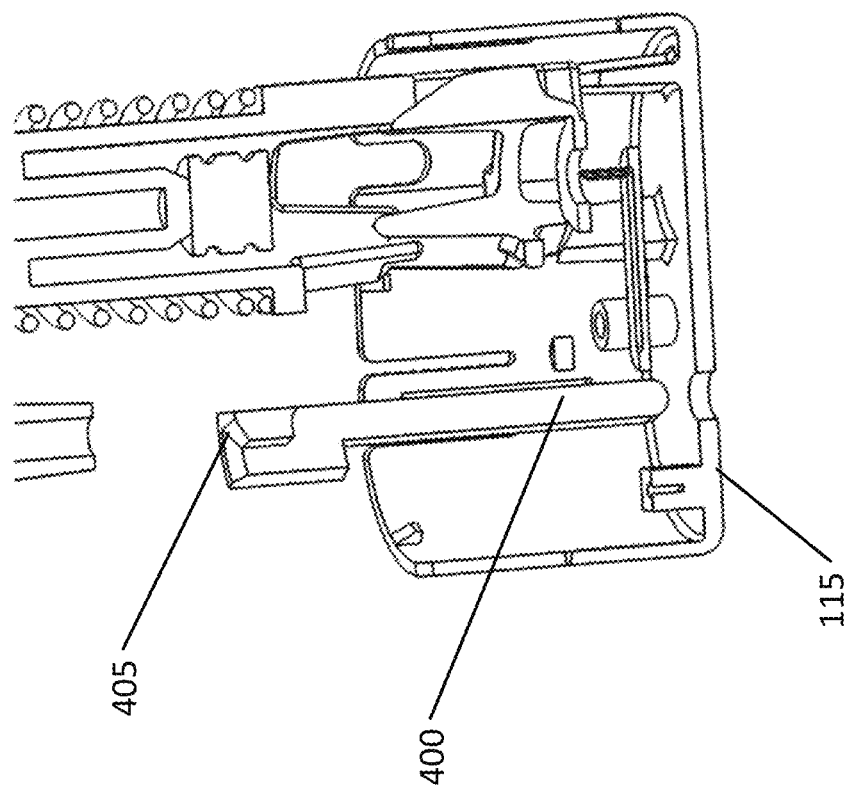
FIGS. 6A-C are views of example components of a needle trigger mechanism of the wearable drug delivery device of FIG. 1.
Figure 6A:
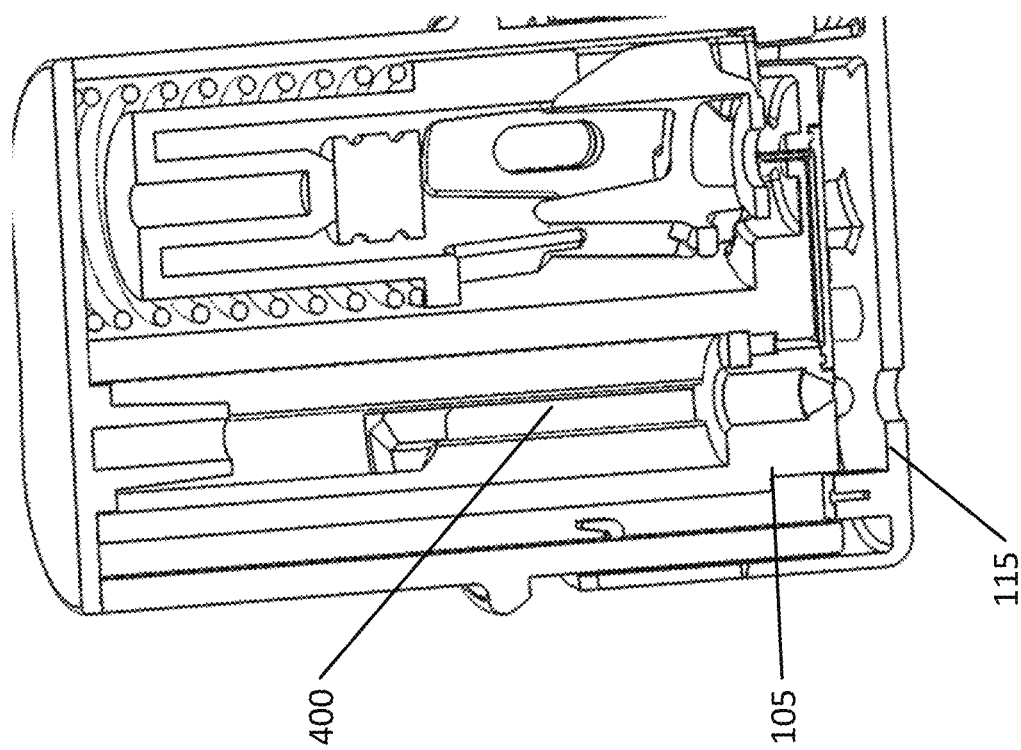

Turning now to a detailed discussion of the needle trigger mechanism, the mechanism operates via the trigger portion 115, which contacts the user's target injection area (e.g., thigh). The trigger portion 115 includes two trigger arms one that extend into the handheld portion 105, one of which is shown in FIGS. 6A and 6B. When the user pushes down on the trigger portion 115, the trigger arms 400 move upward within the handheld portion 105.

Figure 6C:
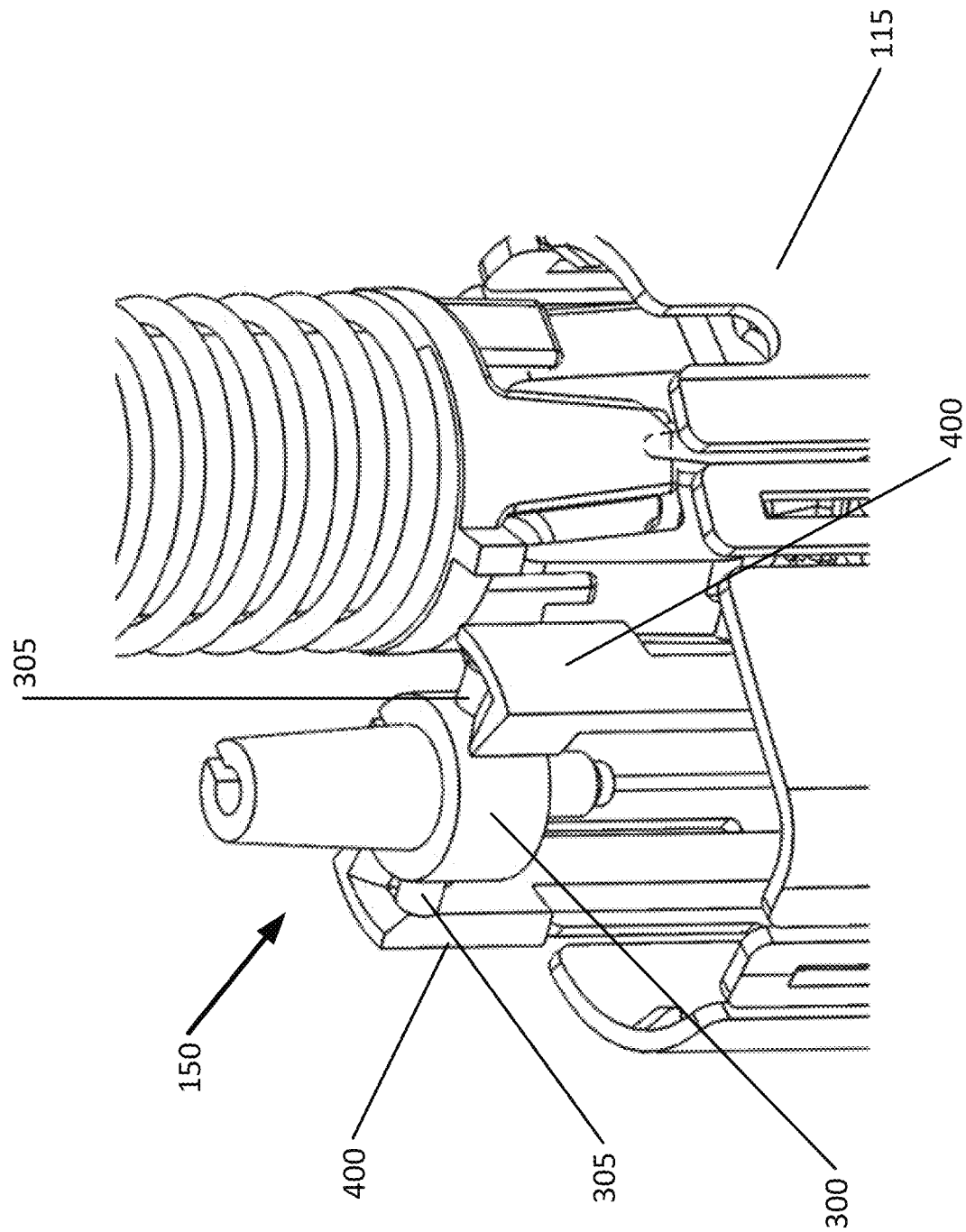

As more clearly seen in FIGS. 6B and 6C with the handheld portion removed from view, each of the trigger arms 400 has a support pad 405 that normally supports the spring loaded needle assembly 150. The needle body 300 includes ears 305 each normally supported by a trigger arm support pad 405. The example needle body 300 shown in FIG. 6C includes the ears 305 spaced 180° apart, which corresponds to a similar arrangement of the trigger arms 400.

Figure 6D:
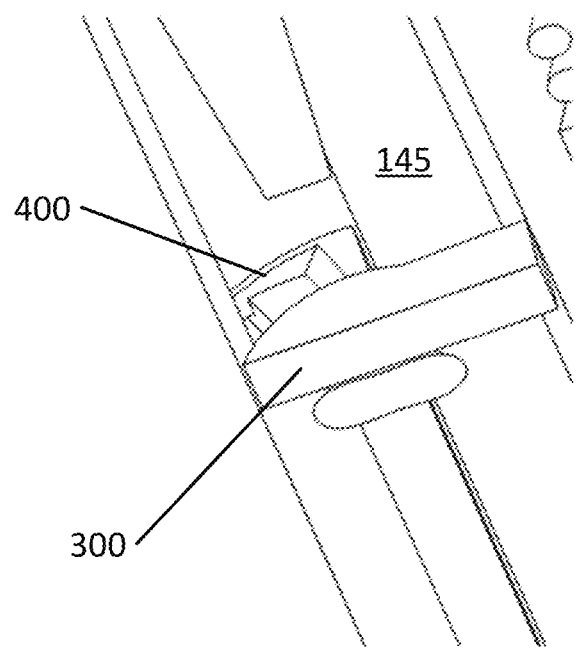
FIGS. 6D-G is a series of views of the operation of the needle trigger mechanism of the wearable drug delivery device of FIG. 1.
Figure 6E:
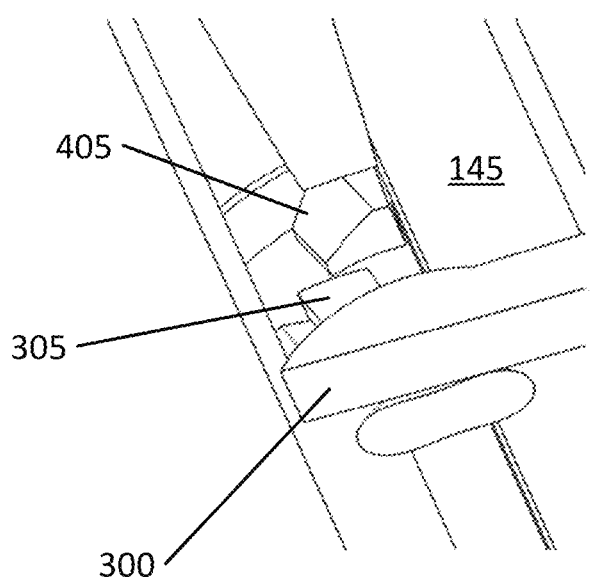
Figure 6F:
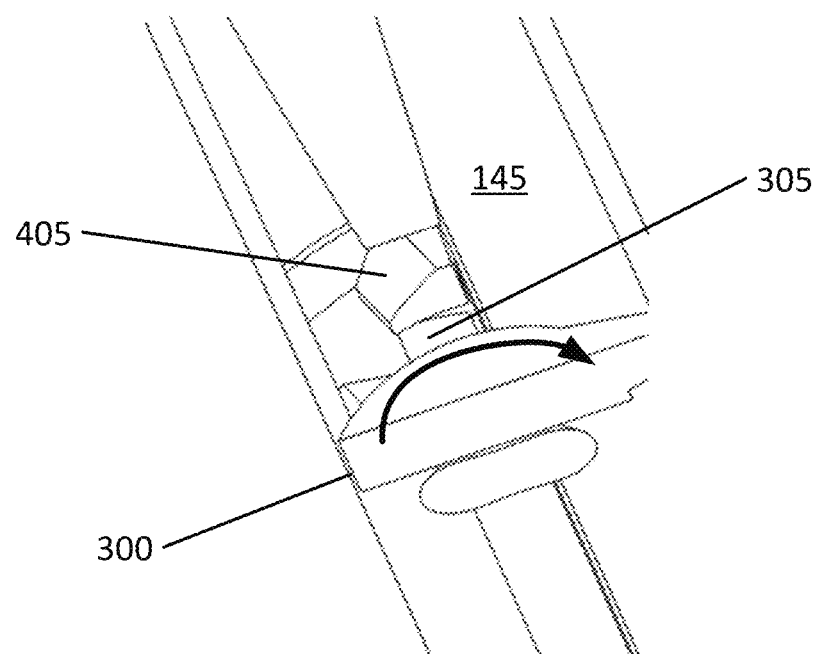
Figure 6G:
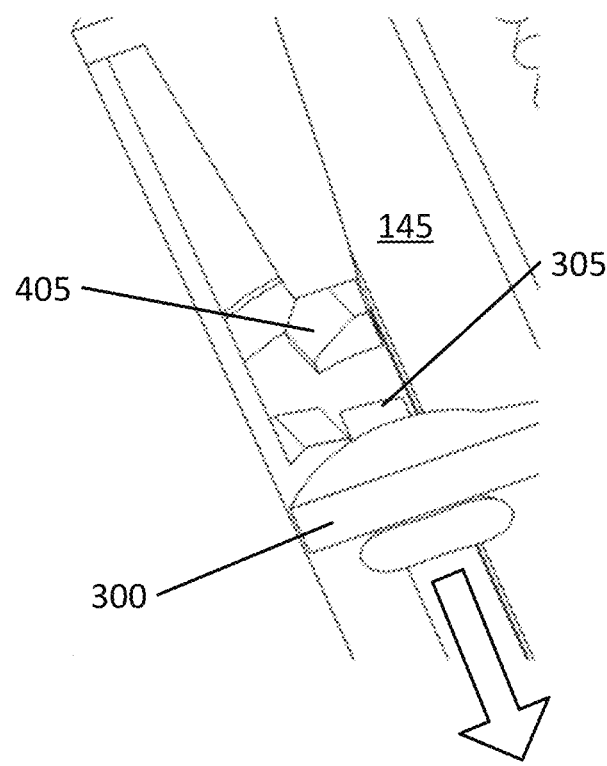

The support pads 405 and ears 305 can each have an angled surface that facilitates cooperation between the needle body 300 and the trigger arms 400. As the trigger arms 400 are moved upward by the trigger portion 115, the angled surfaces cause the needle body 300 to lift and rotate away from the trigger arm support pads 405, as seen in FIG. 6D (showing one of the trigger arms 400). Once the trigger arm support pads 405 reach a trigger point, as seen in FIG. 6E (showing one of the trigger arms 400), the needle body 300 can rotate underneath the trigger arm support pads 405, as seen in FIG. 6F (showing one of the trigger arms 400). No longer supported, the needle assembly 150 can then travel freely downward towards the target injection site (denoted by the arrow), as seen in FIG. 6G (showing one of the trigger arms 400).

Figure 7A:
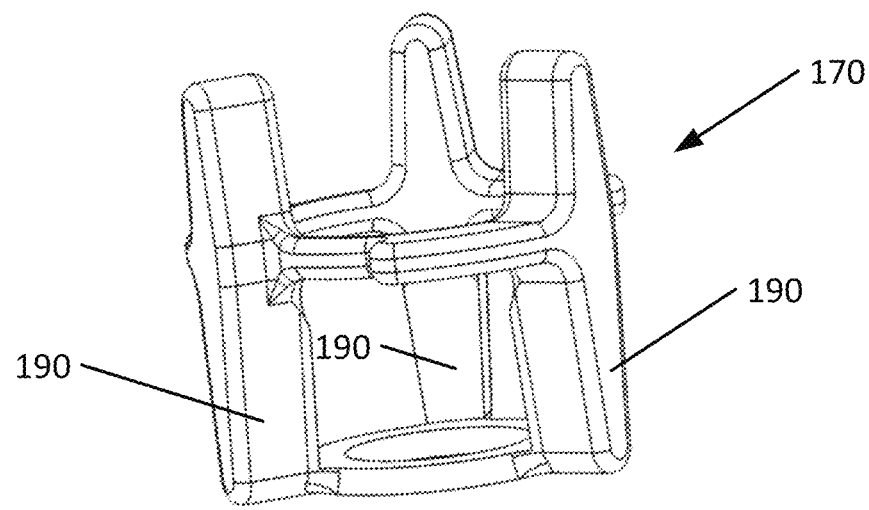
FIGS. 7A-7C are views of example components of a delivery trigger mechanism of the wearable drug delivery device of FIG. 1.
Figure 7B:
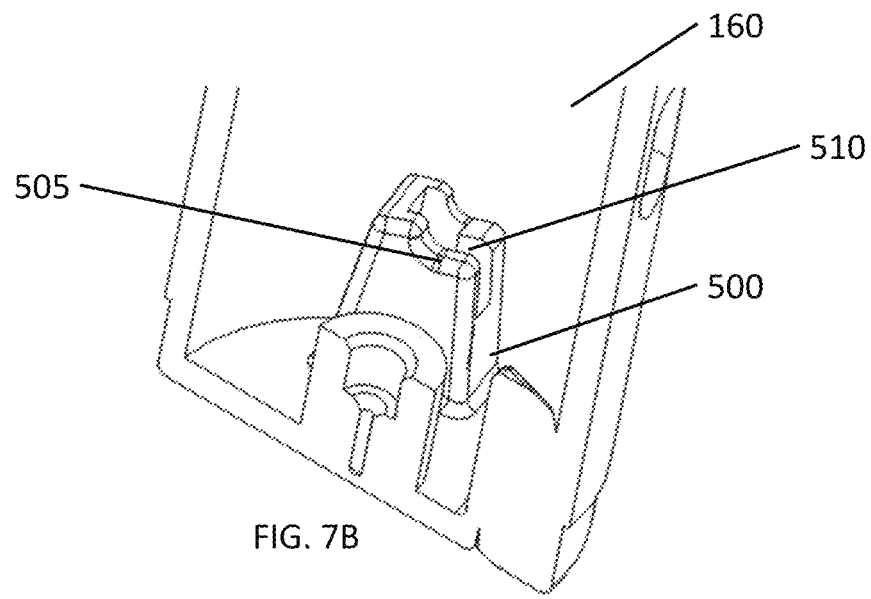

Turning now to a detailed discussion of the delivery trigger mechanism, like the needle trigger mechanism described above, the mechanism also operates via the trigger portion 115. FIG. 7A shows the rotator 170 including a trio of legs 190 (there can be fewer legs, e.g., two or more legs, e.g., four). The legs 190 rest on a trio of corresponding yokes 500 extending from the distal end of the second compartment 160 shown in FIG. 7B. The yokes 500 resist downward movement of the rotator 170 caused by the vial spring 175 (of FIG. 2). The yokes 500 have shaped surfaces 505 corresponding to the shape of the legs 190 to further inhibit downward movement. Each of the yokes 500 has a passageway 510 extending between the inside and outside of the second compartment 160.

Figure 7C:
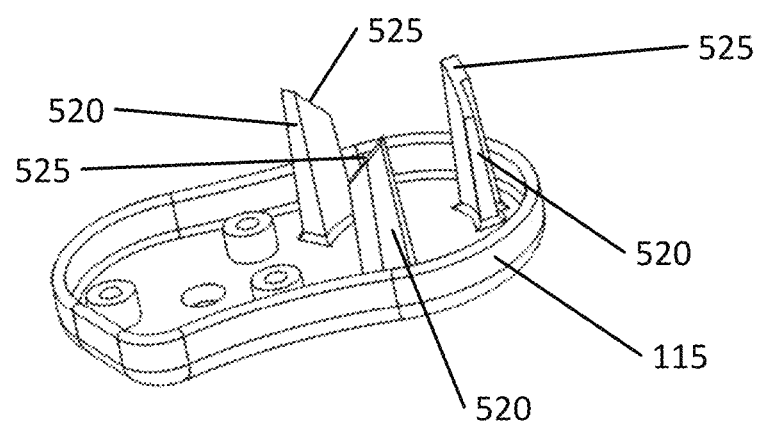

FIG. 7C shows a trio of angled trigger blades 520 extending from the distal end of the trigger portion 115. Each of the blades 520 has angled surface 525 at its end that encourages the rotator 170 to turn in a single direction. When the trigger portion 115 is depressed against the user's thigh, for example, the angled trigger blades 520 slide through the passageways 510 with the angled surfaces 525 extending beyond the shaped surfaces 505.

The operation of the delivery trigger mechanism is now described with reference to FIGS. 8A-8D showing one of the rotator legs 190, one of the yokes 500, and one of the angled trigger blades 520. Before activating the mechanism, the rotator legs 190 are pushed down into the yokes 500 (shown as an arrow pointing to the bottom of the figure) by the vial spring 175 (of FIG. 2). The shaped surfaces 505 further hold the legs 190 in place. The angled trigger blades 520 sit below the shaped surfaces 505 within the passageways 510 and do not contact the legs 190.

Figure 8A:
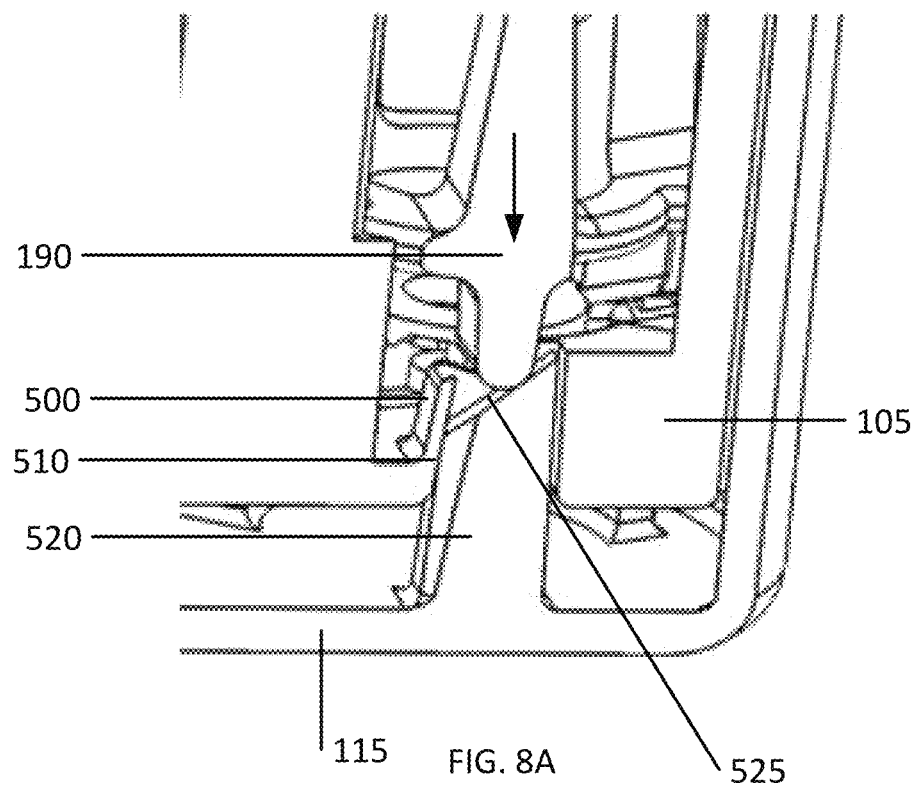
FIGS. 8A-D is a series of views of the operation of the delivery trigger mechanism of the wearable drug delivery device of FIG. 1.
Figure 8B:
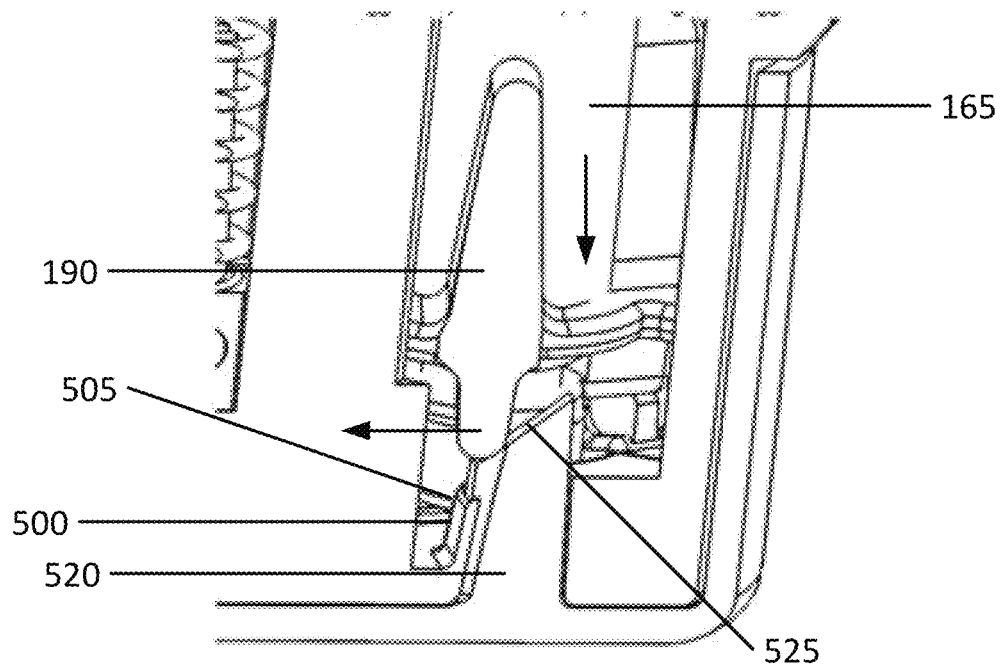

Shown in FIG. 8B, when the trigger portion 115 moves towards the handheld portion 105, the angled trigger blades 520 slide upward within the passageways 510 and contact the rotator legs 190. Due to the incline of the angled surfaces 525, the angled trigger blades 520 initially lift the legs 190 off of the yokes 500. The incline of the angled surfaces 525 together with downward force from the vial spring 175 (of FIG. 2) cause the legs 190 to then slide along the surfaces 525 turning the rotator 170 in the process (not shown).

Figure 8C:
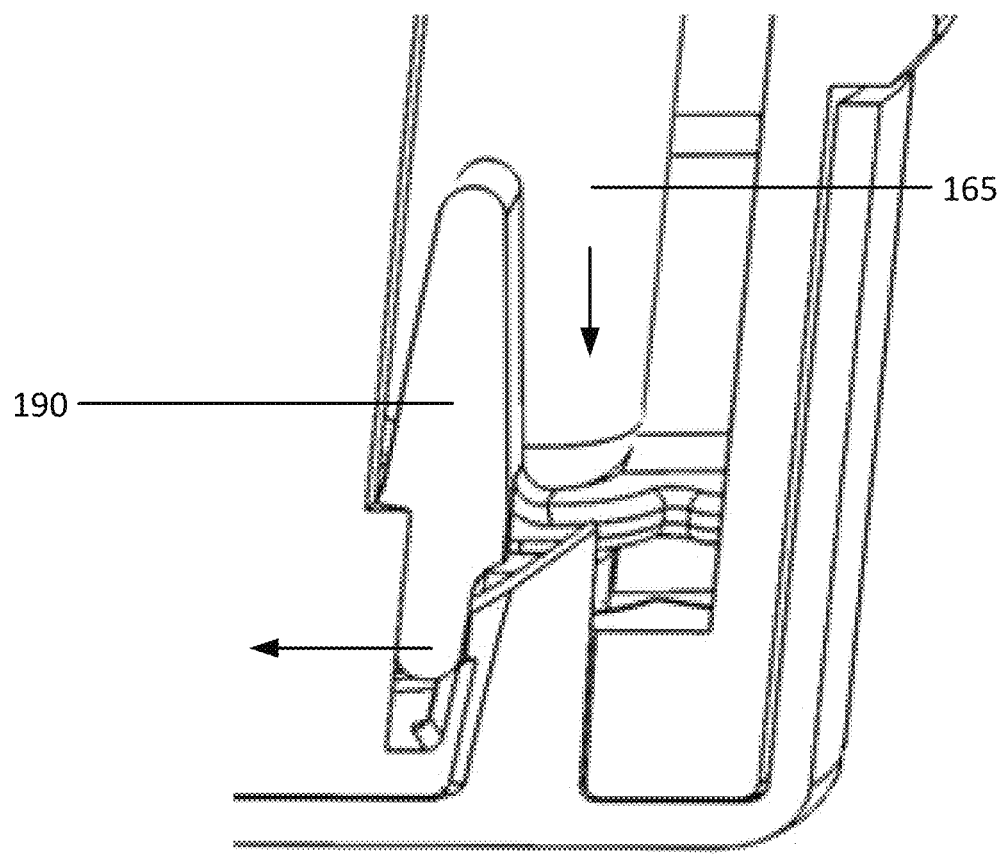
Figure 8D:
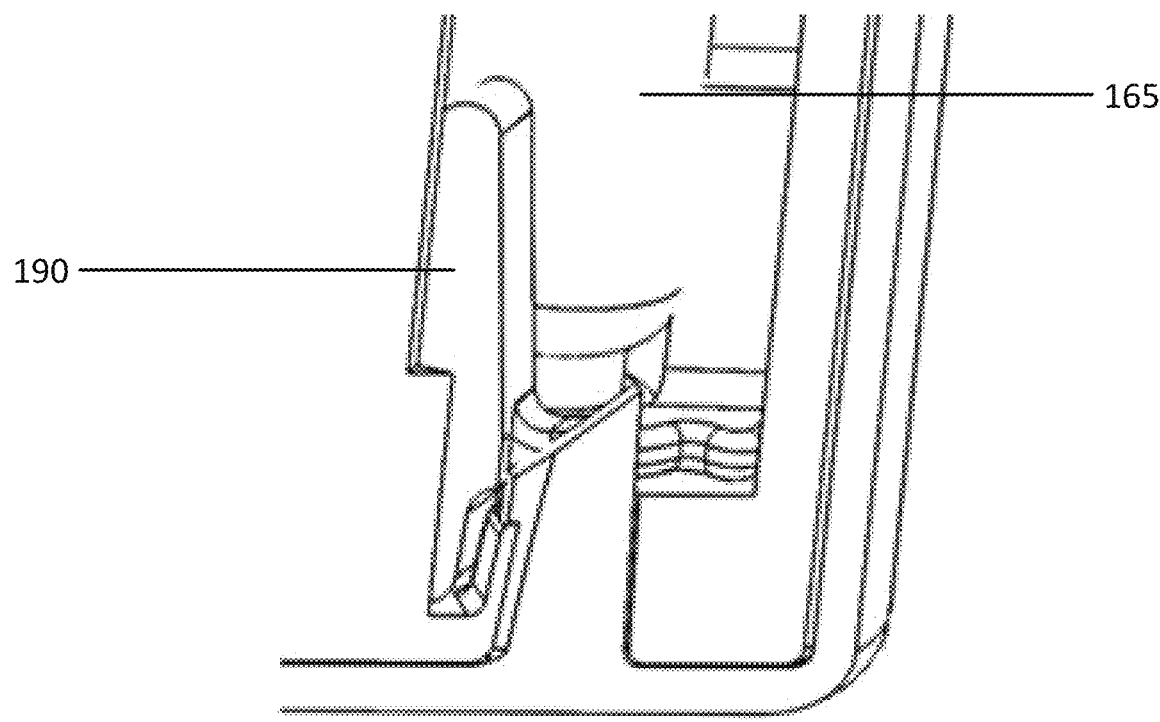

Shown in FIG. 8C, the rotator 170 slides off of the angled trigger blades 520 (shown as an arrow pointing to the left of the figure) and while being pushed downward (shown as an arrow pointing to the bottom of the figure). FIG. 8E shows the rotator 170 shown fully rotated off the yokes 500 and in final position.

Figure 9A:
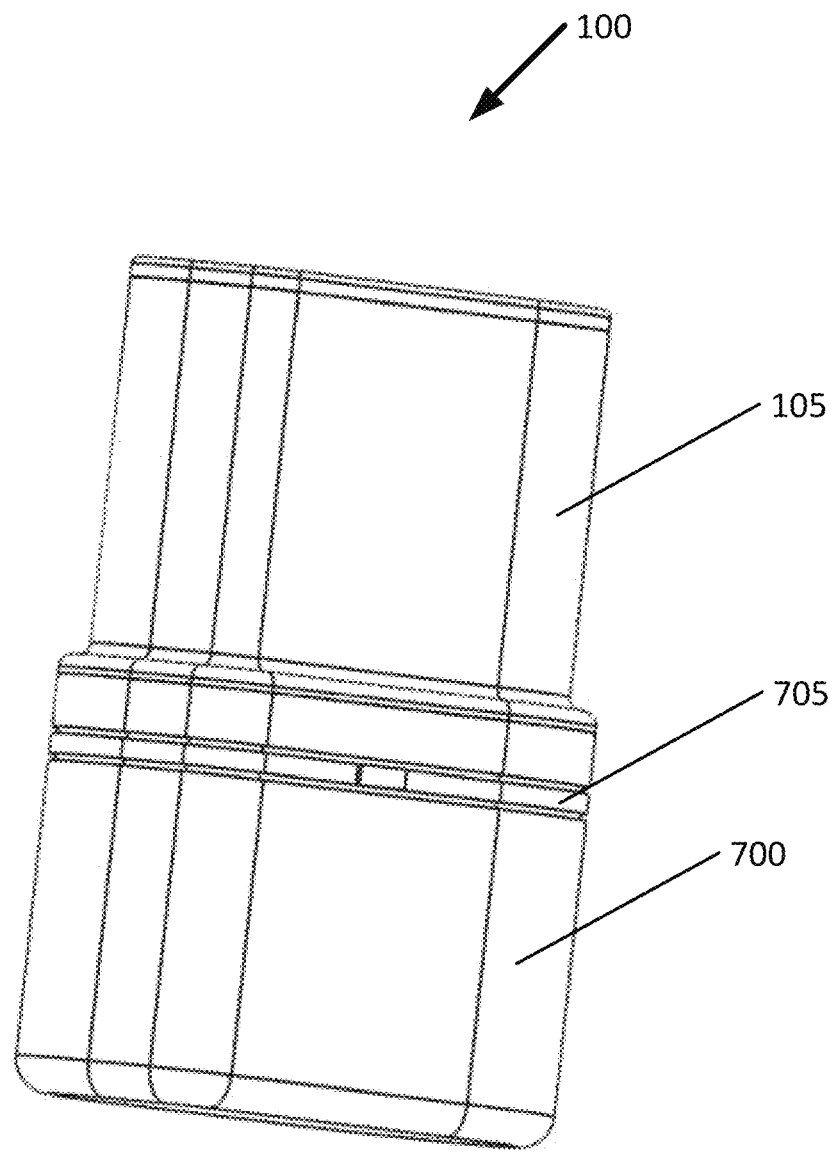
FIG. 9A is a view of the wearable drug delivery device of FIG. 1 with an example safety guard attached at the distal end of the device.
Figure 9B:
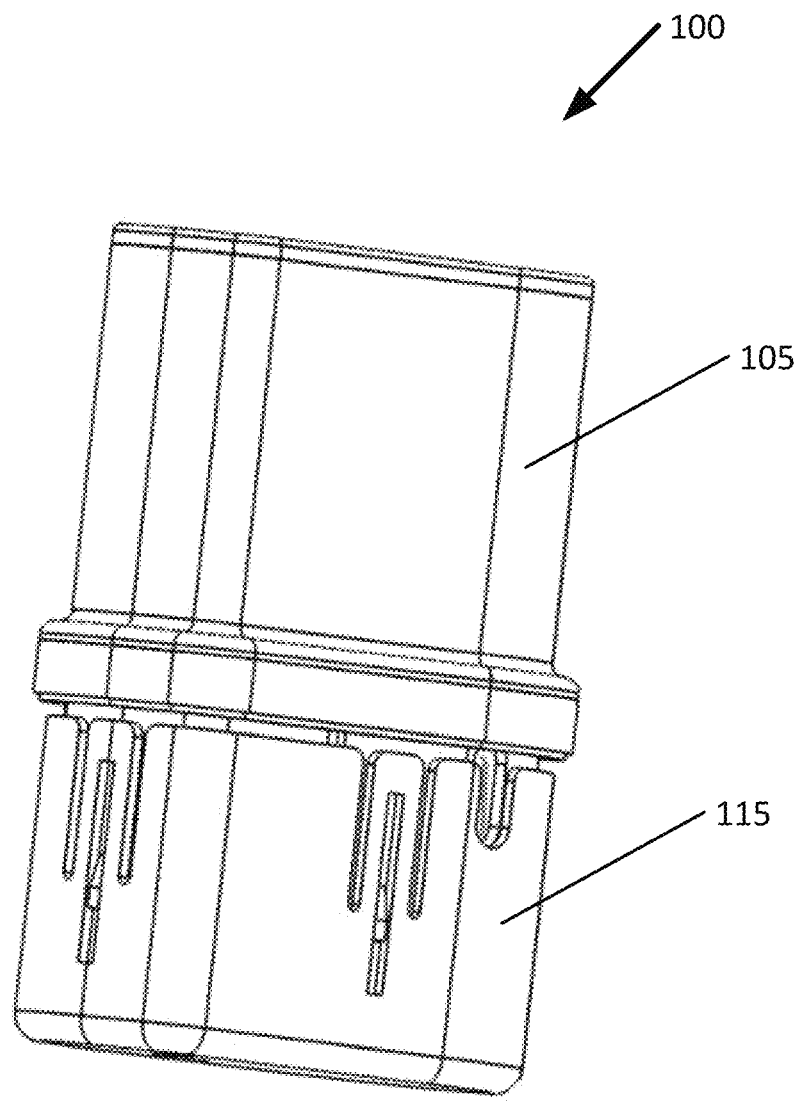
FIG. 9B is a view of the wearable drug delivery device of FIG. 1 with the safety guard removed from the distal end of the device.

FIG. 9A shows an safety guard 700 attached to the handheld portion 105 covering the trigger portion (hidden from view). The safety guard 700 prevents the wearable drug delivery device 100 from being triggered, inadvertently. The safety guard 700 can also act as a sterile barrier and/or a barrier to dirt and water intrusion. The safety guard 700 can be attached to the handheld portion 105 by way of a frangible weld joint formed by a process, such as such as laser welding or ultrasonic welding. The safety guard 700 can also be attached to the handheld portion 105 by friction or interference fit.

The safety guard 700 can be removable by simple force or by using a tear-away strip 705 as shown in the figure. In the example shown, the tear-away strip 705 is disposed circumferentially between the handheld portion 105 and the safety guard 700. In use, the user pulls on the tear-away strip 705 to remove the tear-away strip 705 from the wearable drug delivery device 100. This separates the safety guard 700 from the handheld portion 105. The user action can be facilitated by one or more pre-weakened areas (not shown) in the tear-away strip 705. For example, material joining the tear-away strip 705 to the handheld portion 105 and the safety guard 700 can be thinned making it easier to remove the tear-away strip 705 away from the wearable drug delivery device 100. In another example, material joining the tear-away strip 705 to the handheld portion 105 and the safety guard 700 can be perforated, making it easier to peel the tear-away strip 705 away from the wearable drug delivery device 100. FIG. 9B shows the wearable drug delivery device 100 ready for use with safety guard removed and the trigger portion 115 exposed.

Figure 9C:
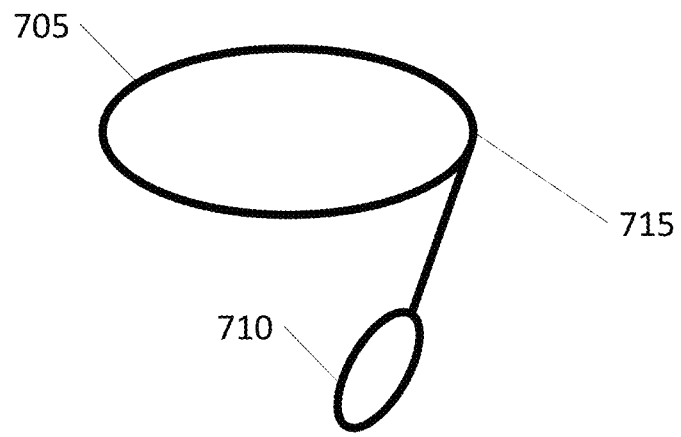
FIGS. 9C and 9D are views of a tear-away strip with a pull ring that can be used with and removed from the wearable drug delivery device of FIG. 1.

FIG. 9C shows a pull ring 710 extending from a point along the tear-away strip 705. The pull ring 710 facilitates removing the tear-away strip 705 from the wearable drug delivery device 100 to allow the device 100 to be triggered. The pull ring 710 can swing towards or away from the tear-away strip 705 by way of a virtual hinge 715. The virtual hinge 715 is located at the base of the pull ring 710 where it extends from the tear-away strip 705.

When the user wears the wearable drug delivery device 100 around their wrist (or other body part), the pull ring 710 swings towards the wearable drug delivery device 100, and is sandwiched between the wearable drug delivery device 100 and the user's wrist (or other body part). In this position, the user cannot access or otherwise use the pull ring 710 to remove the tear-away strip 705 and thus, cannot trigger the wearable drug delivery device.

Figure 9D:
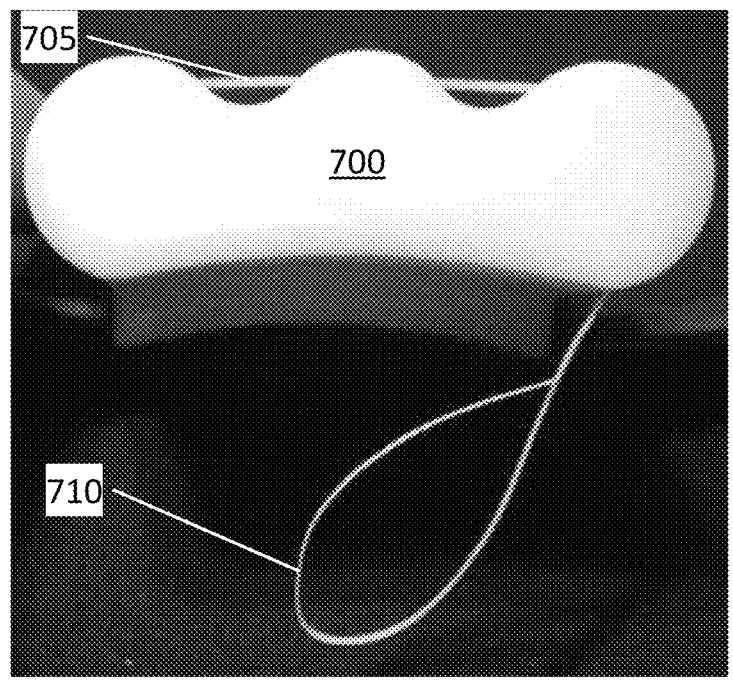

As shown in FIG. 9D, when the user removes the wearable drug delivery device 100 from their wrist (or other body part), the pull ring 710 swings away from the wearable drug delivery device. In this deployed position, the user can access the pull ring 710 and pull on it to remove the tear-away strip 705 from the wearable drug delivery device 100; and thus can trigger the device 100. This feature is useful because the wearable drug delivery device cannot be activated while wearing the device. The wearable drug delivery device can only be activated when the device is removed from the user's wrist (or other body part), thus adding to the safety of the device.

Figure 10B:
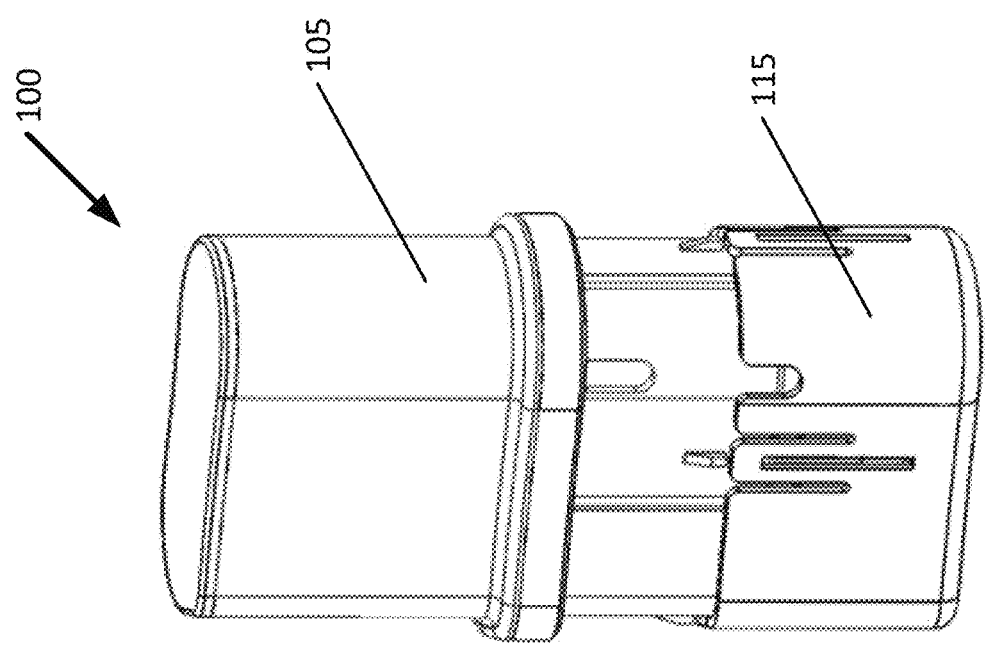
FIG. 10B is a view of the wearable drug delivery device of FIG. 1 after use.
Figure 10A:
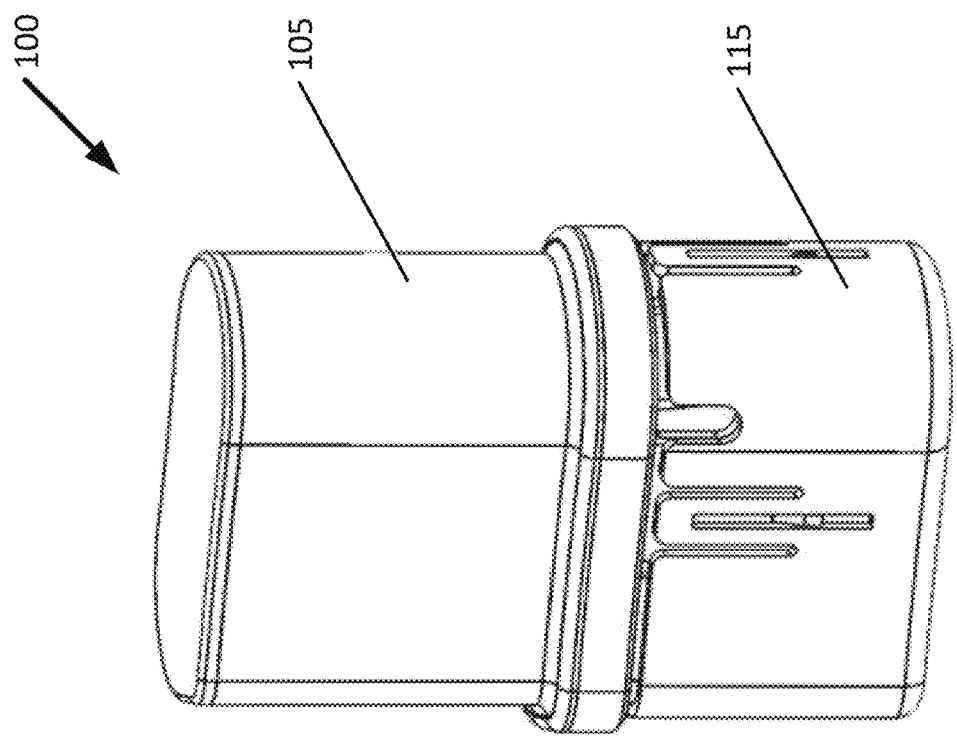
FIG. 10A is a view of the wearable drug delivery device of FIG. 1 before use.

The trigger portion 115 can also act as a needle guard/sharps protector after the wearable drug delivery device 100 is used. FIG. 10A shows the arrangement of the wearable drug delivery device 100 before it is used with the trigger portion 115 proximal (close) to the handheld portion 105. FIG. 10B shows the arrangement of the wearable drug delivery device 100 after it is used with the trigger portion 115 distal (far) from the handheld portion 105.

Figure 10C:
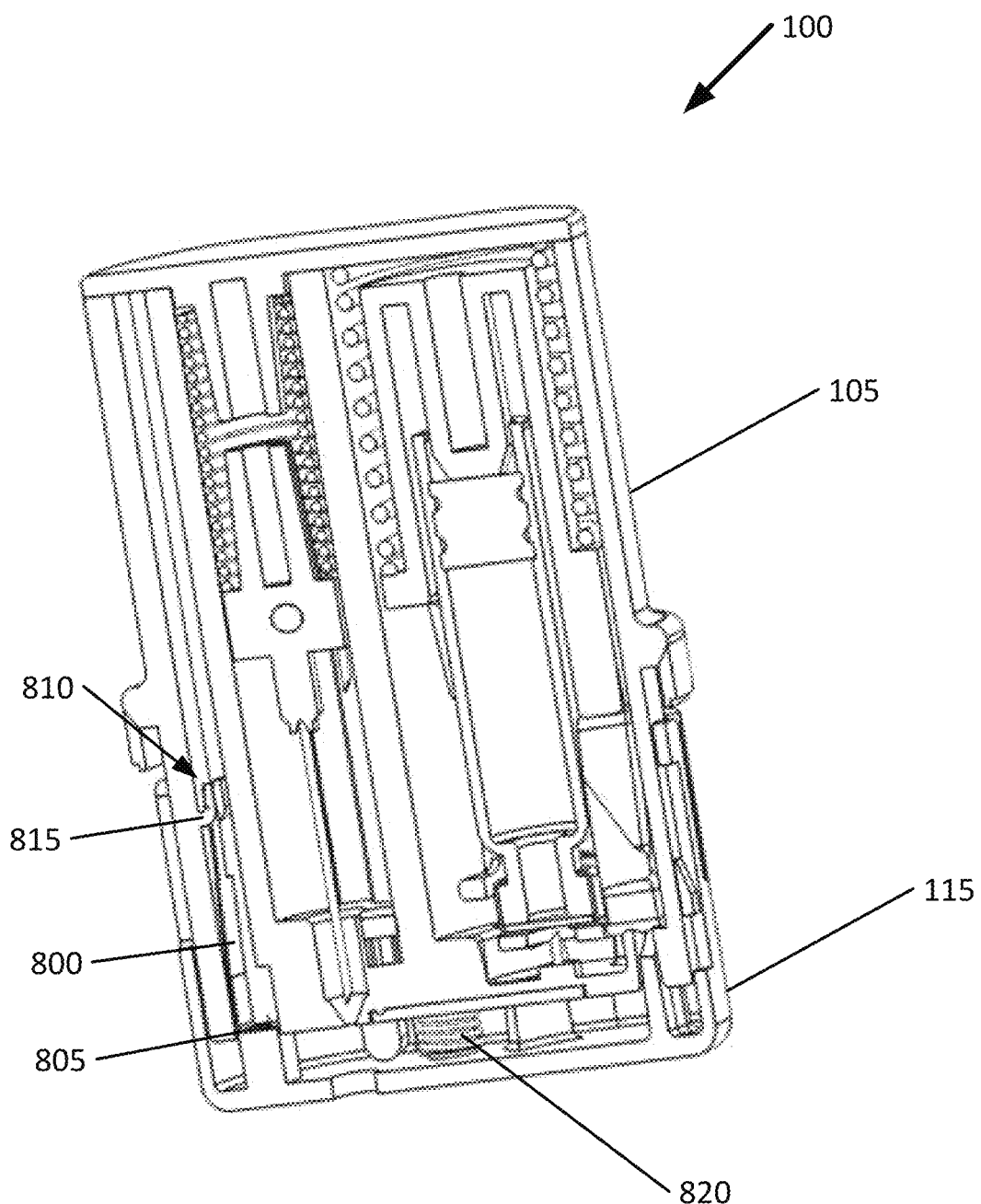
FIGS. 10C-E are cut-away views of the wearable drug delivery of FIG. 1 device with the trigger portion acting as a needle guard.
Figure 10D:
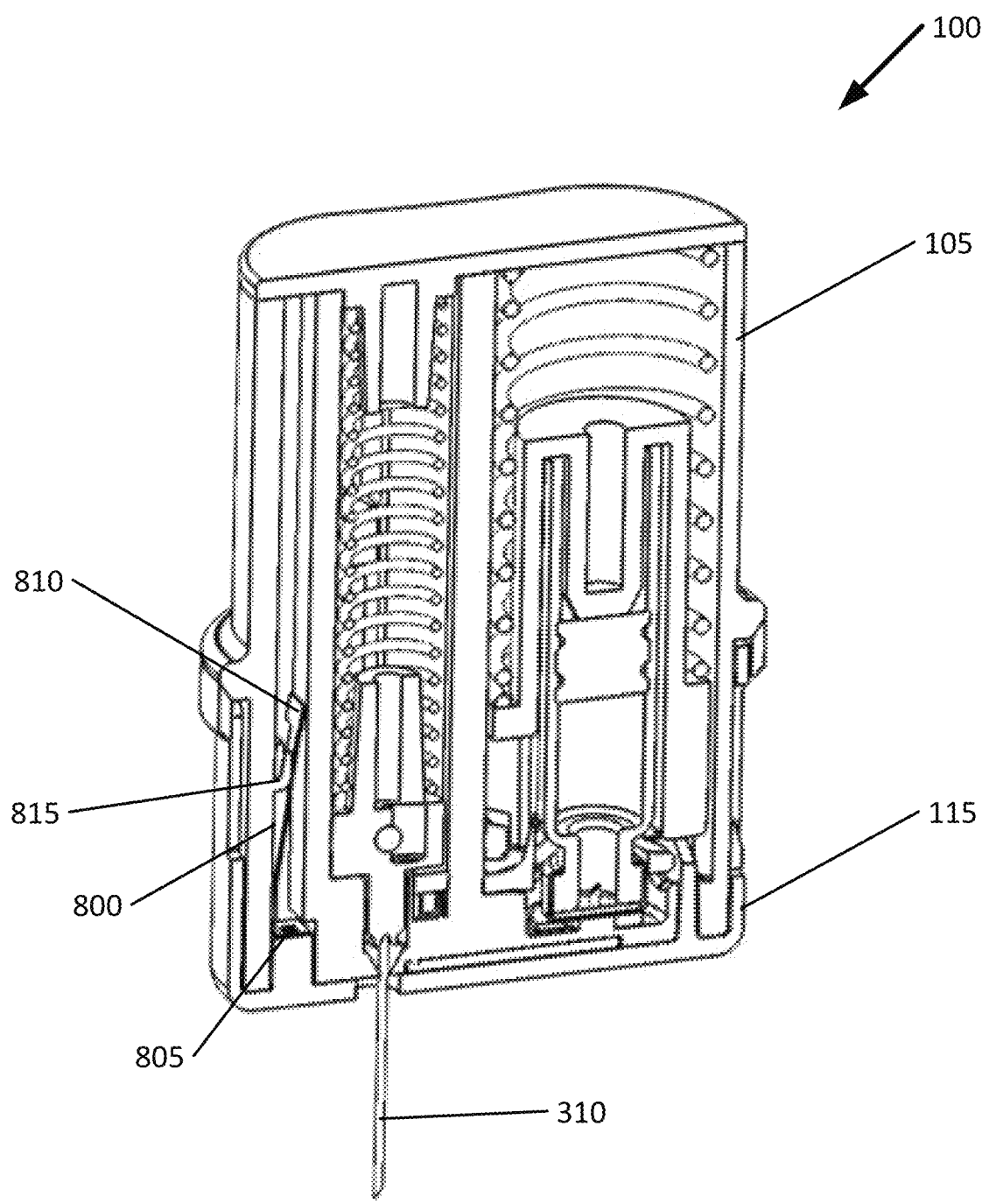

FIG. 10C shows a cross-section of the before use arrangement of the wearable drug delivery device 100 shown in FIG. 10A. A leaf spring 800 prevents the trigger portion 115 from advancing away from the handheld portion 105. The leaf spring 800 has a fixed end 805 attached to the trigger portion 115. As best seen in FIG. 10D, the leaf spring 800 further has a free end 810 opposite the fixed end 805.

During assembly of the wearable drug delivery device 100, the leaf spring 800 is bent into the configuration shown and the free end 810 engages one or more hooks 815 on the handheld portion 105. A return spring 820 sandwiched between the handheld portion 105 and trigger portion 115 supplies a force urging (separating) the handheld portion 105 and the trigger portion 115 apart. This force enhances the latching of the leaf spring 800 and inhibits the leaf spring 800 from becoming accidently disengaged from the hooks 815.

FIG. 10D shows during the use of the wearable drug delivery device 100, when the trigger portion 115 is pushed down (i.e., brought towards the handheld portion 105) the leaf spring 800 moves upward relative to the handheld portion 105 and the free end 810 disengages from the hooks 815. The leaf spring 800 returns back to its natural shape as shown. With the trigger portion 115 in this position, the needle 310 is exposed and extends beyond the trigger portion 115.

Figure 10E:
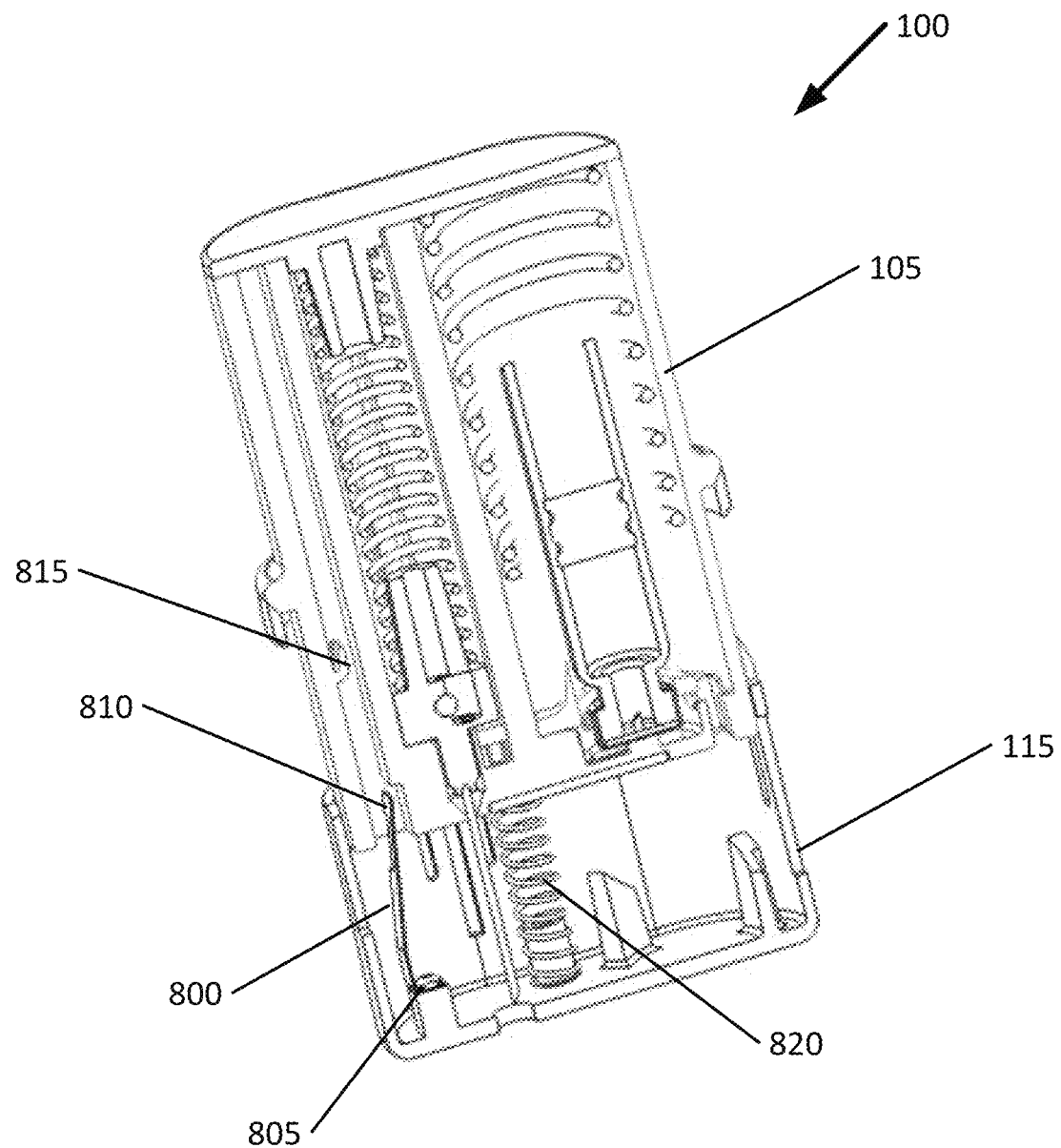

FIG. 10E shows a cross-section of the after use arrangement of the wearable drug delivery device 100 shown in FIG. 10B. When the user removes the downward force from the device 100, the return spring 820 moves the trigger portion 115 away from the handheld portion 105. In this position, referred to as the "guard position" for ease of reference, the trigger portion 115 covers the needle 310. The trigger portion 115 can be maintained in the guard position using one or more of "lock-out" features described immediately below.

Figure 11A:
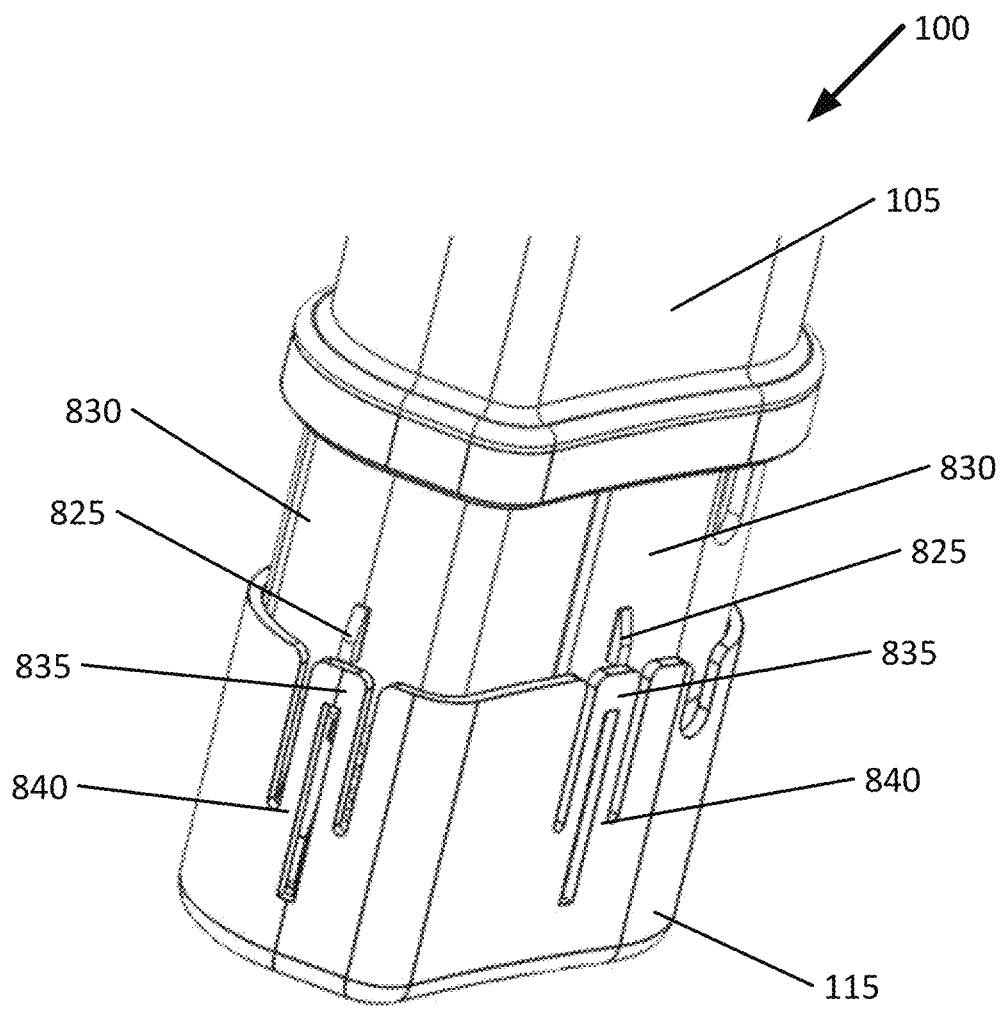
FIGS. 11A-C are views of example lockout features of the wearable drug delivery device of FIG. 1 that inhibit the needle from being re-exposed.

FIG. 11A shows one-way barbs 825 projecting from an exterior surface 830 of the handheld portion 105. The trigger portion 115 includes snap features 835. The snap features 835 are joined to the trigger portion 115 by virtual hinges 840. While the trigger portion 115 advances downward away from the handheld portion 105, the snap features 835 ride over the one-way barbs 825 and flex about the virtual hinges 840 away from the exterior surface 830. The one-way barbs 825 and snap features 835 prevent the trigger portion 115 from moving back towards the handheld portion 105 and re-exposing the needle.

Figure 11B:
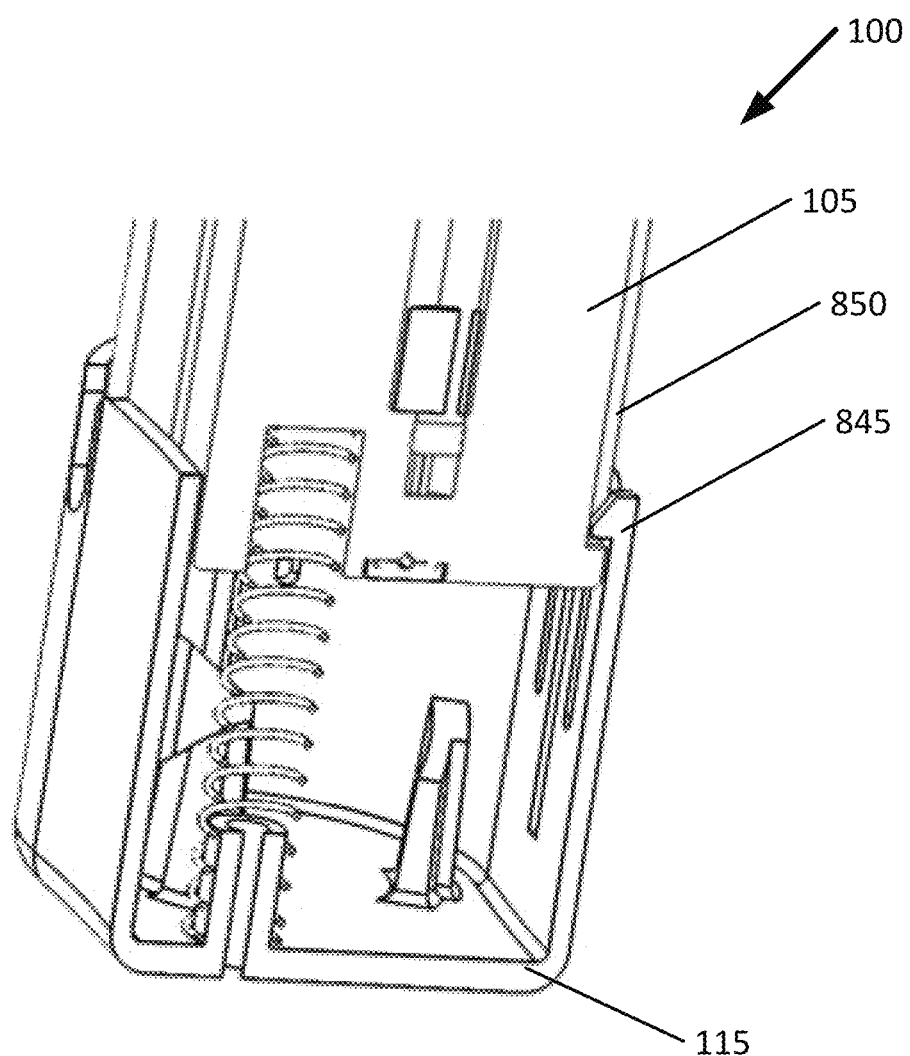

FIG. 11B shows the trigger portion 115 with one-way teeth 845 (one shown) that ride in slots 850 (one shown) in the handheld portion 105. The shapes of the one-way teeth 845 and the slots 850 inhibit the trigger portion 115 from coming off the handheld portion 105 (i.e., being disassembled) and re-exposing the needle. At the same time, the shapes allow the wearable drug delivery device 100 to be readily assembled from the handheld portion 105 and trigger portion 115.

Figure 11C:
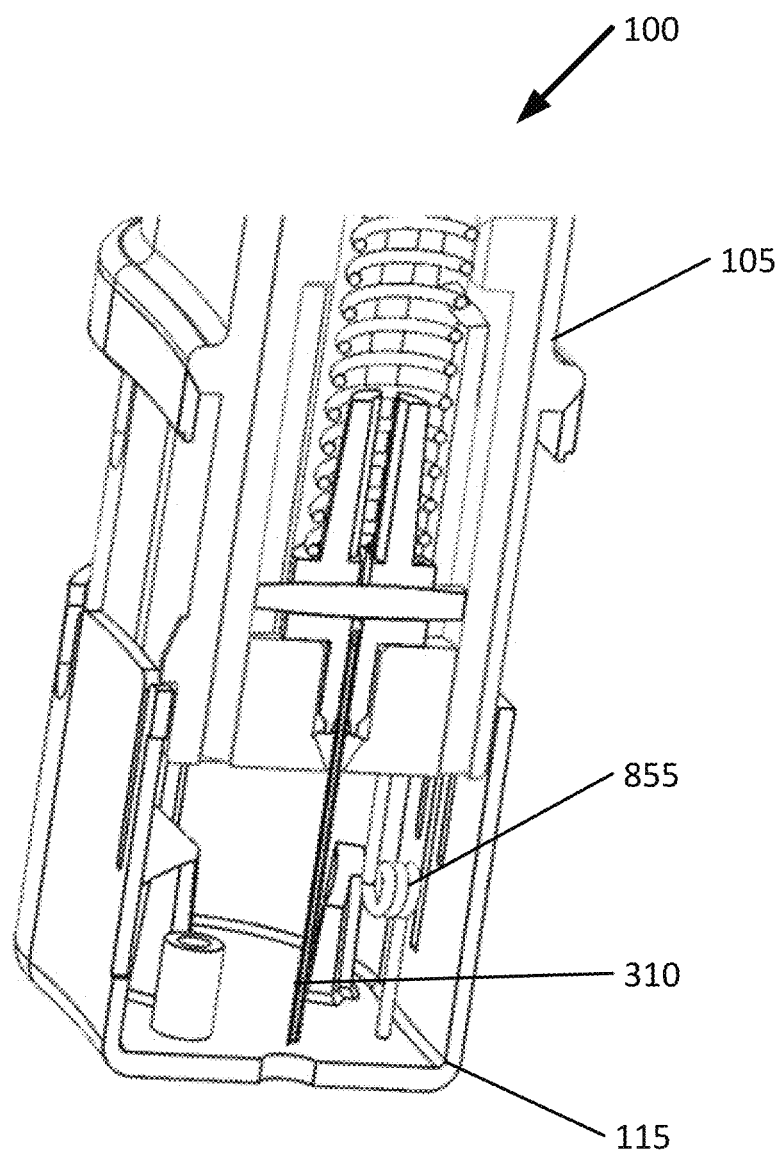

FIG. 11C shows a return spring 855 being a torsion spring. When the return spring 855 is in the opened position as shown, the return spring 855 inhibits the trigger portion 115 from moving back towards the handheld portion 105 and re-exposing the needle 310.

Figure 12A:
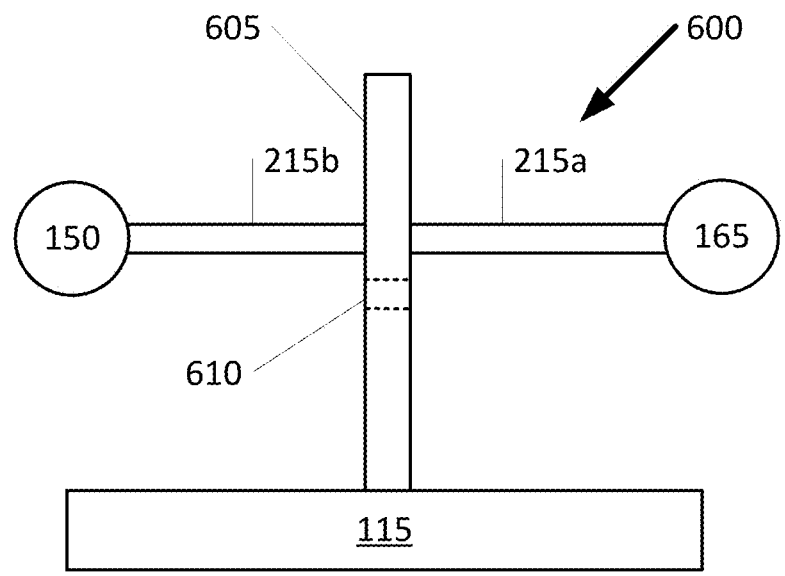
FIGS. 12A and 12B are views of an example gate of the wearable drug delivery device of FIG. 1.

FIG. 12A shows an example gate 600 for enabling the drug to flow from the drug vial 165 to the needle assembly 150 (represented diagrammatically in the figure as circles for clarity). The gate 600 includes a planar member 605 extending from the trigger portion 115 towards the handheld portion (not shown in the figure for clarity). The planar member 605 divides the channel into an upper channel portion 215a and a lower channel portion 215b.

The gate 600 further includes an opening 610 through the planer member 605. The planar member 605 moves in the direction of the longitudinal axis 125 in between the upper and lower channel portions 215a and 215b consistent with the movement of the trigger portion 115. When the trigger portion 115 is not depressed or partly depressed, the opening 610 is not aligned with the upper and lower channel portions 215a and 215b, as shown in the figure, and the planer member 605 obstructs the channel. With the gate 600 in this "closed" position, the drug cannot flow between the drug vial 165 and the needle assembly 150.

Figure 12B:
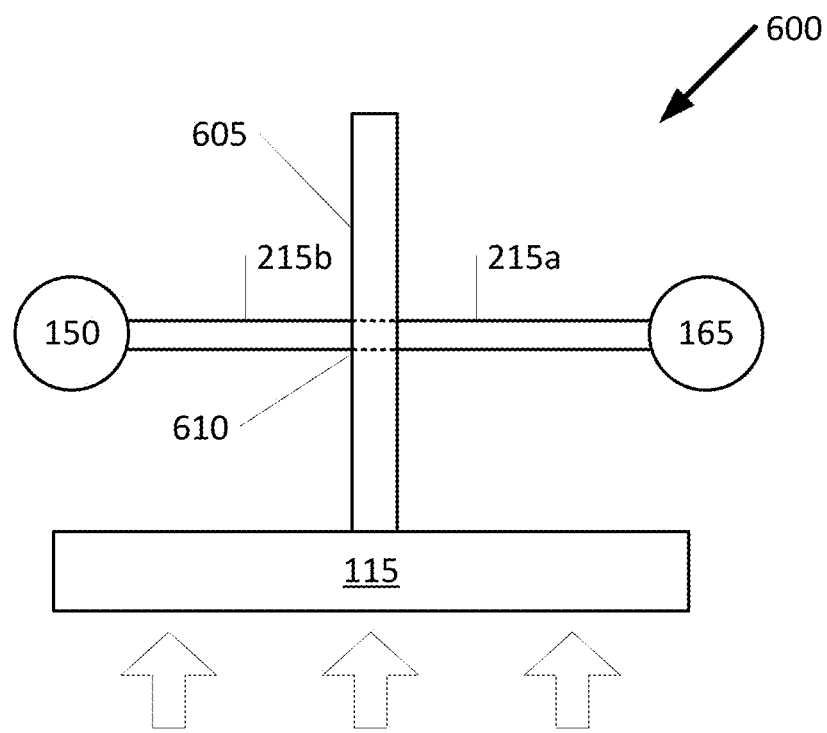

In FIG. 12B, when the user triggers the wearable drug delivery device and fully depresses the trigger portion 115, the gate 600 moves upward towards the handheld portion and the opening 610 is aligned with the upper and lower channel portions 215a and 215b as shown. With the gate 600 in this "open" position the upper and lower channel portions 215a and 215b are in fluid communication and the channel is generally unobstructed. This allows the drug to flow from the drug vial 165 to the needle assembly 150. The gate 600 is particularly advantage because the single act of triggering the wearable drug delivery device has the added function of enabling drug flow.

Figure 13:
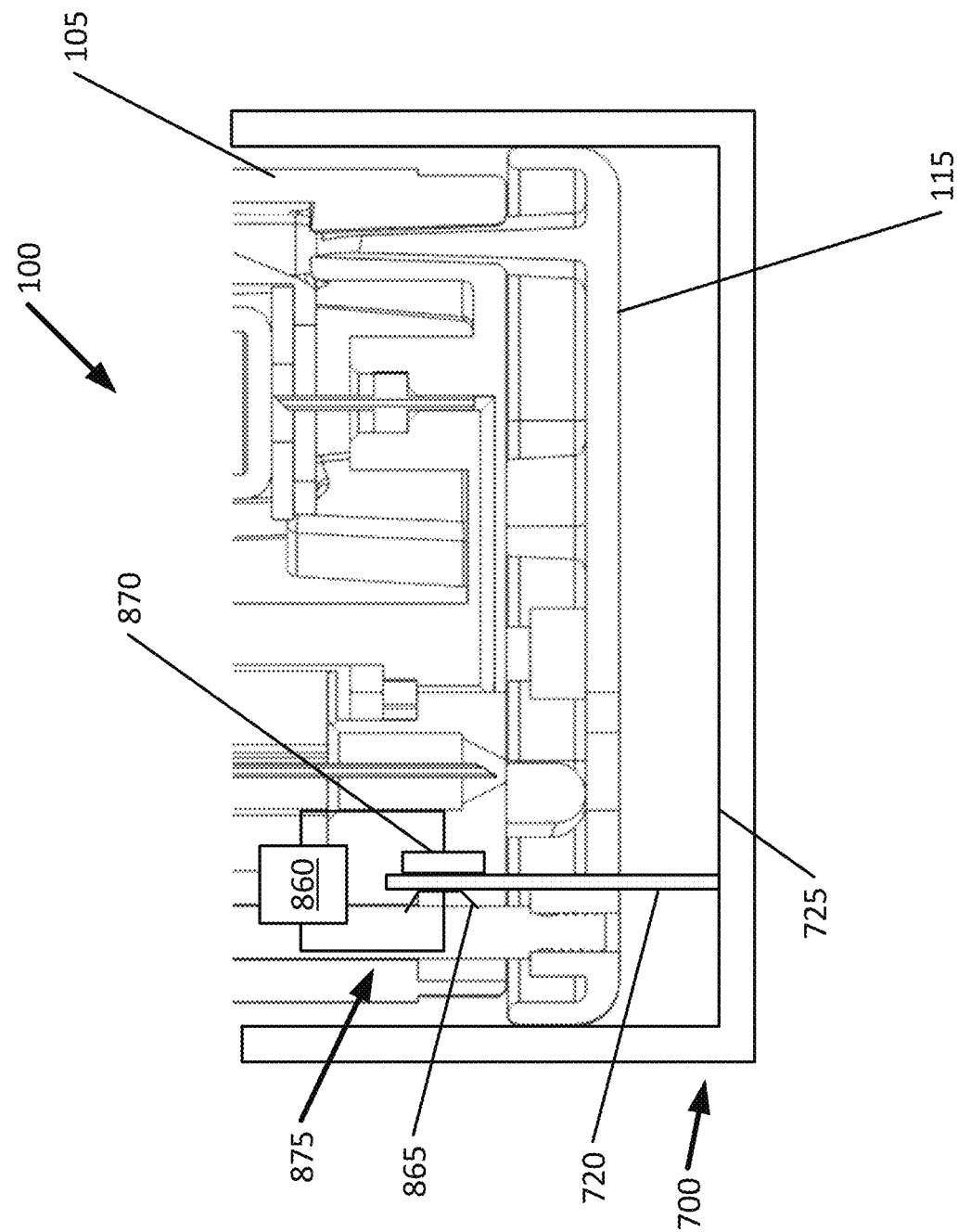
FIG. 13 is a cut-away view of the wearable drug delivery device of FIG. 1 with a mechanism for activating electronics.

FIG. 13 shows another example of the safety guard 700 including a tooth 720 for controlling electronics 860, such as a communication module, housed within the handheld portion 105. The tooth 720 extends from an interior surface 725 of the safety guard 700. When the safety guard 700 is on the wearable drug delivery device 100, the tooth 720 extends into the handheld portion 105 through a slot. Inside, the tooth 720 is positioned between an electrical contact 865 and a battery 870. The electrical contact 865 and battery 870 are electrically coupled to the electronics 860 to form an electronic circuit 875.

The tooth 720 is made from nonconductive material, such as plastic. (Some examples of the safety guard 700 are made from one material, in which case, the safety guard 700 is nonconductive). Consequently, positioning the tooth 720 between the electrical contact 865 and battery 870 creates a discontinuity in the electronic circuit 875 and the electronics 860 is inactive. The tooth feature is also advantageous because it reduces the loss of battery power over time, which in turn increases the shelf life of the wearable drug delivery device 100.

When the safety guard 700 is removed from the wearable drug delivery device 100 (e.g., to activate the wearable drug delivery device 100), the tooth 720 is pulled out the handheld portion 105 allowing the electrical contact 865 and the battery 870 to connect. This completes the electrical circuit 875 and activates the electronics 860. This arrangement is particularly advantageous because both the wearable drug delivery device 100 and the electronics 860 can be activated at the same time with one action. Additional, no additional electronic component like a switch is required to control the electronics 860, making the electronic circuit 875 simpler, less costly, and more reliable.

As just described, the electronics 860 can be a communication module. The communication module can provide information to the user when they activate the wearable drug delivery device (e.g., when they remove the safety guard 700). For example, speakers built into the wearable drug delivery device 100 play an audio recording of how to use the device when the user activates the device. It is understood that is beneficial to provide instructions to the user as the user is carrying them out.

Figure 14:
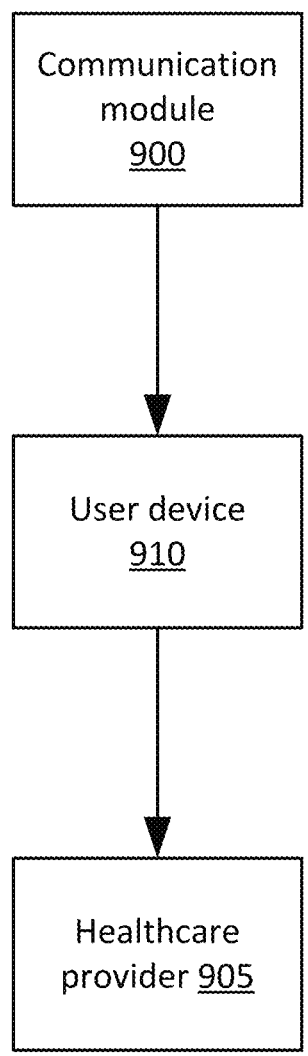
FIG. 14 is block diagram of an example communication module of the wearable drug delivery device of FIG. 1.

In FIG. 14, another example of the communication module 900 can provide information to a healthcare provider 905, wirelessly, using cellular, WI-FI, BLUETOOTH, Z-WAVE, and ZIGBEE—just to name a few wireless communication protocols. In examples using short range wireless, such as the CC2640 SIMPLELINK BLUETOOTH Wireless Micro Controller Unit by TEXAS INSTRUMENTS, the communication module 900 can be wirelessly coupled (networked) to a user device 910, such as a smartphone. The user device 910, in turn, connects to a healthcare provider 905 and relays the information. This can be accomplished using an application running on the user device 910. Advantageously, the healthcare provider 905 is notified whenever the user activates the wearable drug delivery device, thus adding safety to the device.

A challenge to using an autoinjector to self-administer a drug dose is making sure that the autoinjector needle penetrates the body to a proper depth for delivering the drug. Delivering the drug dose too shallow in the body can reduce the effectiveness of the drug dose or worst yet not, the drug dose has no effect. The present invention addresses this challenge with a dose confirmation module for determining whether a needle has reached a proper depth based on impedance. Impedance changes the deeper the needle goes into conductive tissue, such as skin, fat, and muscle. This is because increased contact with the conductive material changes the overall impedance. The dose confirmation module then notifies a user or healthcare provider whether the proper depth has been reached.

In FIG. 15A, wearable drug delivery device 100 includes a dose confirmation module 1000 electrically coupled to needle 1005 (shown in the extended position) and a conductor 1010. With the needle 1005 and conductor 1010 in air, as shown in the figure, the dose confirmation module 1000 measures an impedance of >1,000 ohm (open circuit). In FIG. 15B, the needle 1005 is inserted into muscle (a conductive medium) and the conductor 1010 is in contact with the skin overlaying the muscle (another conductive medium) the measured impedance is about 83 ohms.

Figure 15C:
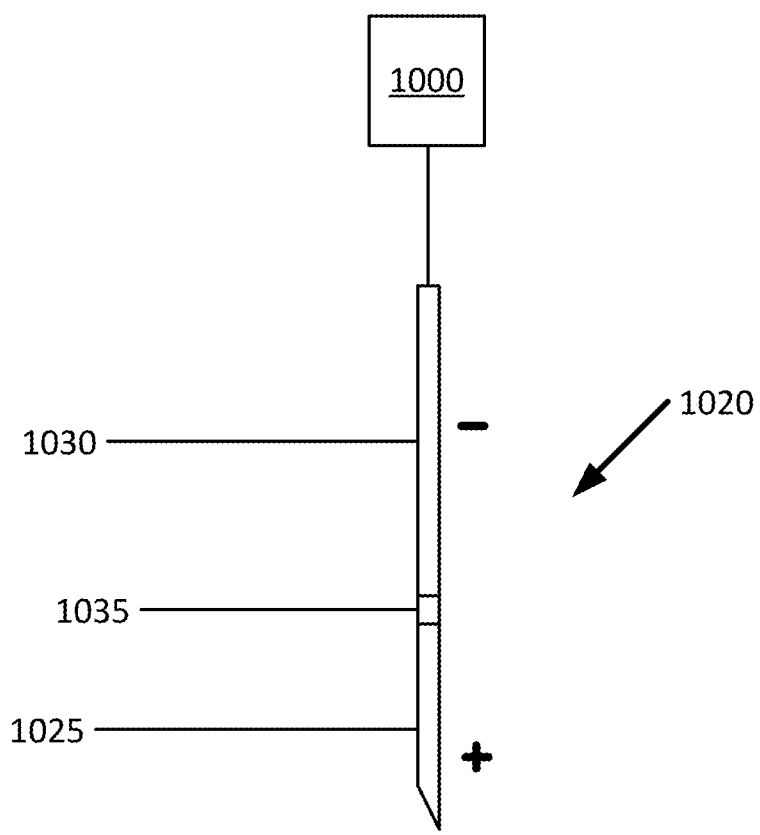

FIG. 15C shows an alternative to the needle 1005 and conductor 1010 configuration of FIG. 15A. The alternative configuration includes a combination needle 1020 having a positive distal region 1025 isolated from a negative proximal region 1030 by an insulating bushing 1035. (The polarities of the distal and proximal regions can be switched.) The combination needle 1020 is electrically coupled to the dose confirmation module 1000. With the combination needle 1020 in air, the dose confirmation module 1000 measures an impedance of >1,000 ohm (open circuit). When the combination needle 1020 penetrates the skin and underlying muscle, both the positive distal region 1025 and the negative proximal region 1030 are in conductive medium; and the dose confirmation module 1000 measures impedance less than 1,000 ohm.

The dose confirmation module 1000 compares the measured impedance to a threshold value and based on the comparison, confirms whether the needle 1005 or combination needle 1020 has reached a proper depth for delivering the drug dose. For example, if the measured impedance is less than or equal to 83 ohms, the dose confirmation module 1000 determines that the proper depth for the injection has been reached (i.e., OK). Impedance measurements greater than 83 ohms indicate that the proper depth for the injection has not been reached (i.e., NOT OK).

A dose confirmation can be communicated to the user using an audio cue (e.g., one beep for OK or two beeps for NOT OK) or a visual cue (e.g., a lit green light for OK or a lit red light for NOT OK). The dose confirmation can also be communicated to a healthcare provider using the communication module 900 described above with reference to FIG. 14. Advantageously, the foregoing examples can provide the user with immediate feedback on whether they used the wearable drug delivery device 100 correctly and/or notify a healthcare provider of the same. In some cases, the user and/or healthcare can take corrective measure based on the information.

Figure 16:
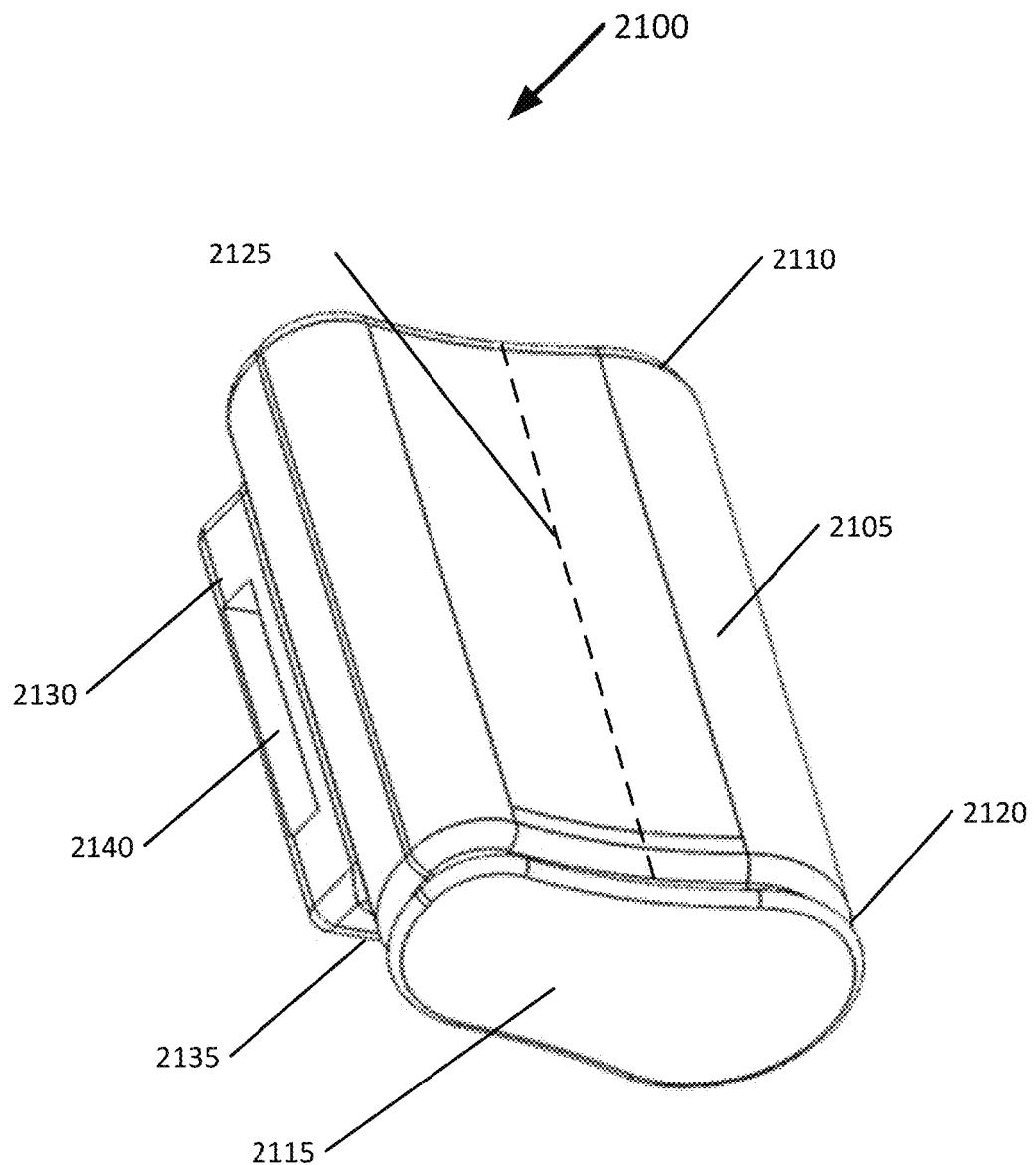
FIG. 16 is perspective view of another embodiment of a wearable drug delivery device, similar to but in some ways different than the device of FIG. 1.

FIG. 16 shows another exemplary wearable drug delivery device 2100 including a handheld portion 2105 at a proximal end 2110 and a trigger portion 2115 at a distal end 2120. A longitudinal axis 2125 extends between the proximal end 2110 and the distal end 2120. The handheld portion 2105 can be constructed of a durable material, such as stainless steel, aluminum, polycarbonate, etc., to protect the internal components of the wearable drug delivery device 2100 and/or the user of wearable drug delivery device 2100.

In the example shown in FIG. 16, the wearable drug delivery device 2100 further includes an adapter 2130 for wearing the device on the user. The adapter 2130 extends from handheld portion 2105 and terminates at a surface 2135. The surface 2135 is shaped to conform to the user's wrist, arm or other body part. For example, the surface 2135 is concaved to engage to the rounded surface the user's wrist. The point of concavity of the surface 2135 is defined by a point along an axis offset and parallel to longitudinal axis 2125.

The adapter 2130 can include a slot 2140 for receiving a band (not shown), such as an arm or wrist band, for wearing the wearable drug delivery device 2100. The wrist/arm band can be elastic or include a fastener, such as hook and loop, button or snap allowing the user to readily remove the wearable drug delivery device 2100 from their body when it's time to use the device.

Figure 17:
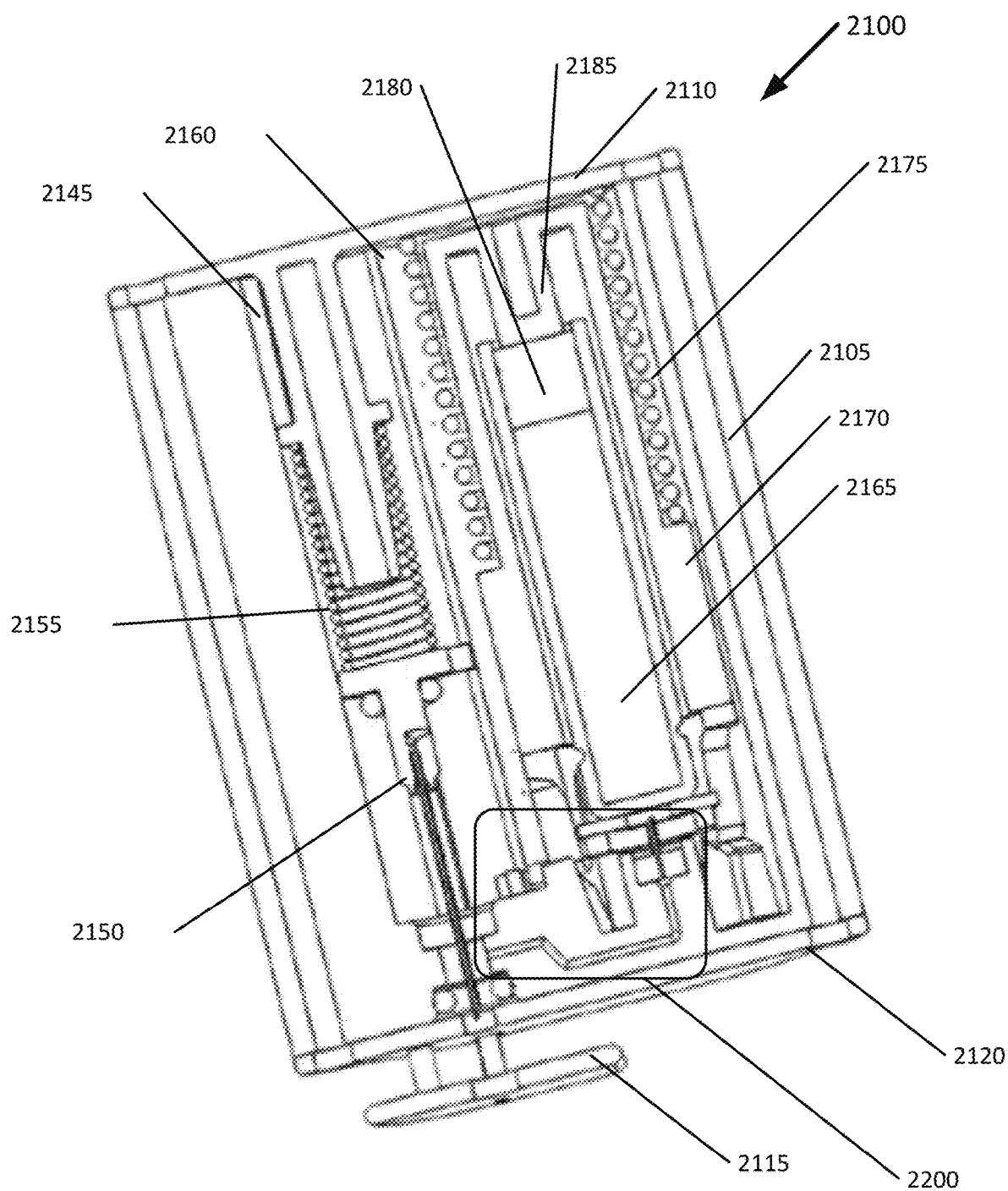
FIG. 17 is a cut-away view of the wearable drug delivery device of FIG. 16.

FIG. 17 shows the insides of the wearable drug delivery device 2100. The handheld portion 2105 is divided into two compartments that are arranged side-by-side and aligned with the longitudinal axis 2125. The first compartment 2145 contains a needle assembly 2150 and a penetrating spring 2155. As will be described in greater below, to pierce the user' skin the penetrating spring 2155 moves the needle assembly 2150 within the first compartment 2145 in the direction of the longitudinal axis 2125 from a position at the proximal end 2110 to a position at the distal end 2120. For ease of reference, the former position is called the "withdrawn position" and the latter portion is called the "extended position". Additionally, the proximal-to-distal direction is referred to as the "downward direction," and the opposite direction is the "upward direction".

The second compartment 2160 contains a drug vial 2165 surrounded by a rotator 2170, all of which are surrounded by a vial spring 2175. The concentric arrangement of these parts is advantageous because it allows the wearable drug delivery device 2100 to be short and wearable. As will be described in greater detail below, to inject the drug dose into the user, the vial spring 2175 moves the drug vial 2165 and the rotator 2170 downward within the second compartment 2160, and further moves a plunger 2180 downward within the drug vial 2165. By way of non-limiting example, the drug vial 2165 can be filled with a dose of epinephrine or insulin.

Figure 18:
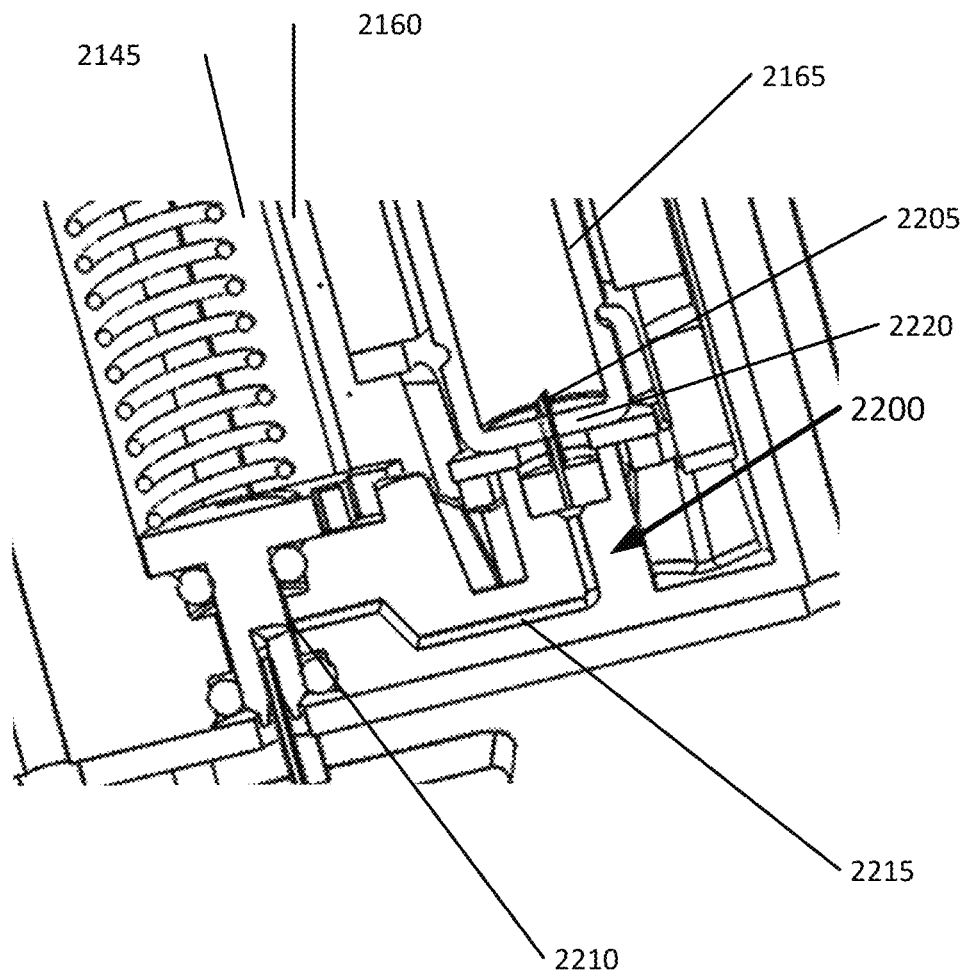
FIG. 18 is a close up view of an example integral drug delivery port of the wearable drug delivery device of FIG. 16.

The wearable drug delivery device 2100 further includes at the distal end 2120, an integral drug delivery port 2200 for providing a path for the drug dose to flow from the drug vial 2165 to the needle assembly 2150. In the close up view of FIG. 18, the integral drug delivery port 2200 extends transversely between the first compartment 2145 and the second compartment 2160. The integral drug delivery port 2200 includes a vial needle 2205 (entrance), an exit 2210, and a channel 2215 extending between them.

When the drug vial 2165 is moved in the downward direction, the vial needle 2205 encounters a vial membrane 2220, which seals the drug vial 2165. As the drug vial 2165 continues to move downward, the vial needle 2205 punctures the vial membrane 2220. At this point, the drug vial 2165 is in fluid communication with the integral drug delivery port 2200. The drug dose flows out of the drug vial 2165 through the vial needle 2205 and the channel 2215, and then out the exit 2210. The vial needle 2205 can be located above the exit 2210 to help fluid flow out of the drug vial 2165.

Figure 19A:
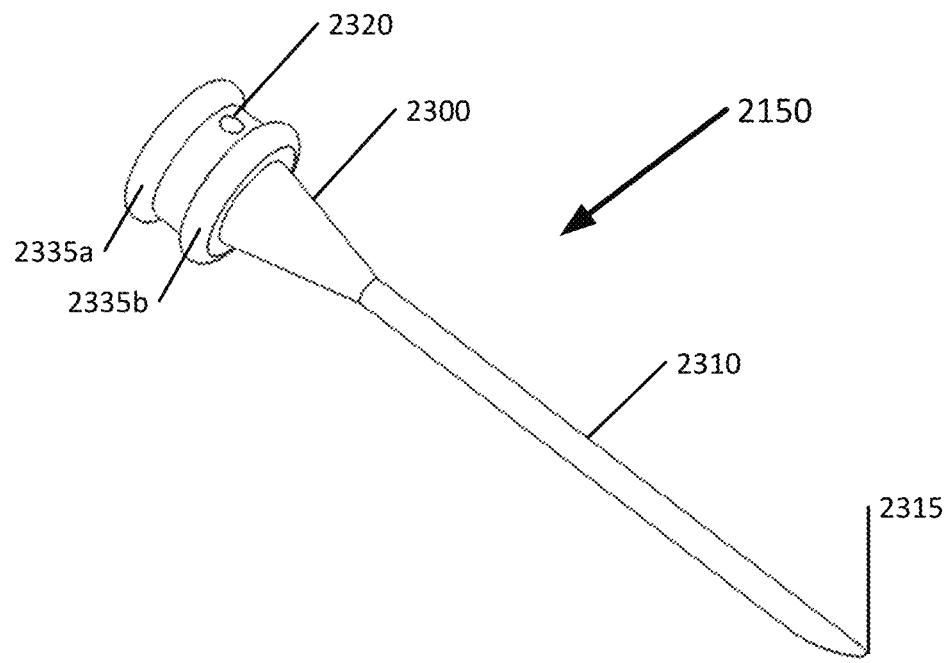
FIGS. 19A and 19B are perspective views of an example needle assembly of the wearable drug delivery device of FIG. 16.
Figure 19B:
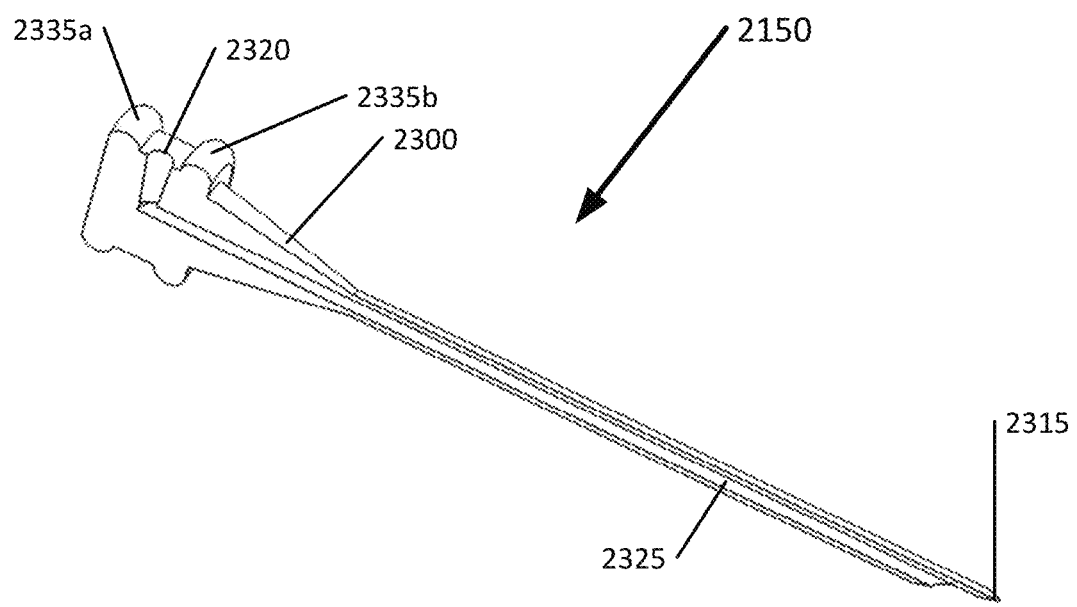

FIG. 19A shows an example of the needle assembly 2150, including a needle body 2300, a needle 2310, and a tip 2315. The needle body 2300 is the base the needle assembly 2150 and includes a needle port 2320. The needle 2310 extends from the needle body 2300 and terminates at the tip 2315. As best seen in FIG. 19B, the needle 2310 includes a central lumen 2325 extending from the tip 2315 at one end. The needle port 2320 extends radially from the other end of the central lumen 2325. Fluid entering the needle port 2320 flows through the central lumen 2325 and out of the tip 2315.

Figure 19C:
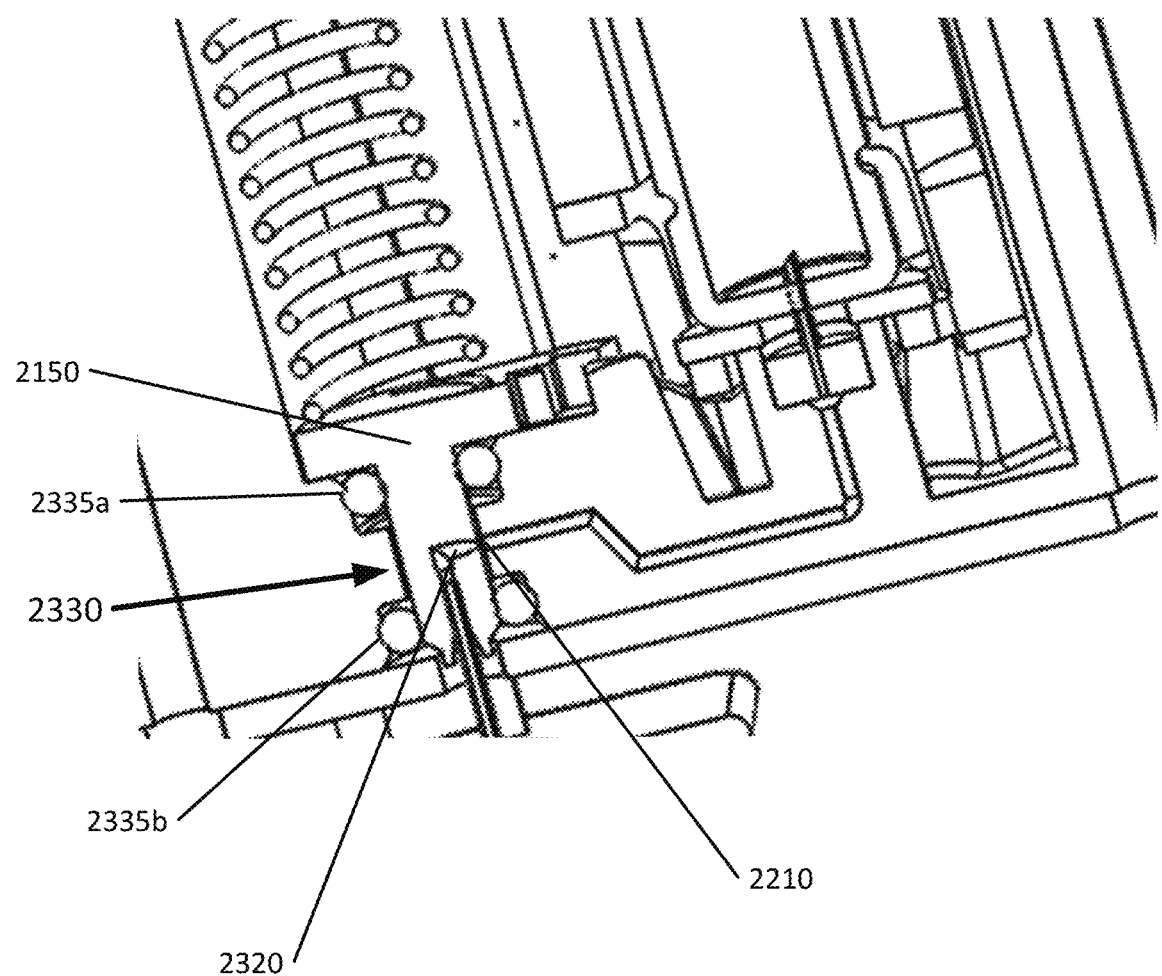
FIG. 19C is a cut-away view of the wearable drug delivery device of FIG. 16 with the needle assembly in the extended position.

FIG. 19C shows the needle assembly 2150 in the extended position within a receiving portion 2330 of the handheld portion 2105. As shown, the receiving portion 2330 has a shape complementary to the shape of the needle body 2300. The receiving portion 2330 includes an upper part, a lower part, and a shoulder connecting them. The upper part corresponds with the needle assembly needle body 2300 and includes the exit 2210 of the integral drug delivery port 2200.

With the needle assembly 2150 in the extended position, the exit 2210 of the integral drug delivery port 2200 and needle port 2320 are in fluid communication with each other. Fluid flows from the drug vial 2165 through the integral drug delivery port 2200 and the needle port 2320, and out of the needle 2310. In the examples shown, the needle assembly 2150 includes seals 2335a and 2335b above and below the needle port 2320. In the extended position, the seals 2335a and 2335b close off the upper part of the receiving portion 2330 allowing fluid entering the upper part from the exit 2210 to flow into the needle port 2320. This arrangement is advantageous because it does not require a direct connection between the needle assembly 2150 and the drug vial 2165. In some examples, the upper part may be further made leak resistant by a downward force applied from the penetration spring 2155.

Figure 20A:
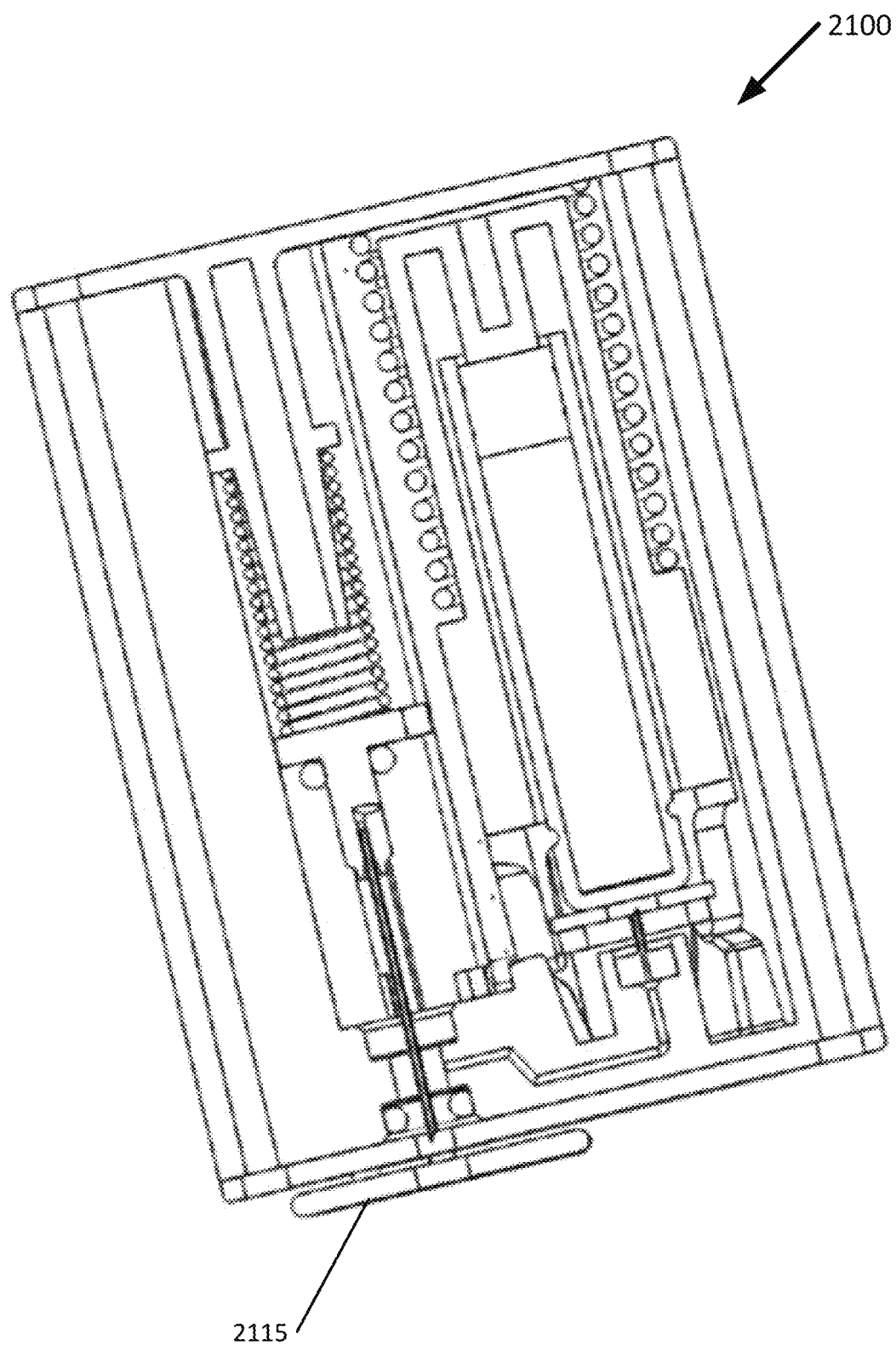
FIGS. 20A-D is a series of views of the drug delivery sequence of the wearable drug delivery device of FIG. 16.
Figure 20B:
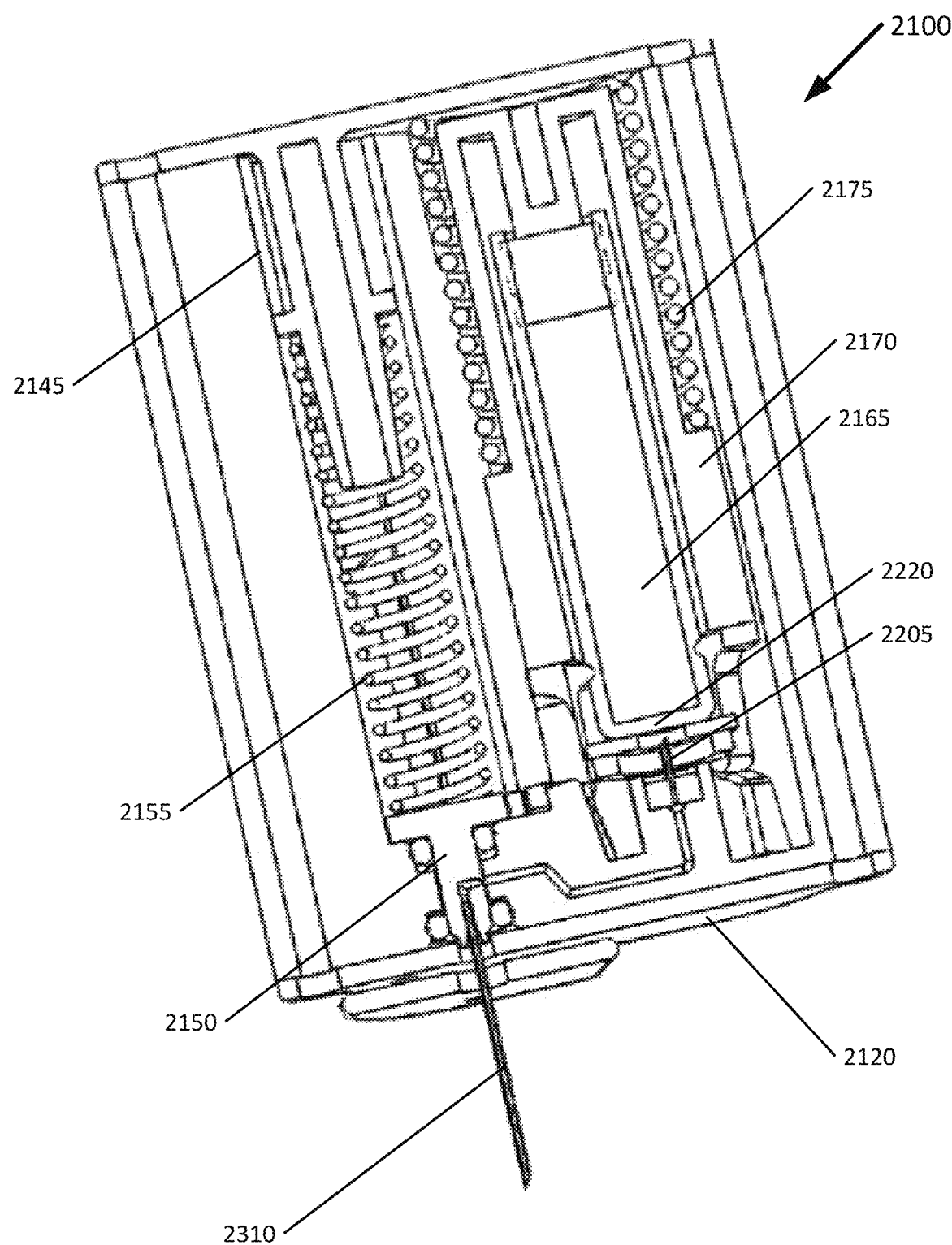

FIGS. 20A-B shows an example sequence of orchestrated events starting with a user triggering the wearable drug delivery device 2100 and ending with a drug dose delivered to the user. Starting in FIG. 20A, the user triggers the wearable drug delivery device 2100 by depressing the trigger portion 2115 against their thigh, for example. This actuates a needle trigger mechanism (described in greater detail below), which in turn releases energy stored in the penetration spring 2155.

In FIG. 20B, the penetration spring 2155 drives the needle assembly 2150 downwards within the first compartment 2145 from the withdrawn position to the extended position. In the extended position, the needle 2310 projects beyond the distal end 2120 of the wearable drug delivery device 2100 and into the user's thigh. Moving the needle assembly 2150 downward to the extended position activates a delivery trigger mechanism (described below in greater detail). This in turn releases energy stored in the vial spring 2175. As the vial spring 2175 expands, it drives the rotator and drug vial 2165 downward where the vial needle 2205 meets the vial membrane 2220.

Figure 20C:
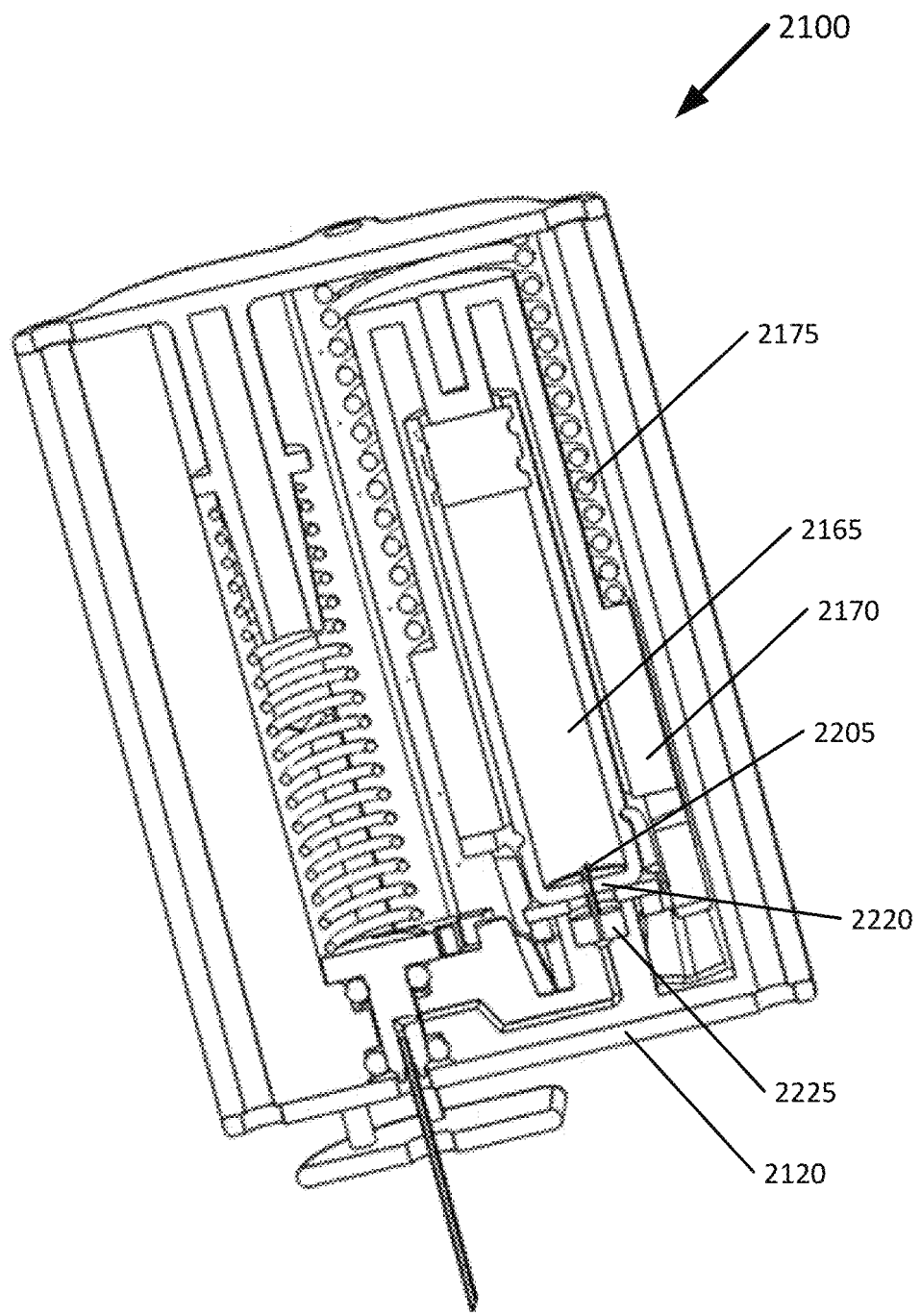

In FIG. 20C, the rotator 2170 and the drug vial 2165 continue moving downward until the vial needle 2205 punctures the vial membrane 2220. The drug vial 2165 continues to move downward until a stop 2225 extending up from the distal end 2120 prevents the drug vial 2165 from moving further downward. At this point, the vial spring 2175 is not yet fully extended and still has more travel left.

Figure 20D:
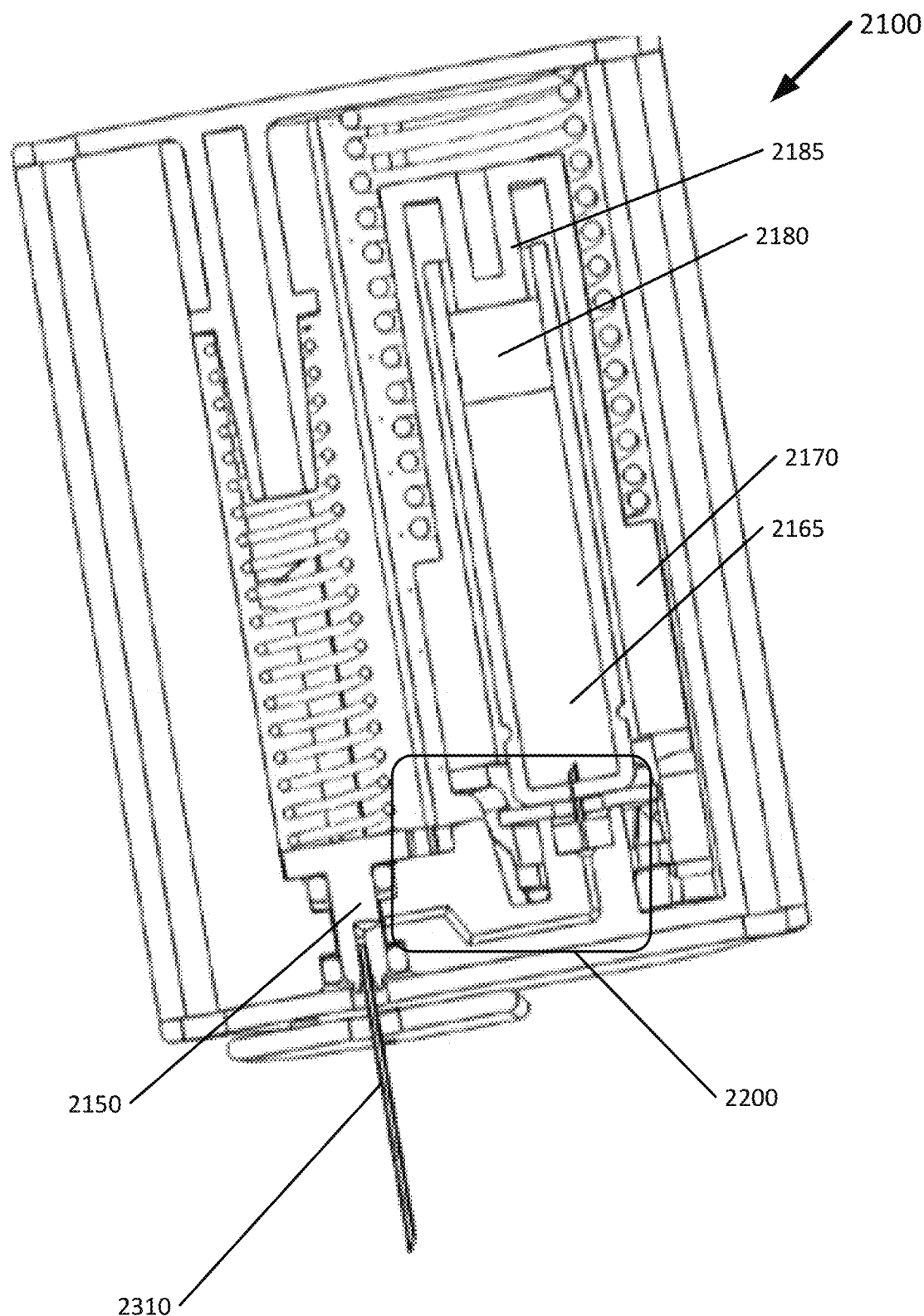

In FIG. 20D, the rotator 2170 includes a piston 2185 at one end that abuts the plunger 2180 within the drug vial 2165. As the vial spring 2175 continues to push the rotator 2170 downward, the piston 2185 drives the plunger 2180 downward within the drug vial 2165 expelling the drug dose from the drug vial 2165. The expelled drug dose flows through the integral drug delivery port 2200 and needle assembly 2150, out the needle 2310, and into the user's thigh.

Figure 21A:
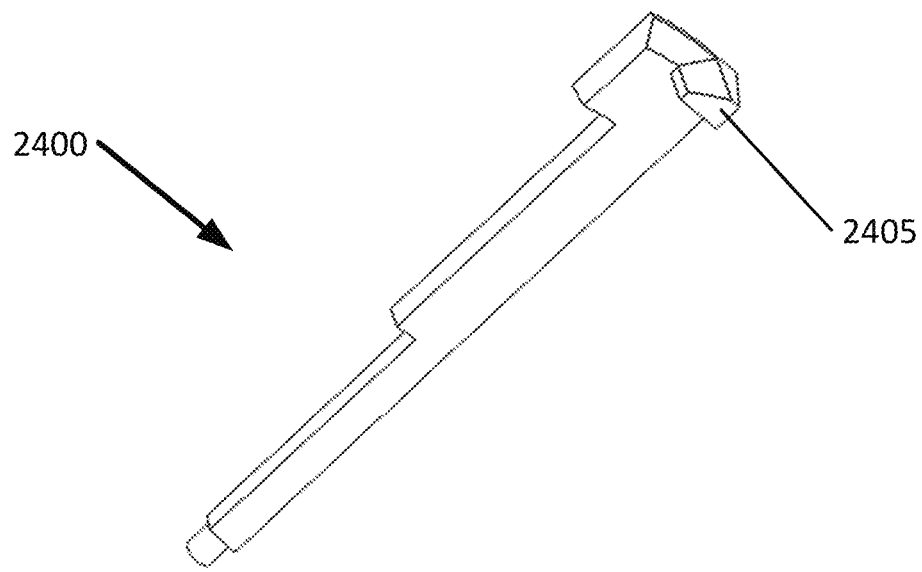
FIGS. 21A and 21B are perspective views of an example trigger arm and an example needle body of the wearable drug delivery device of FIG. 16.

Turning now to detailed discussion of the needle trigger mechanism, the mechanism operates via the trigger portion 2115, which contacts the user's target injection area (e.g., thigh). The trigger portion 2115 includes one or more trigger arms 2400 (e.g., two trigger arms) shown in FIG. 21A that extend into the handheld portion 2105. When the user pushes down on the trigger portion 2115, the trigger arm 2400 moves upward within the handheld portion 2105.

Figure 21B:
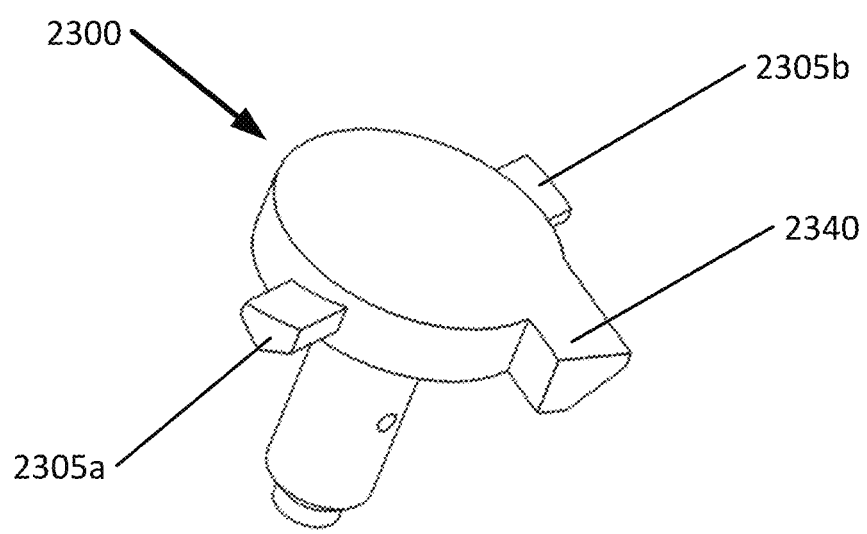

A support pad 2405 on the trigger arm 2400 normally supports the spring loaded needle assembly 2150. The needle body 2300 includes one or more ears 2305 each normally supported by a trigger arm support pad. The example needle body 2300 shown in FIG. 21B includes two ears 2305a and 2305b spaced 180° apart, which corresponds to a similar arrangement trigger arms. The needle body 2300 further includes an arm 2340, which is used for the delivery trigger mechanism described below.

Figure 21C:
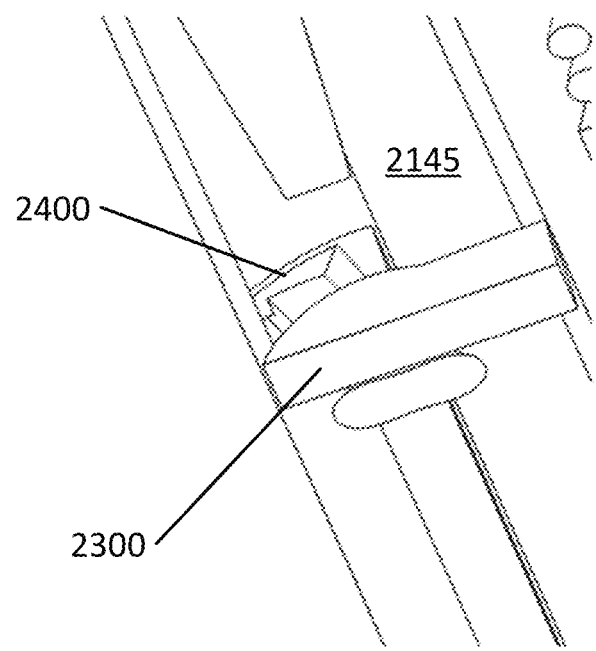
Figure 216D:
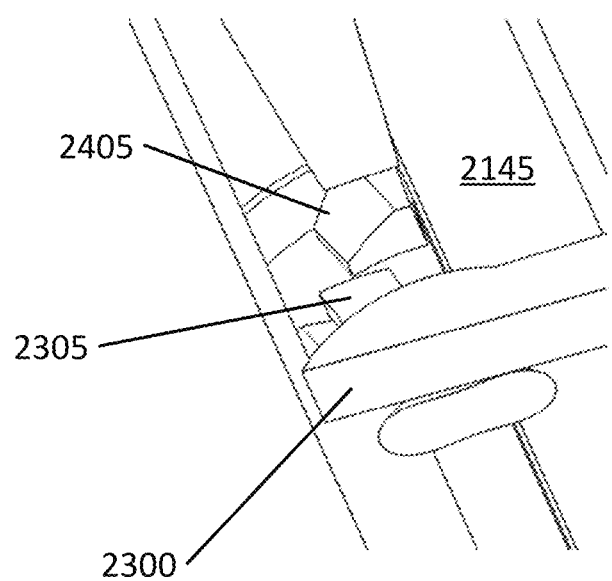
Figure 21E:
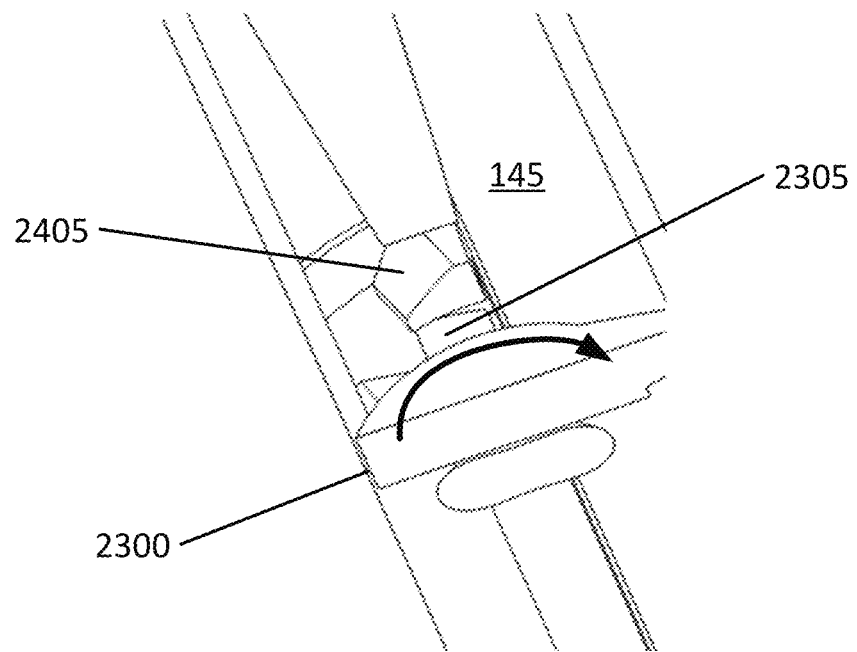
Figure 21F:
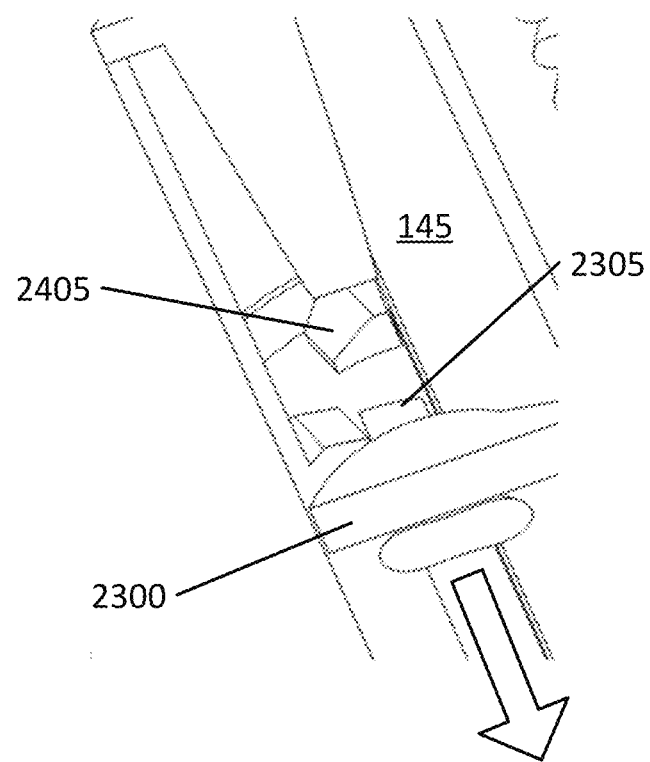

The support pad 2405 and ear 2305 can each have an angled surface that facilitates cooperation between the needle body 2300 and the trigger arm 2400. As the trigger arm 2400 is moved upward by the trigger portion 2115, the angled surfaces cause the needle body 2300 to lift and rotate away from the trigger arm support pad 2405, as seen in FIG. 21C. Once the trigger arm support pad 2405 reaches a trigger point, as seen in FIG. 21D, the needle body 2300 can rotate underneath the trigger arm support pad 2405, as seen in FIG. 21E. No longer supported, the needle assembly 2150 can then travel freely downward towards the target injection site, as seen in FIG. 21F.

Figure 22A:
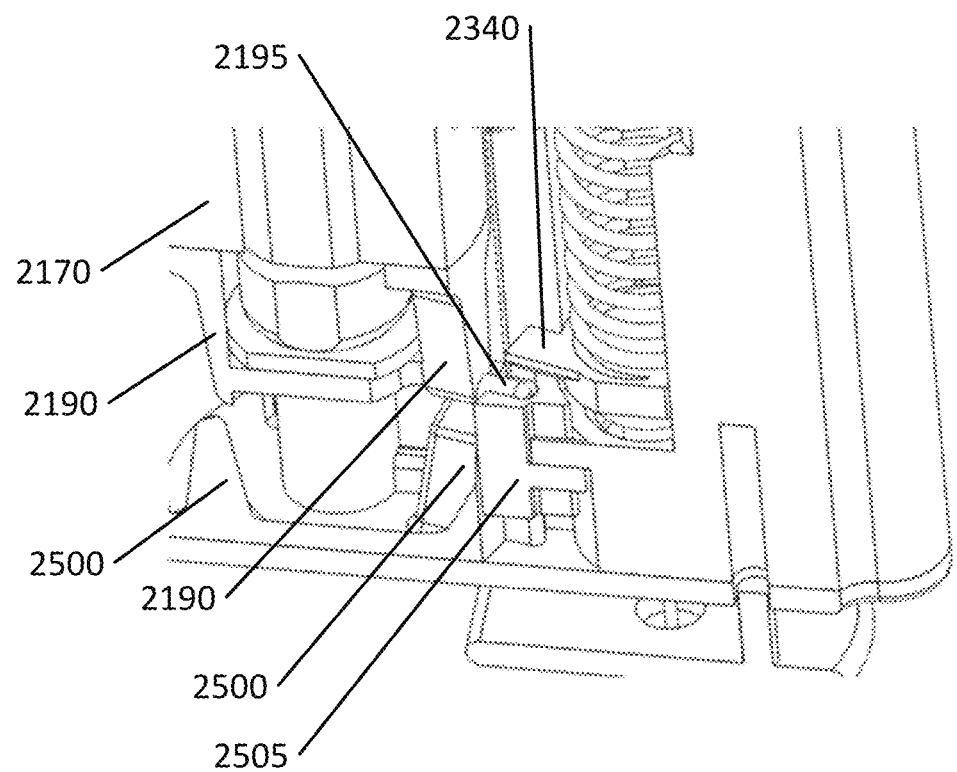
FIGS. 22A and 22B are a series of views of a delivery trigger mechanism sequence of the wearable drug delivery device of FIG. 16.
Figure 22B:
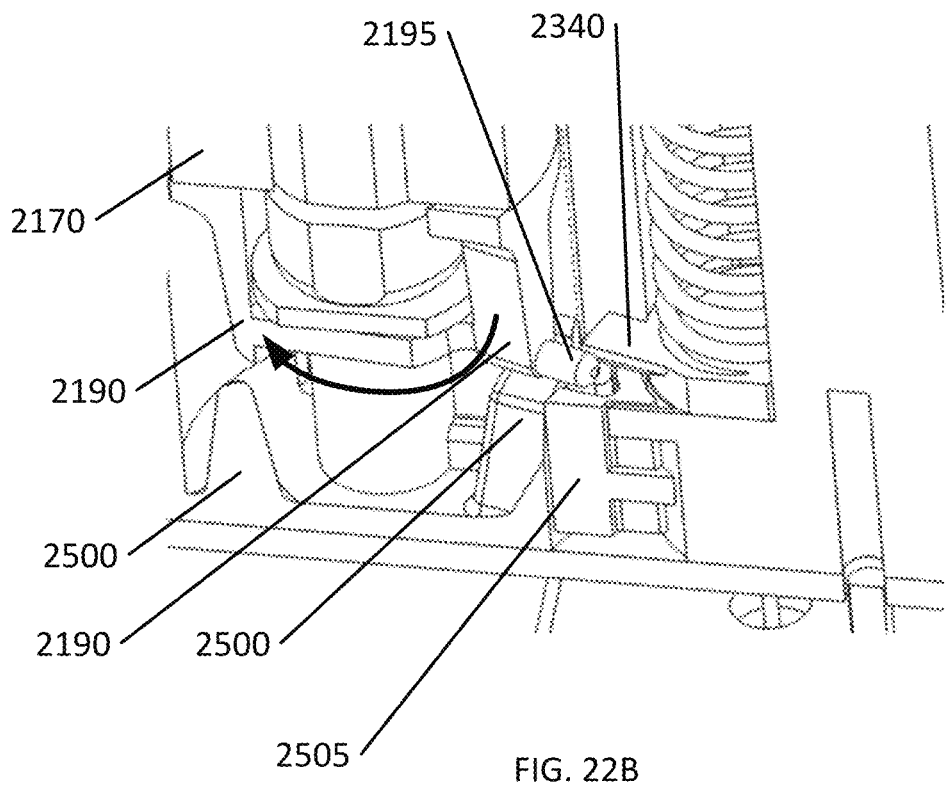

FIGS. 22A and 22B show an example of the delivery trigger mechanism mentioned above. The rotator 2170 includes a pair of legs 2190 at the end opposite the piston 2185. The legs 2190 rest on a pair of corresponding yokes 2500 extending from the distal end of the handheld portion 2105. The yokes 2500 resist downward movement by the rotator 2170 but their shape encourages the rotator 2170 to turn. As shown in FIG. 22A, a latch 2505 in cooperation with a pin 2195 projecting from the one of the legs 2190 resists this rotational movement.

In FIG. 22B, as the needle assembly 2150 reaches the extended position; the arm 2340 projecting from then needle assembly 2150 pushes the latch 2505 downward. With the latch 2505 down and the pin 2195 free, the rotator 2170 revolves off of the yokes 2500 (represented in the figure as a curved arrow), enabling the vial spring 2175 to drive the rotator 2170 and drug vial 2165 downward as described above.

Figure 23A:
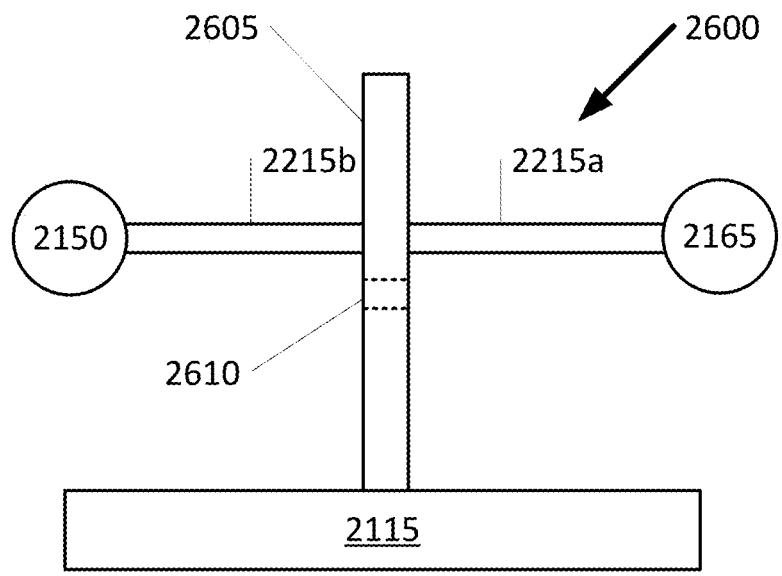
FIGS. 23A and 23B are views of an example gate of the wearable drug delivery device of FIG. 16.

FIG. 23A shows an example gate 2600 for enabling the drug to flow from the drug vial 2165 to the needle assembly 2150 (represented diagrammatically in the figure as circles for clarity). The gate 2600 includes a planar member 2605 extending from the trigger portion 2115 towards the handheld portion (not shown in the figure for clarity). The planar member 2605 divides the channel into an upper channel portion 2215a and a lower channel portion 2215b.

The gate 2600 further includes an opening 2610 through the planer member 2605. The planar member 2605 moves in the direction of the longitudinal axis 2125 in between the upper and lower channel portions 2215a and 2215b consistent with the movement of the trigger portion 2115. When the trigger portion 2115 is not depressed or partly depressed, the opening 2610 is not aligned with the upper and lower channel portions 2215a and 2215b, as shown in the figure, and the planer member 2605 obstructs the channel. With the gate 2600 in this "closed" position, the drug cannot flow between the drug vial 2165 and the needle assembly 2150.

Figure 23B:
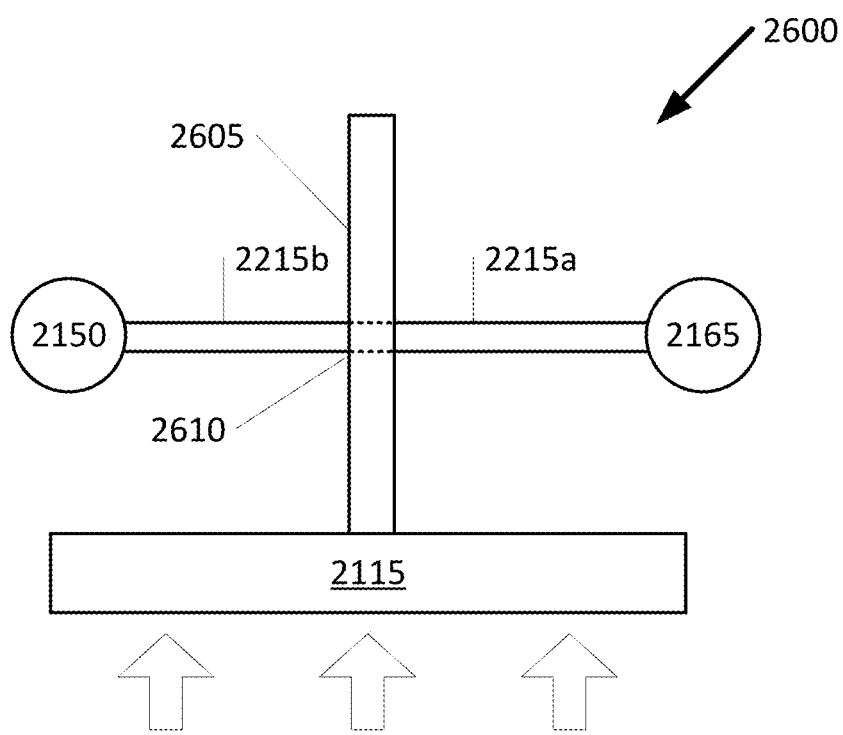

In FIG. 23B, when the user triggers the wearable drug delivery device and fully depresses the trigger portion 2115, the gate 2600 moves upward towards the handheld portion and the opening 2610 is aligned with the upper and lower channel portions 2215a and 2215b as shown. With the gate 2600 in this "open" position the upper and lower channel portions 2215a and 2215b are in fluid communication and the channel is generally unobstructed. This allows the drug to flow from the drug vial 2165 to the needle assembly 2150. The gate 2600 is particularly advantage because the single act of triggering the wearable drug delivery device has the added function of enabling drug flow.

Figure 24A:
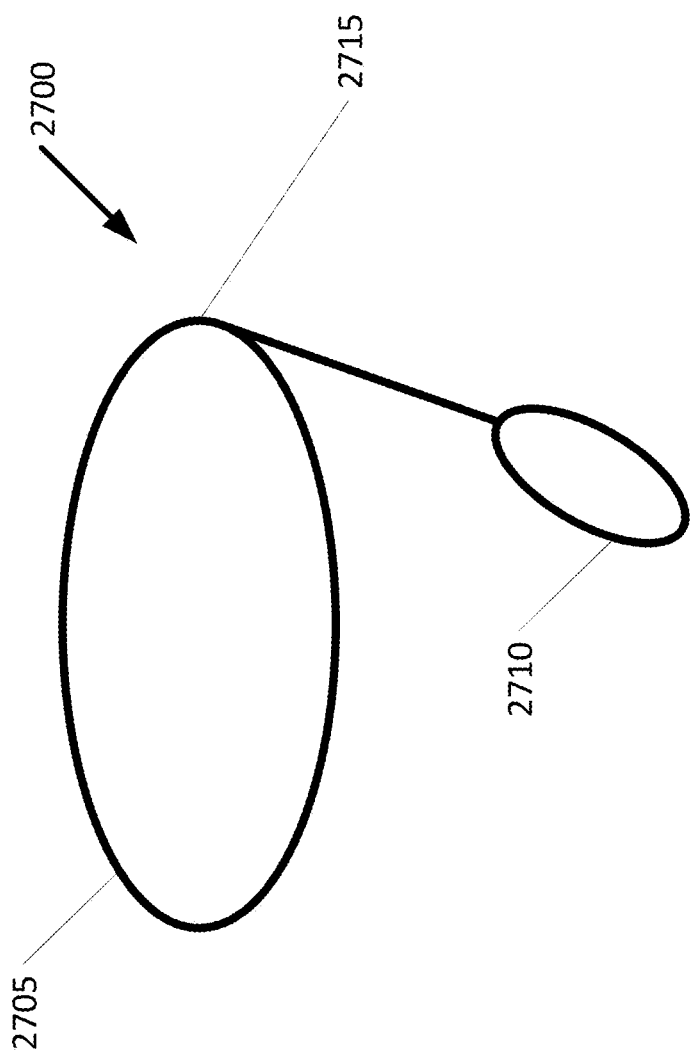
FIG. 24A is a diagram of an example trigger guard of the wearable drug delivery device of FIG. 16.
Figure 24B:
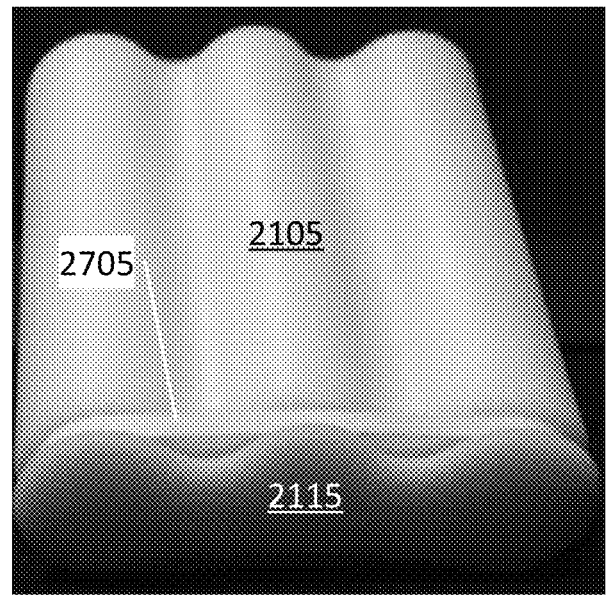
FIGS. 24B-E is a series of views showing the trigger guard being removed from the wearable drug delivery device of FIG. 16.

FIG. 24A shows an example trigger guard 2700 for preventing the wearable drug delivery device from being triggered, inadvertently. The trigger guard 2700 includes a separation strip 2705 that fits in a gap between the handheld portion 2105 and the trigger portion 2115, as shown in FIG. 24B. When the trigger portion 2115 is depressed, the separation strip 2705 keeps the handheld portion 2105 and the trigger portion 2115 from coming together and the wearable drug delivery device cannot be triggered.

Referring back to FIG. 23A, the trigger guard 2700 further includes a pull ring 2710 extending from a point along the separation strip 2705. The pull ring 2710 facilitates removing the separation strip 2705 from the gap to allow the wearable drug delivery device 2100 to be triggered. The pull ring 2710 can swing towards or away from the separation strip 2705 by way of a virtual hinge 2715. The virtual hinge 2715 is located at the base of the pull ring 2710 where it extends from the separation strip 2705.

When the user wears the wearable drug delivery device 2100 around their wrist (or other body part), the pull ring 2710 swings towards the wearable drug delivery device 2100, and is sandwiched between the wearable drug delivery device 2100 and the user's wrist (or other body part). In this position, the user cannot access or otherwise use the pull ring 2710 to remove the separation strip 2705 and thus, cannot trigger the wearable drug delivery device.

Figure 24C:
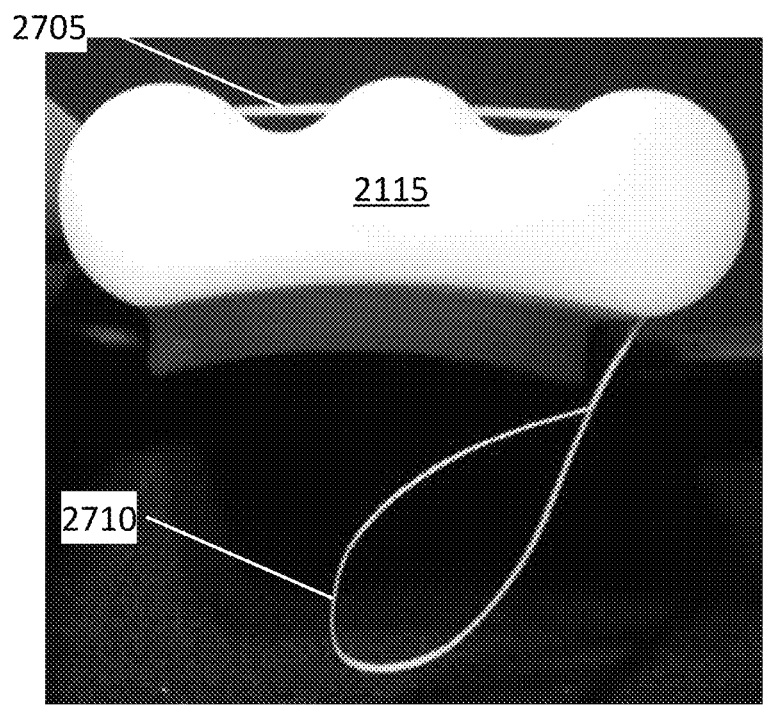

As shown in FIG. 24C, when the user removes the wearable drug delivery device 2100 from their wrist (or other body part), the pull ring 2710 swings away from the wearable drug delivery device. In this deployed position, the user can access the pull ring 2710 and pull on it to remove the separation strip 2705 from the wearable drug delivery device; and thus can trigger the device. This feature is useful because the wearable drug delivery device cannot be activated while wearing the device. The wearable drug delivery device can only be activated when the device is removed from the user's wrist (or other body part), thus adding to the safety of the device.

Figure 24D:
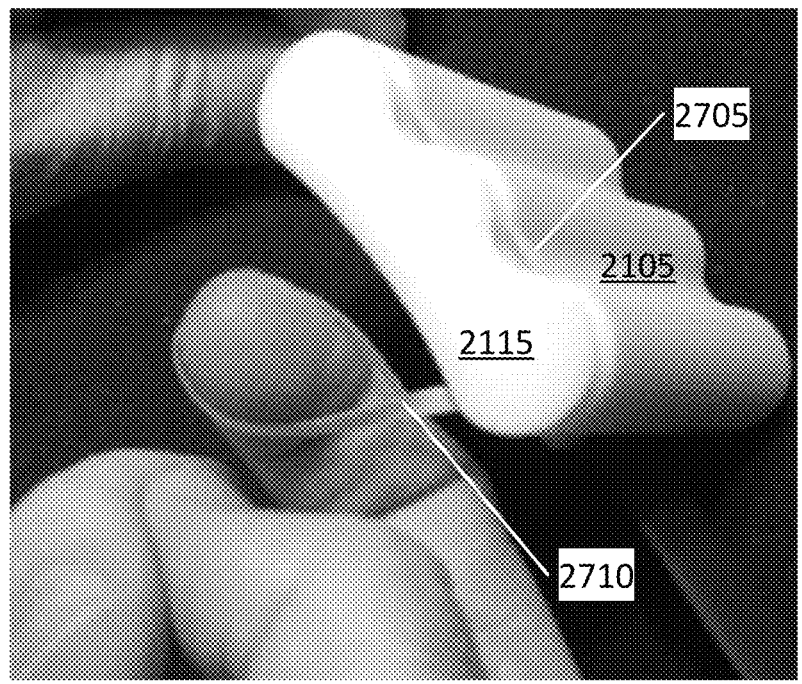
Figure 24E:
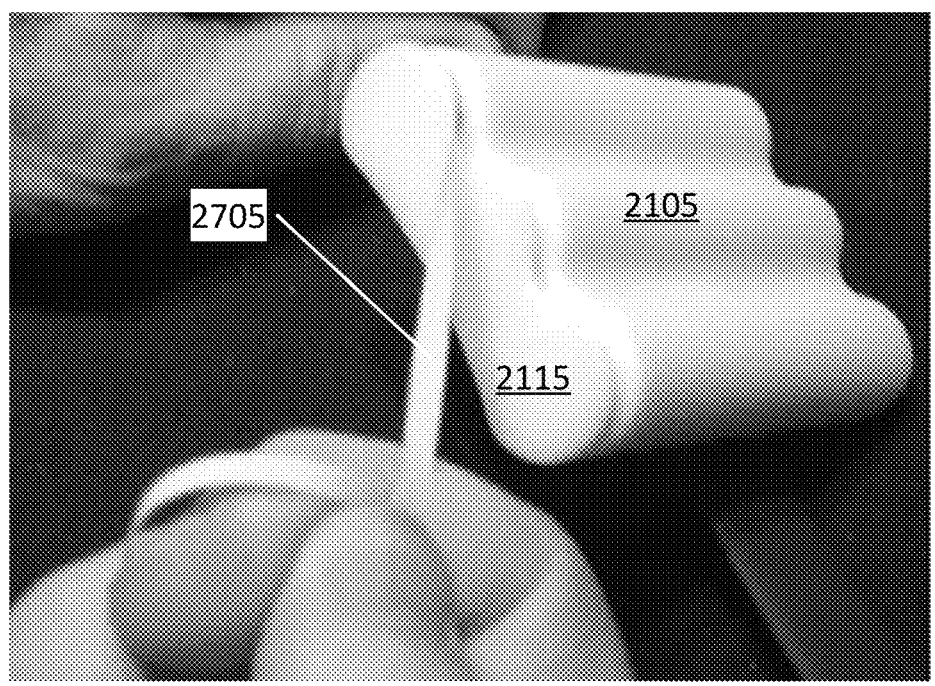

As shown in FIGS. 24D and 24E, the user unwraps the separation strip 2705 from the wearable drug delivery device uses the pull ring 2710. This user action can be further facilitated by one or more pre-weakened areas (not shown) in the separation strip 2705. For example, material joining the separation strip 2705 to the handheld portion 2105 and the trigger portion 2115 can be thinned making it easier to tear the separation strip 2705 away from the wearable drug delivery device. In another example, material joining the separation strip 2705 to the handheld portion 2105 and the trigger portion 2115 can be perforated, making it easier to tear the separation strip 2705 away from the wearable drug delivery device.

Figure 25:
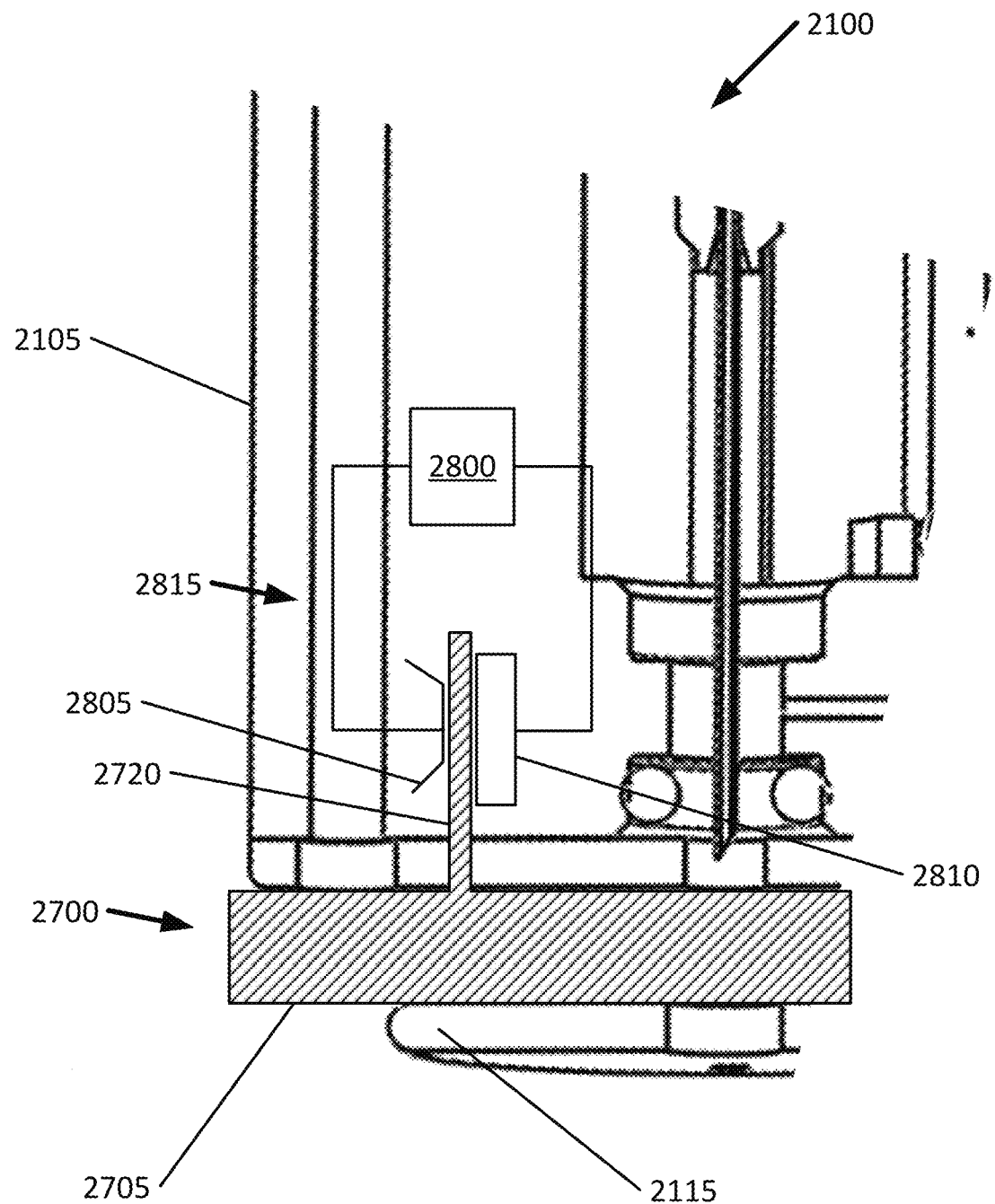
FIG. 25 is a cut-away view of the wearable drug delivery device of FIG. 16 with a mechanism for activating electronics.

FIG. 25 shows another example of the trigger guard 2700 including a tooth 2720 for controlling electronics 2800, such as a communication module, housed within the handheld portion 2105. The tooth 2720 extends from the separation strip 2705 in the direction of the short dimension of the trigger guard 2700. When the trigger guard 2700 is on the wearable drug delivery device 2100, the tooth 2720 extends into the handheld portion 2105 through a slot. Inside, the tooth 2720 is positioned between an electrical contact 2805 and a battery 2810. The electrical contact 2805 and battery 2810 are electrically coupled to the electronics 2800 to form an electronic circuit 2815.

The tooth 2720 is made from nonconductive material, such as plastic. (Some examples of the trigger guard 2700 are made from one material, in which case, the entire trigger guard 2700 is nonconductive). Consequently, positioning the tooth 2720 between the electrical contact 2805 and battery 2810 creates a discontinuity in the electronic circuit 2815 and the electronics 2800 is inactive. The tooth feature is also advantageous because it reduces the loss of battery power over time, which in turn increases the shelf life of the wearable drug delivery device 2100.

When the trigger guard 2700 is removed from the wearable drug delivery device 2100 (e.g., to activate the wearable drug delivery device 2100), the tooth 2720 is pulled out the handheld portion 2105 allowing the electrical contact 2805 and the battery 2810 to connect. This completes the electrical circuit 2815 and activates the electronics 2800. This arrangement is particularly advantageous because both the wearable drug delivery device 2100 and the electronics 2800 can be activated at the same time with one action. Additional, no additional electronic component like a switch is required to control the electronics 2800, making the electronic circuit 2815 simpler, less costly, and more reliable.

As just described, the electronics 2800 can be a communication module. The communication module can provide information to the user when they activate the wearable drug delivery device (e.g., when they remove the trigger guard 2700). For example, speakers built into the wearable drug delivery device 2100 play an audio recording of how to use the device when the user activates the device. It is understood that is beneficial to provide instructions to the user as the user is carrying them out.

Figure 26:
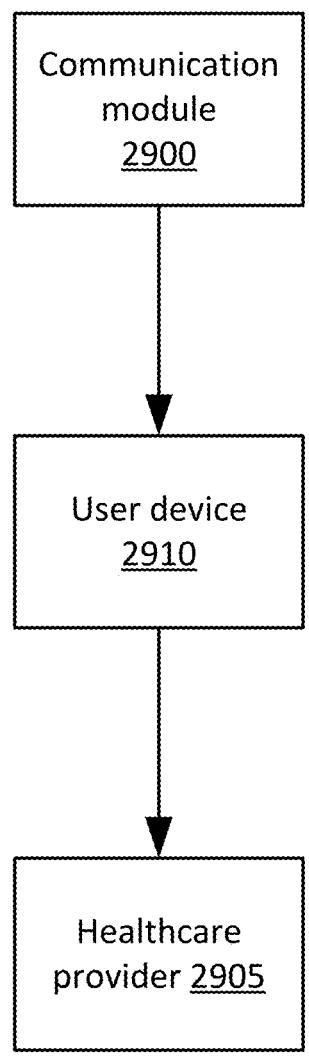
FIG. 26 is block diagram of an example communication module of the wearable drug delivery device of FIG. 16.

In FIG. 26, another example of the communication module 2900 can provide information to a healthcare provider 2905, wirelessly, using cellular, WI-FI, BLUETOOTH, Z-WAVE, and ZIGBEE—just to name a few wireless communication protocols. In examples using short range wireless, such as the CC2640 SIMPLELINK BLUETOOTH Wireless Micro Controller Unit by TEXAS INSTRUMENTS, the communication module 2900 can be wirelessly coupled (networked) to a user device 2910, such as a smartphone. The user device 2910, in turn, connects to a healthcare provider 2905 and relays the information. This can be accomplished using an application running on the user device 2910. Advantageously, the healthcare provider 2905 is notified whenever the user activates the wearable drug delivery device, thus adding safety to the device.

A challenge to using an autoinjector to self-administer a drug dose is making sure that the autoinjector needle penetrates the body to a proper depth for delivering the drug. Delivering the drug dose too shallow in the body can reduce the effectiveness of the drug dose or worst yet not, the drug dose has no effect. The present invention addresses this challenge with a dose confirmation module for determining whether a needle has reached a proper depth based on impedance. Impedance changes the deeper the needle goes into conductive tissue, such as skin, fat, and muscle. This is because increased contact with the conductive material changes the overall impedance. The dose confirmation module then notifies a user or healthcare provider whether the proper depth has been reached.

Figures 27A, 27B:
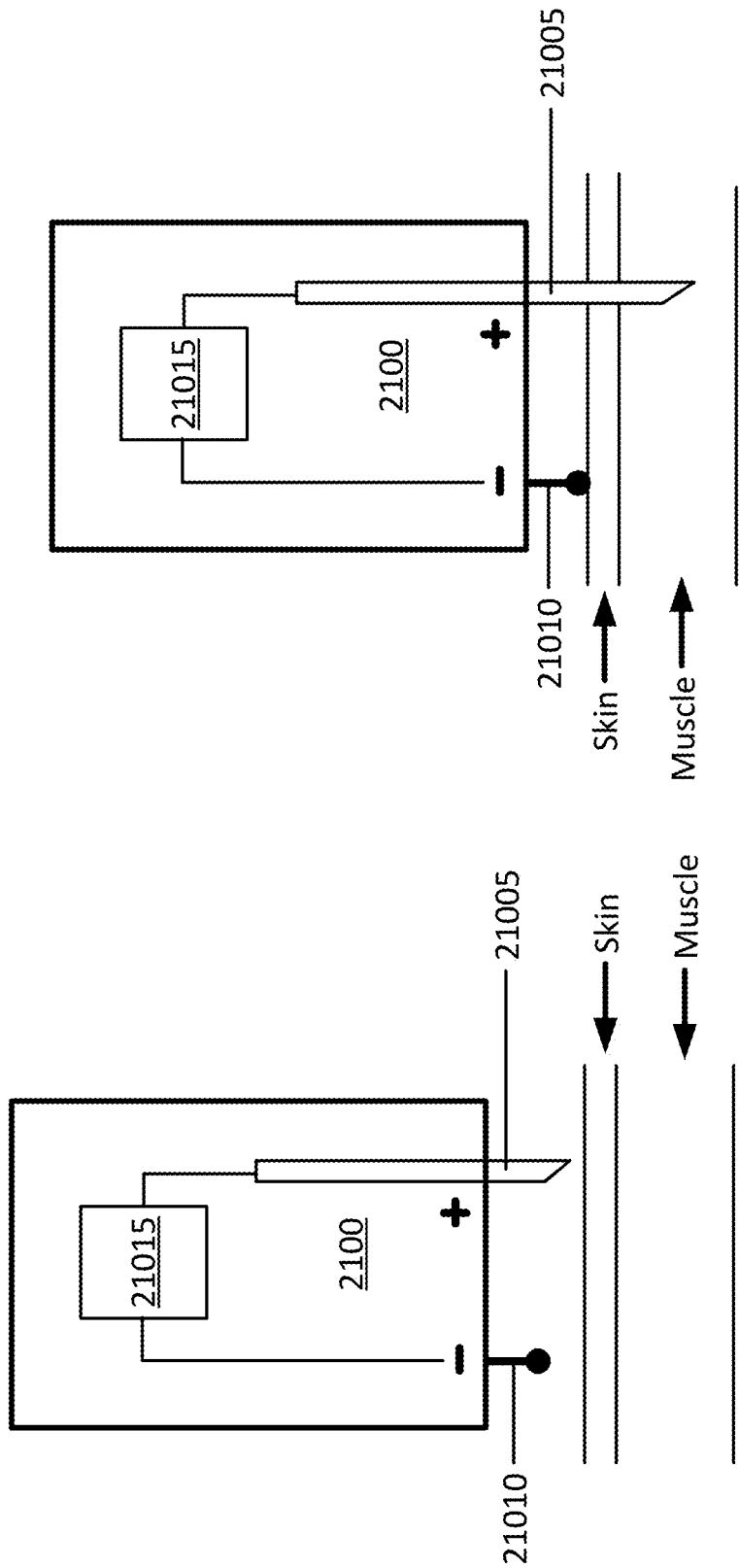
FIGS. 27A-27C are views of an example dose confirmation module of the wearable drug delivery device of FIG. 16.

In FIG. 27A, wearable drug delivery device 2100 includes a dose confirmation module 21000 electrically coupled to needle 21005 (shown in the extended position) and a conductor 21010. With the needle 21005 and conductor 21010 in air, as shown in the figure, the dose confirmation module 21000 measures an impedance of >1,000 ohm (open circuit). In FIG. 27B, the needle 21005 is inserted into muscle (a conductive medium) and the conductor 21010 is in contact with the skin overlaying the muscle (another conductive medium) the measured impedance is about 83 ohms.

Figure 27C:
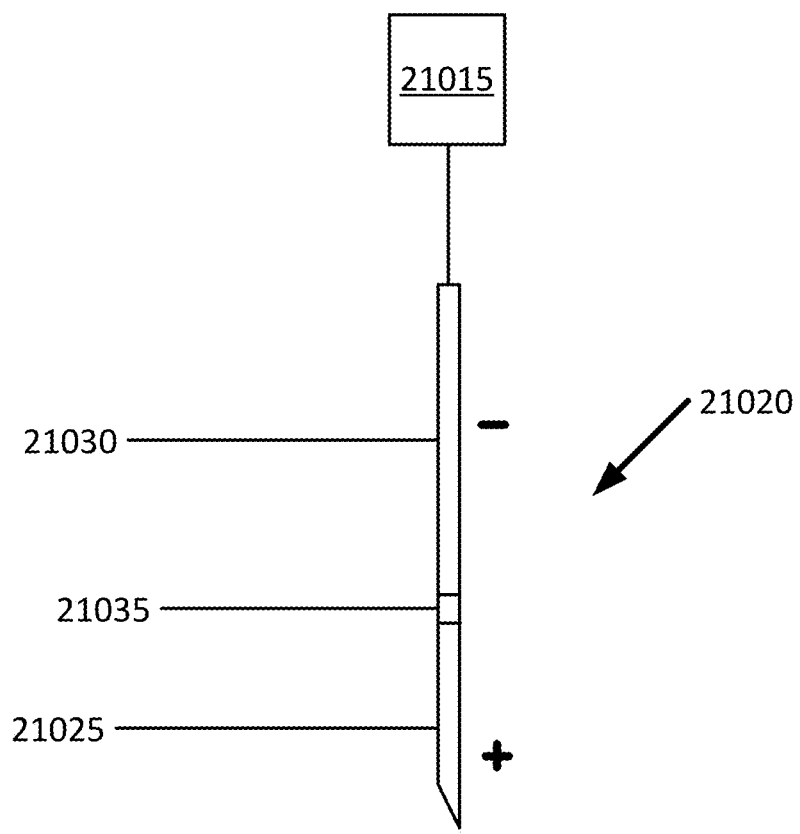

FIG. 27C shows an alternative to the needle 21005 and conductor 21010 configuration of FIG. 27A. The alternative configuration includes a combination needle 21020 having a positive distal region 21025 isolated from a negative proximal region 21030 by an insulating bushing 21035. (The polarities of the distal and proximal regions can be switched.) The combination needle 21020 is electrically coupled to the dose confirmation module 21000. With the combination needle 21020 in air, the dose confirmation module 21000 measures an impedance of >1,000 ohm (open circuit). When the combination needle 21020 penetrates the skin and underlying muscle, both the positive distal region 21025 and the negative proximal region 21030 are in conductive medium; and the dose confirmation module 21000 measures impedance less than 1,000 ohm.

The dose confirmation module 21000 compares the measured impedance to a threshold value and based on the comparison, confirms whether the needle 21005 or combination needle 21020 has reached a proper depth for delivering the drug dose. For example, if the measured impedance is less than or equal to 83 ohms, the dose confirmation module 21000 determines that the proper depth for the injection has been reached (i.e., OK). Impedance measurements greater than 83 ohms indicate that the proper depth for the injection has not been reached (i.e., NOT OK).

A dose confirmation can be communicated to the user using an audio cue (e.g., one beep for OK or two beeps for NOT OK) or a visual cue (e.g., a lit green light for OK or a lit red light for NOT OK). The dose confirmation can also be communicated to a healthcare provider using the communication module 2900 described above with reference to FIG. 26. Advantageously, the foregoing examples can provide the user with immediate feedback on whether they used the wearable drug delivery device 2100 correctly and/or notify a healthcare provider of the same. In some cases, the user and/or healthcare can take corrective measure based on the information.

The invention may be embodied in other specific forms without departing from the spirit or essential characteristics thereof. The foregoing examples are therefore to be considered in all respects illustrative rather than limiting of the invention described herein. Also, the words comprise, include, and/or plural forms of each are open ended and include the listed parts and can include additional parts or steps that are not listed, and the term and/or is open ended and includes one or more of the listed parts or steps and combinations of the listed parts steps.

What is claimed is:

1. A wearable drug delivery device comprising:
   a handheld portion, including a proximal end, a distal end, and a longitudinal axis extending between the proximal and distal ends;
   a trigger portion in slidable engagement with the distal end of the handheld portion;
   a needle assembly disposed within the handheld portion and aligned with the longitudinal axis, the needle assembly being movable towards the distal end of the handheld portion to an extended position by a penetration spring when the penetration spring is activated by the trigger portion sliding towards the proximal end of the handheld portion;
   a drug vial disposed within the handheld portion alongside the needle assembly, the drug vial being moveable towards the distal end of the handheld portion to a seated position by a vial spring when the vial spring is activated by the trigger portion sliding towards the proximal end of the handheld portion;

an integral drug delivery port formed at the distal end of the handheld portion and transverse to the longitudinal axis of the handheld portion, wherein the needle assembly in the extended position and the drug vial in the seated position are in fluid communication with each other by way of the integral drug delivery port;

a rotator coupled to the drug vial, the rotator and the drug vial being urged towards the distal end of the handheld portion by the vial spring;

a yoke extending from the distal end of the handheld portion towards the proximal end, the rotator rests on the yoke thereby resisting movement toward the distal end of the handheld portion and moving the drug vial to the seated position; and wherein the trigger portion includes a trigger blade extending from the trigger portion and through the distal end of the handheld portion, the trigger blade in slidable engagement with the rotator and configured to lift the rotator off the yolk and allow the rotator to move towards the distal end of the handheld portion and move the drug vial to the seated position when the trigger portion slides toward the proximal end of the handheld portion.

2. The wearable drug delivery device of claim 1 wherein the handheld portion includes a concave surface, the concavity of which is defined by a point offset from the longitudinal axis.

3. The wearable drug delivery device of claim 2 wherein the concave surface is configured to conform to a human wrist.

4. The wearable drug delivery device of claim 1 wherein the handheld portion includes a slot; and the device further comprising a band received in the slot for wearing the wearable drug delivery device around a part of a user's body.

5. The wearable drug delivery device of claim 1 wherein the handheld portion and trigger portion are made from a metal, a plastic or a combination of metal and plastic.

6. The wearable drug delivery device of claim 1 wherein the trigger portion slides over the distal end of the handheld portion.

7. The wearable drug delivery device of claim 1 wherein the trigger portion includes a trigger arm extending from the trigger portion and through the distal end of the handheld portion, the trigger arm configured to release energy stored in the penetration spring when the trigger portion slides toward the proximal end of the handheld portion.

8. The wearable drug delivery device of claim 6 wherein the trigger portion includes two trigger arms.

9. The wearable drug delivery device of claim 1 wherein the trigger blade includes an angled surface to lift and turn the rotator off the yoke.

10. The wearable drug delivery device of claim 1 wherein the trigger portion includes three trigger blades.

11. The wearable drug delivery device of claim 1 wherein the needle assembly further includes a J-shaped needle.

12. The wearable drug delivery device of claim 1 wherein the integral drug delivery port includes a vial needle, an exit, and a channel connecting the vial needle to the exit, the vial needle punctures a vial membrane of the drug vial when the drug vial is in the seated position thereby allowing a drug dose to flow through the channel and out the exit.

13. The wearable drug delivery device of claim 12 wherein the exit is a septum seal that is pierced by the needle assembly when the needle assembly is in the extended position.

14. The wearable drug delivery device of claim 1 further comprising:

a return spring interposed between an exterior surface at the distal end of the handheld portion and an opposing surface on the trigger portion, the return spring providing a force separating the handheld portion from the trigger portion; and a latch extending from the opposing surface of the trigger portion and releasable engaged with the handheld portion, the latch when engaged resists the force separating the handheld portion from the trigger portion.

15. The wearable drug delivery device of claim 14 wherein the latch is a leaf spring.

16. The wearable drug delivery device of claim 14 wherein the return spring is a torsion spring.

17. The wearable drug delivery device of claim 1 further comprising a safety guard covering the trigger portion and releaseably attached to the handheld portion by any one of an interference fit and a frangible weld joint.

18. The wearable drug delivery device of claim 1 further comprising:

a safety guard covering the trigger portion and releaseably attached to the handheld portion; and a strip disposed circumferential between the handheld portion and the safety guard, the strip configured to be torn away from the handheld portion and the safety guard thereby allowing the safety guard to be removed from the handheld portion and expose the trigger portion.

19. The wearable drug delivery device of claim 1 wherein the handheld portion further includes an exterior surface parallel to the longitudinal axis, the device further comprising:

a one-way barb projecting from the exterior surface of the handheld portion; and a snap feature joined to the trigger portion by a virtual hinge, the snap feature slides over the exterior surface of the handheld portion and flexes about the virtual hinge, away from the exterior surface, when the trigger portion slides toward the proximal end of the handheld portion and the snap feature slides over the one-way barb.

20. A wearable drug delivery device comprising:

a handheld portion, including a proximal end, a distal end, and a longitudinal axis extending between the proximal and distal ends;

a trigger portion in slidable engagement with the distal end of the handheld portion;

a needle assembly disposed within the handheld portion and aligned with the longitudinal axis, the needle assembly being movable towards the distal end of the handheld portion to an extended position by a penetration spring when the penetration spring is activated by the trigger portion sliding towards the proximal end of the handheld portion;

a drug vial disposed within the handheld portion alongside the needle assembly, the drug vial being moveable towards the distal end of the handheld portion to a seated position by a vial spring when the vial spring is activated by the trigger portion sliding towards the proximal end of the handheld portion;

an integral drug delivery port formed at the distal end of the handheld portion and transverse to the longitudinal axis of the handheld portion, wherein the needle assembly in the extended position and the drug vial in the seated position are in fluid communication with each other by way of the integral drug delivery port;

a return spring interposed between an exterior surface at the distal end of the handheld portion and an opposing surface on the trigger portion, the return spring providing a force separating the handheld portion from the trigger portion; and a latch extending from the opposing surface of the trigger portion and releasable engaged with the handheld portion, the latch when engaged resists the force separating the handheld portion from the trigger portion.

21. The wearable drug delivery device of claim 20 wherein the handheld portion includes a concave surface, the concavity of which is defined by a point offset from the longitudinal axis.

22. The wearable drug delivery device of claim 21 wherein the concave surface is configured to conform to a human wrist.

23. The wearable drug delivery device of claim 20 wherein the handheld portion includes a slot; and
the device further comprising a band received in the slot for wearing the wearable drug delivery device around a part of a user's body.

24. The wearable drug delivery device of claim 20 wherein the handheld portion and trigger portion are made from a metal, a plastic or a combination of metal and plastic.

25. The wearable drug delivery device of claim 20 wherein the trigger portion slides over the distal end of the handheld portion.

26. The wearable drug delivery device of claim 20 wherein the trigger portion includes a trigger arm extending from the trigger portion and through the distal end of the handheld portion, the trigger arm configured to release energy stored in the penetration spring when the trigger portion slides toward the proximal end of the handheld portion.

27. The wearable drug delivery device of claim 25 wherein the trigger portion includes two trigger arms.

28. The wearable drug delivery device of claim 20 further comprising:
a rotator coupled to the drug vial, the rotator and the drug vial being urged towards the distal end of the handheld portion by the vial spring;
a yoke extending from the distal end of the handheld portion towards the proximal end, the rotator rests on the yoke thereby resisting movement toward the distal end of the handheld portion and moving the drug vial to the seated position; and
wherein the trigger portion includes a trigger blade extending from the trigger portion and through the distal end of the handheld portion, the trigger blade in slidable engagement with the rotator and configured to lift the rotator off the yolk and allow the rotator to move towards the distal end of the handheld portion and move the drug vial to the seated position when the trigger portion slides toward the proximal end of the and held portion.

29. The wearable drug delivery device of claim 28 wherein the trigger blade includes an angled surface to lift and turn the rotator off the yoke.

30. The wearable drug delivery device of claim 28 wherein the trigger portion includes three trigger blades.

31. The wearable drug delivery device of claim 20 wherein the needle assembly further includes a J-shaped needle.

32. The wearable drug delivery device of claim 20 wherein the integral drug delivery port includes a vial needle, an exit, and a channel connecting the vial needle to the exit, the vial needle punctures a vial membrane of the drug vial when the drug vial is in the seated position thereby allowing a drug dose to flow through the channel and out the exit.

33. The wearable drug delivery device of claim 32 wherein the exit is a septum seal that is pierced by the needle assembly when the needle assembly is in the extended position.

34. The wearable drug delivery device of claim 20 wherein the latch is a leaf spring.

35. The wearable drug delivery device of claim 20 wherein the return spring is a torsion spring.

36. The wearable drug delivery device of claim 20 further comprising a safety guard covering the trigger portion and releaseably attached to the handheld portion by any one of an interference fit and a frangible weld joint.

37. The wearable drug delivery device of claim 20 further comprising:
a safety guard covering the trigger portion and releaseably attached to the handheld portion; and
a strip disposed circumferential between the handheld portion and the safety guard, the strip configured to be torn away from the handheld portion and the safety guard thereby allowing the safety guard to be removed from the handheld portion and expose the trigger portion.

38. The wearable drug delivery device of claim 20 wherein the handheld portion further includes an exterior surface parallel to the longitudinal axis, the claim further comprising:
a one-way barb projecting from the exterior surface of the handheld portion; and
a snap feature joined to the trigger portion by a virtual hinge, the snap feature slides over the exterior surface of the handheld portion and flexes about the virtual hinge, away from the exterior surface, when the trigger portion slides toward the proximal end of the handheld portion and the snap feature slides over the one-way barb.

39. A wearable drug delivery device comprising:
a handheld portion, including a proximal end, a distal end, and a longitudinal axis extending between the proximal and distal ends;
a trigger portion in slidable engagement with the distal end of the handheld portion;
a needle assembly disposed within the handheld portion and aligned with the longitudinal axis, the needle assembly being movable towards the distal end of the handheld portion to an extended position by a penetration spring when the penetration spring is activated by the trigger portion sliding towards the proximal end of the handheld portion;
a drug vial disposed within the handheld portion alongside the needle assembly, the drug vial being moveable towards the distal end of the handheld portion to a seated position by a vial spring when the vial spring is activated by the trigger portion sliding towards the proximal end of the handheld portion; and
an integral drug delivery port formed at the distal end of the handheld portion and transverse to the longitudinal axis of the handheld portion, wherein the needle assembly in the extended position and the drug vial in the seated position are in fluid communication with each other by way of the integral drug delivery port;
wherein the handheld portion further includes an exterior surface parallel to the longitudinal axis, the device further comprising;

a one-way barb projecting from the exterior surface of the handheld portion; and a snap feature joined to the trigger portion by a virtual hinge, the snap feature slides over the exterior surface of the handheld portion and flexes about the virtual hinge, away from the exterior surface, when the trigger portion slides toward the proximal end of the handheld portion and the snap feature slides over the one-way barb.

40. The wearable drug delivery device of claim 39 wherein the handheld portion includes a concave surface, the concavity of which is defined by a point offset from the longitudinal axis.

41. The wearable drug delivery device of claim 40 wherein the concave surface is configured to conform to a human wrist.

42. The wearable drug delivery device of claim 39 wherein the handheld portion includes a slot; and the device further comprising a band received in the slot for wearing the wearable drug delivery device around a part of a user's body.

43. The wearable drug delivery device of claim 39 wherein the handheld portion and trigger portion are made from a metal, a plastic or a combination of metal and plastic.

44. The wearable drug delivery device of claim 39 wherein the trigger portion slides over the distal end of the handheld portion.

45. The wearable drug delivery device of claim 39 wherein the trigger portion includes a trigger arm extending from the trigger portion and through the distal end of the handheld portion, the trigger arm configured to release energy stored in the penetration spring when the trigger portion slides toward the proximal end of the handheld portion.

46. The wearable drug delivery device of claim 44 wherein the trigger portion includes two trigger arms.

47. The wearable drug delivery device of claim 39 further comprising:

a rotator coupled to the drug vial, the rotator and the drug vial being urged towards the distal end of the handheld portion by the vial spring;

a yoke extending from the distal end of the handheld portion towards the proximal end, the rotator rests on the yoke thereby resisting movement toward the distal end of the handheld portion and moving the drug vial to the seated position; and wherein the trigger portion includes a trigger blade extending from the trigger portion and through the distal end of the handheld portion, the trigger blade in slidable engagement with the rotator and configured to lift the rotator off the yolk and allow the rotator to move towards the distal end of the handheld portion and move the drug vial to the seated position when the trigger portion slides toward the proximal end of the and held portion.

48. The wearable drug delivery device of claim 47 wherein the trigger blade includes an angled surface to lift and turn the rotator off the yoke.

49. The wearable drug delivery device of claim 47 wherein the trigger portion includes three trigger blades.

50. The wearable drug delivery device of claim 39 wherein the needle assembly further includes a J-shaped needle.

51. The wearable drug delivery device of claim 39 wherein the integral drug delivery port includes a vial needle, an exit, and a channel connecting the vial needle to the exit, the vial needle punctures a vial membrane of the drug vial when the drug vial is in the seated position thereby allowing a drug dose to flow through the channel and out the exit.

52. The wearable drug delivery device of claim 51 wherein the exit is a septum seal that is pierced by the needle assembly when the needle assembly is in the extended position.

53. The wearable drug delivery device of claim 39 further comprising:

a return spring interposed between an exterior surface at the distal end of the handheld portion and an opposing surface on the trigger portion, the return spring providing a force separating the handheld portion from the trigger portion; and a latch extending from the opposing surface of the trigger portion and releasable engaged with the handheld portion, the latch when engaged resists the force separating the handheld portion from the trigger portion.

54. The wearable drug delivery device of claim 53 wherein the latch is a leaf spring.

55. The wearable drug delivery device of claim 53 wherein the return spring is a torsion spring.

56. The wearable drug delivery device of claim 39 further comprising a safety guard covering the trigger portion and releaseably attached to the handheld portion by any one of an interference fit and a frangible weld joint.

57. The wearable drug delivery device of claim 39 further comprising:

a safety guard covering the trigger portion and releaseably attached to the handheld portion; and a strip disposed circumferential between the handheld portion and the safety guard, the strip configured to be torn away from the handheld portion and the safety guard thereby allowing the safety guard to be removed from the handheld portion and expose the trigger portion.

* * * * *